(12) United States Patent
Webel et al.

(10) Patent No.: US 7,320,876 B2
(45) Date of Patent: Jan. 22, 2008

(54) PHYTASE-CONTAINING ANIMAL FOOD AND METHOD

(75) Inventors: Douglas M. Webel, Noblesville, IN (US); Donald E. Orr, Jr., Nobelesville, IN (US); Frank E. Ruch, Jr., Falmouth, ME (US); Xingen Lei, Ithaca, NY (US)

(73) Assignees: Phytex, LLC, Portland, ME (US); Cornell Research Foundation, Inc., Ithaca, NY (US)

( * ) Notice: Subject to any disclaimer, the term of this patent is extended or adjusted under 35 U.S.C. 154(b) by 257 days.

(21) Appl. No.: 10/284,962

(22) Filed: Oct. 31, 2002

(65) Prior Publication Data

US 2003/0206913 A1 Nov. 6, 2003

Related U.S. Application Data

(60) Provisional application No. 60/335,303, filed on Oct. 31, 2001.

(51) Int. Cl.
A23K 1/165 (2006.01)
C12N 9/16 (2006.01)

(52) U.S. Cl. ............... 435/15; 435/196; 435/252.3; 435/320.1; 536/23.2; 426/615; 426/623

(58) Field of Classification Search .............. 435/21, 435/196, 252.3, 320.1; 536/23.2; 426/615, 426/623
See application file for complete search history.

(56) References Cited

U.S. PATENT DOCUMENTS

| 3,819,528 A | 6/1974 | Berry |
| 3,860,484 A | 1/1975 | O Malley |
| 3,966,971 A | 6/1976 | Morehouse et al. |
| 4,038,140 A | 7/1977 | Jaworek et al. |
| 4,375,514 A | 3/1983 | Siewert et al. |
| 4,460,683 A | 7/1984 | Gloger et al. |
| 4,470,968 A | 9/1984 | Mitra et al. |
| 4,734,283 A | 3/1988 | Siren |
| 4,765,994 A | 8/1988 | Holmgren |
| 4,778,761 A | 10/1988 | Miyanohara et al. |
| 4,914,029 A | 4/1990 | Caransa et al. |
| 4,915,960 A | 4/1990 | Holmgren |
| 4,950,609 A | 8/1990 | Tischer et al. |
| 4,997,767 A | 3/1991 | Nozaki et al. |
| 5,024,941 A | 6/1991 | Maine et al. |
| 5,200,399 A | 4/1993 | Wettlaufer et al. |
| 5,268,273 A | 12/1993 | Buckholz |
| 5,290,765 A | 3/1994 | Wettlaufer et al. |
| 5,316,770 A | 5/1994 | Edwards, Jr. |
| 5,318,903 A | 6/1994 | Bewert et al. |
| 5,366,736 A | 11/1994 | Edwards, Jr. |
| 5,436,156 A | 7/1995 | VanGorcom et al. |
| 5,443,979 A | 8/1995 | Vanderbeke et al. |
| 5,480,790 A | 1/1996 | Tischer et al. |
| 5,492,821 A | 2/1996 | Callstrom et al. |
| 5,516,525 A | 5/1996 | Edwards, Jr. |
| 5,554,399 A | 9/1996 | Vanderbeke et al. |
| 5,556,771 A | 9/1996 | Shen et al. |
| 5,593,963 A | 1/1997 | Van Ooijen et al. |
| 5,612,055 A | 3/1997 | Bedford et al. |
| 5,691,154 A | 11/1997 | Callstrom et al. |
| 5,716,655 A | 2/1998 | Hamstra et al. |
| 5,736,625 A | 4/1998 | Callstrom et al. |
| 5,780,292 A | 7/1998 | Nevalainen et al. |
| 5,827,709 A | 10/1998 | Barendse et al. |
| 5,830,696 A | 11/1998 | Short |
| 5,830,733 A | 11/1998 | Nevalainen et al. |
| 5,834,286 A | 11/1998 | Nevalainen et al. |
| 5,853,779 A | 12/1998 | Takebe et al. |
| 5,863,533 A | 1/1999 | Van Gorcom et al. |
| 5,876,997 A | 3/1999 | Kretz |
| 5,891,708 A | 4/1999 | Saniez et al. |
| 5,900,525 A | 5/1999 | Austin-Phillips et al. ... 426/636 |

(Continued)

FOREIGN PATENT DOCUMENTS

CN 1126243 7/1996

(Continued)

OTHER PUBLICATIONS

Murry et al., "The Effect of Microbial Phytase in a Pear Millet-Soybean Meal Diet on Apparent Digestibility and Retention of Nutrients, Serum Mineral Concentration, and Bone Mineral Density of Nursery Pigs," *J. Animal Science*, 75: 1284-1291 (1997).
Scott et al., "The Effect of Phosphorus, Phytase Enzyme, and Calcium on the Performance of Layers Fed Corn-Based Diets," *Poultry Science*, 78: 1742-1749 (1999).
Sebastian et al., "Apparently Digestibility of Protein and Amino Acids in Broiler Chickens Fed a Corn-Soybean Diet Supplemented with Microbial Phytase," *Poultry Science*, 76: 1760-1769 (1997).
PIR-68 Database, Accession No. B36733, corresponding to Greiner, et al., *Arch. Biochem. Biophys.*, vol. 303, pp. 107-113 (1993) (cited in the IDS).
Granovskil, et al., "Expression of Hepatitis B Virus HBsAg Gene in Yeast Cells under Control of Promoter Region of PGO5 Gene," *Soviet progress in Virology*, vol. 5, pp. 45-47 (1985).
Touati, et al., "Pleiotropic Mutations in appR Reduce pH 2.5 Acid Phosphatase Expression and Restore Succinate Utilisation in CRP-deficient Strains of *Escherichia coli,*" *Mol. Gen. Genet.*, vol. 202, pp. 257-264 (1986).

(Continued)

*Primary Examiner*—Tekchand Saidha
(74) *Attorney, Agent, or Firm*—Barnes & Thornburg LLP

(57) ABSTRACT

A method is described for improving the nutritional value of a foodstuff comprising a source of myo-inositol hexakisphosphate by feeding the foodstuff in combination with a phytase expressed in yeast. The method comprises the step of feeding the animal the foodstuff in combination with a phytase expressed in yeast wherein the phytase can be selected from the group consisting of AppA1, AppA2 and a site-directed mutant of AppA. The invention also enables reduction of the feed to weight gain ratio and an increase bone mass and mineral content of an animal. A foodstuff and a feed additive comprising AppA2 or a site-directed mutant of AppA are also described.

35 Claims, 6 Drawing Sheets

U.S. PATENT DOCUMENTS

| | | | |
|---|---|---|---|
| 5,902,615 A | 5/1999 | Saniez et al. | |
| 5,935,624 A | 8/1999 | DeLuca et al. | |
| 5,955,448 A | 9/1999 | Colaco et al. | |
| 5,972,669 A | 10/1999 | Harz et al. | |
| 5,985,605 A | 11/1999 | Cheng et al. | |
| 5,989,600 A | 11/1999 | Nielsen et al. | |
| 6,022,555 A | 2/2000 | DeLuca et al. | |
| 6,039,942 A | 3/2000 | Lassen et al. | |
| 6,063,431 A | 5/2000 | Bae et al. | |
| 6,083,541 A | 7/2000 | Hamstra et al. | |
| 6,110,719 A | 8/2000 | Kretz | |
| 6,139,892 A | 10/2000 | Fredlund et al. | |
| 6,139,902 A | 10/2000 | Kondo et al. | |
| 6,140,077 A | 10/2000 | Nakamura et al. | |
| 6,183,740 B1 | 2/2001 | Short et al. | |
| 6,190,897 B1 | 2/2001 | Kretz | |
| 6,204,012 B1 | 3/2001 | Hellmuth et al. | |
| 6,248,938 B1 | 6/2001 | Austin-Phillips et al. | 800/298 |
| 6,261,592 B1 | 7/2001 | Nagashima et al. | |
| 6,264,946 B1 | 7/2001 | Mullertz et al. | |
| 6,274,178 B1 | 8/2001 | Beven et al. | |
| 6,277,623 B1 | 8/2001 | Oh et al. | |
| 6,284,502 B1 | 9/2001 | Maenz et al. | |
| 6,291,221 B1 | 9/2001 | van Loon et al. | 435/196 |
| 6,309,870 B1 | 10/2001 | Kondo et al. | |
| 6,350,602 B1 | 2/2002 | Van Gorcom et al. | |
| 6,391,605 B1 | 5/2002 | Kostrewa et al. | |
| 6,451,572 B1 | 9/2002 | Lei | 435/196 |
| 6,475,762 B1 | 11/2002 | Stafford et al. | 435/196 |
| 6,511,699 B1 | 1/2003 | Lei | 426/630 |
| 6,599,735 B1 | 7/2003 | Bartók et al. | 435/286.5 |
| 6,720,014 B1 | 4/2004 | Short et al. | |
| 6,841,370 B1 | 1/2005 | Lei | |
| 6,974,690 B2 | 12/2005 | Lei | |
| 7,022,371 B2 | 4/2006 | Stafford et al. | |
| 7,026,150 B2 | 4/2006 | Lei | |
| 2001/0018197 A1 | 8/2001 | Wong et al. | |
| 2001/0029042 A1 | 10/2001 | Fouache et al. | |
| 2002/0068350 A1 | 6/2002 | Kondo et al. | |
| 2002/0102692 A1 | 8/2002 | Lei | |
| 2002/0127218 A1 | 9/2002 | Svendsen et al. | |
| 2002/0136754 A1 | 9/2002 | Short et al. | |
| 2002/0192791 A1 | 12/2002 | Lei | |
| 2003/0072844 A1 | 4/2003 | Lei | |
| 2003/0092155 A1 | 5/2003 | Kostrewa et al. | |
| 2004/0126844 A1 | 7/2004 | Lei et al. | |
| 2005/0095691 A1 | 5/2005 | Lei | |
| 2006/0153902 A1 | 7/2006 | Lei | |

FOREIGN PATENT DOCUMENTS

| | | |
|---|---|---|
| EP | 0 420 358 | 4/1991 |
| EP | 0 449 376 | 10/1991 |
| EP | 0 556 883 | 8/1993 |
| EP | 0 649 600 | 4/1995 |
| EP | 0 684 313 | 11/1995 |
| EP | 0 699 762 | 3/1996 |
| EP | 0 772 978 | 5/1997 |
| EP | 0 779 037 | 6/1997 |
| EP | 0 897 010 | 2/1999 |
| EP | 0 897 985 | 2/1999 |
| EP | 0 909 821 | 4/1999 |
| EP | 0 925 723 | 6/1999 |
| EP | 0 955 362 | 11/1999 |
| EP | 0 960 934 | 12/1999 |
| GB | 2 286 396 | 8/1995 |
| GB | 2 316 082 | 2/1998 |
| JP | 10-276789 | 10/1998 |
| JP | 2001-292789 | 10/2001 |
| RU | 2 113 468 C1 | 6/1998 |
| WO | WO 86/01179 A1 | 2/1986 |
| WO | WO90/05182 | 5/1990 |
| WO | WO90/05053 | 4/1991 |
| WO | WO91/14773 | 10/1991 |
| WO | WO91/14782 | 10/1991 |
| WO | WO93/14645 | 8/1993 |
| WO | WO93/16175 | 8/1993 |
| WO | WO93/19759 | 10/1993 |
| WO | WO94/03072 | 2/1994 |
| WO | WO94/03612 | 2/1994 |
| WO | WO97/16076 | 5/1997 |
| WO | WO97/35017 | 9/1997 |
| WO | WO97/39638 | 10/1997 |
| WO | WO97/45009 | 12/1997 |
| WO | WO97/48812 | 12/1997 |
| WO | WO98/05785 | 2/1998 |
| WO | WO98/06856 | 2/1998 |
| WO | WO98/20139 | 5/1998 |
| WO | WO98/30681 | 7/1998 |
| WO | WO98/44125 | 10/1998 |
| WO | WO98/54980 | 12/1998 |
| WO | WO99/08539 | 2/1999 |
| WO | WO 99/49022 A1 | 9/1999 |
| WO | WO99/49740 | 10/1999 |
| WO | WO 00/10404 | 3/2000 |
| WO | WO 00/20569 | 4/2000 |
| WO | WO 00/41509 | 7/2000 |
| WO | WO 00/43503 A1 | 7/2000 |
| WO | WO 00/47060 | 8/2000 |
| WO | WO 00/58481 A | 10/2000 |
| WO | WO 00/71728 | 11/2000 |
| WO | WO 00/72700 | 12/2000 |
| WO | WO 01/36607 | 5/2001 |
| WO | WO 01/58275 | 8/2001 |
| WO | WO 01/58276 | 8/2001 |

OTHER PUBLICATIONS

Sidhu, et al., "Analysis of α-Factor Secretion Signals by Fusing with Acid Phosphatase of Yeast," *Gene*, vol. 54, pp. 175-184 (1987).

Zvonok, et al., "Construction of Versatile *Escherichia coli*-Yeast Shuttle Vectors for Promoter Testing in *Saccharomyces cerevisiae*," *Gene*, vol. 66(2), pp. 313-318 (1988).

Leeson, et al., "Efficacy of New Bacterial Phytase in Poultry Diets," *Can. J. Anim. Sci.*, vol. 80, pp. 527-528 (2000).

Ostanin, et al., Asp304 of *Escherichia coli* Acid Phosphatase is Involved in Leaving Group Protonation, *J. of Biol. Chem.*, vol. 268(28), pp. 20778-20784 (1993).

Ostanin, et al., "Overexpression, Site-Directed Mutagenesis, and Mechanism of *Escherichia coli* Acid Phosphatase," *J. of Biol. Chem.*, vol. 267(32), pp. 22830-22836 (1992).

Blondeau, et al., Development of High-Cell-Density Fermentation for Heterologous Interleukin 1β Production in Kluyveromyces lactis Controlled by the PHO5 Promoter, *Appl. Microbiol. Biotechnol.*, vol. 41, pp. 324-329 (1994).

Moore, et al., "Molecular Cloning, Expression and Evaluation pf Phosphohydrolases for Phytate-Degrading Activity," *J. of Indus. Microbiol.*, vol. 14, pp. 396-402 (1995).

Verwoerd, et al., "Stable Accumulation of *Aspergillus niger* Phytase in Transgenic Tobacco Leaves," *Plant Physiol.*, vol. 109, pp. 1199-1205 (1995).

Bronsted et al., "Effect of Growth Conditions on Expression of the Acid Phosphatase (cyx-appA) Operon and the appY Gene, Which Encodes a Transcriptional Activator of *Escerichia coli*," *J. of Bacteriol.*, vol. 178)6), pp. 1556-1564 (1996).

Murray, et al., "Construction of Artificial Chromosomes in Yeast," *Nature*, vol. 305, pp. 189-193 (1983).

Greiner et al., "Purification and Characterization of Two Phytases from *Escherichia coli*," *Arch. of Biochem. and Biophys.*, vol. 303, pp. 107-113 (1993).

Minamiguchi et al., "Secretive Expression of the *Aspergillus aculeatus* Cellulase (FI-CM Case) by *Saccharomyces cerevisiae*," *J. of Fermentation and Bioeng.*, vol. 79(4), pp. 363-366 (1995).

Wodzinski et al., "Phytase," *Adv. in Applied Microbiol.*, vol. 42, pp. 263-302 (1996).

Konietzny et al., "Model Systems for Developing Detection Methods for Foods Deriving from Genetic Engineering," *J. of Food Composition and Anal.*, vol. 10, pp. 28-35 (1997).

Sun et al., "Expression of *Aspergillus niger* Phytase in Yeast *Saccharomyces cerevisiae* for Poultry Diet Supplementation," *Poultry Sci.*, vol. 76(Supp. 1), p. 5 (1997) (abstract only).

Yao, et al., "Recombinant *Pichia pastoris* Overexpressing Bioactive Phytase," *Science in China (Series C) Life Sciences*, vol. 41(3), pp. 330-336 (1998).

Han, et al., "Expression of an *Aspergillus niger* Phytase Gene (phy A) in *Saccharomyces cerevisiae*," *Applied and Environmental Microbiol.*, vol. 65(5), pp. 1915-1918 (1999).

Maugenest, et al., "Cloning and Characterization of cDNA Encoding a Maize Seedling Phytase," *Biochem. J.*, vol. 322, pp. 511-517 (1997).

Tschopp, et al., "Heterologous Gene Expression in Methylotrophic Yeast," *Biotechnology*, vol. 18, pp. 305-322 (1991).

Kumagai, et al., "Conversion of Starch to Ethanol in a Recombinant *Saccharomyces cerevisiae* Strain Expressing Rice α-amylase from a Novel *Pichia pastoris* Alcohol Oxidase Promoter," *Biotechnology*, vol. 11, pp. 606-610 (1993).

Van Hartingsveldt, et al., "Cloning, Characterization, and Overexpression of the Phytase-Encoding Gene (phy A) of *Aspergillus niger*," *Gene*, vol. 127, pp. 87-94 (1993).

Phillippy, et al., "Expression of an *Aspergillus niger* Phytase (Phy A) in *Escherichia coli*," *J. Agric. Food Chem.*, vol. 45(8), pp. 3337-3342 (1997).

Rodriguez, et al., "Sire-Directed Mutagenesis Improves Catalytic Efficiency and Thermostability of *Escherichia coli* pH 2.5 Acid Phosphatase/Phytase Expressed in *Pichia pastoris*," *Arch. of Biochemistry and Biophys.*, vol. 382(1), pp. 105-112 (2000).

Boer, et al., "Characterization of Trichoderma reesei Cellobiohydrolase Cel7a Secreted from *Pichia pastoris* Using Two Different Promoters," *Biotech. and Bioengineering*, vol. 69(5), pp. 486-494 (2000).

Takahashi, et al., "Independent Production of Two Molecular Forms of a Recombinant *Rhizopus oryzae* Lipase by KEX2-Engineered Strains of *Saccharomyces cerevisiae*," *Appl. Microbiol. Biotech.*, vol. 52(4), pp. 534-540 (1999).

Meldgaard, et al., "Different Effects if N-Glycosylation on the Thermostability of Highly Homologus Bacterial (1,3-1,4)-β-Glucanases Secreted from Yeast," *Microbiol.*, vol. 140(1), pp. 159-166 (1994).

Kanai, et al., "Recombinant Thermostable Cycloinulo-oligosaccharide Fructanotransferase Produced by *Saccharomyces cerevisiae*," *Appl. Environ. Microbiol.*, vol. 63(12), pp. 4956-4960 (1997).

Terashima, et al., "The Roles of the N-Linked Carbohydrate Chain of Rice α-amylase in Thermostability and Enzyme Kinetics," *Eur. J. Biochem.*, vol. 226, pp. 249-254 (1994).

Atlung, et al., "Role of the Transcriptional Activator AppY in Regulation of the cyx appA Operon of *Escherichia coli* by Anaerobiosis, Phosphate Starvation, and Growth Phase," *J. Bacteriol.*, vol. 176(17), pp. 5414-5422 (1994).

Belin, et al., "A Pleiotropic Acid Phosphatase-Deficient Mutant of *Escherichia coli* Shows Premature Termination in the dsbA," *Mol. Gen. Genet.*, vol. 242, pp. 23-32 (1994).

Dassa, et al., "Indentification of the Gene appA for the Acid Phosphatase (pH Optimum 2.5) of *Escherichia coli*," *Mol. Gen. Genet.*, vol. 200, pp. 68-73 (1985).

Piddington, et al., "The Cloning and Sequencing of the Genes Encoding Phytase (phy) and pH 2.5-Optimum Acid Phosphatase (aph) from *Aspergillus niger* var. awamori," *Gene*, vol. 133, pp. 55-62 (1993).

Jia, et al., "Purification, Crystallization, and Preliminary X-ray Analysis of the *Escherichia coli* Phytase," *Acta Cryst.*, vol. D54, pp. 647-649 (1998).

Kim, et al., "Cloning of the Thermostable Phytase Gene (phy) from Bacillus sp. DS11 and its Overexpression in *Escherichia coli*," *FEMS Microbiol. Lett.*, vol. 162, pp. 185-191 (1998).

Kerovuo, et al., "Isolation, Characterization, Molecular Gene Cloning, and Sequencing of a Novel Phytase from *Bacillus subtillis*," *Appl. and Environ. Microbiol.*, vol. 64(6), pp. 2079-2085 (1998).

Wyss, et al., "Biophysical Characterization of Fungal. Phytases (myo-inositol Hexakisphosphate Phosphohydrolases): Molecular Size, Glycosilation Pattern, and Engineering of Proteolytic Resistance," *Appl. and Environ. Microbiol.*, vol. 65(2), pp. 359-366 (1999).

Wyss, et al., "Biochemical Characterization of Fungal Phytases (myo-Inositol Hexakisphosphate Phosphohydrolases): Catalytic Properties," *Appl. and Environ. Microbiol.*, vol. 65(2), pp. 367-373 (1999).

Han, et al., "Role of Glycosylation in the Functional Expression of an *Aspergilius niger* Phytase (phyA) in *Pichia pastoris*," *Arch. of Biochem. and Biophys.*, vol. 364(1), pp. 83-90 (1999).

Rodriguez, et al., "Different Sensitivity of Recombinant *Aspergillus niger* Phytase (r-PhyA) and *Escherichia coli* ph 2.5 Acid Phosphatase (r-AppA) to Trypsin and Pepsin in Vitro," *Arch. of Biochem. and Biophys.*, vol. 365(2), pp. 262-267 (1999).

Rodriguez, et al., "Cloning, Sequencing, and Expression of an *Escherichia coli* Acid Phosphatase/Phytase Gene (appA2) Isolated from Pig Colon," *Biochem. and Biophys. Res. Commun.*, vol. 257, pp. 117-123 (1990).

Divakaran, et al., "In Vitro Studies on the Interaction of Phytase with Trypsin and Amylase Extracted from Shrimp (*Penaeus vannamei*) Hepatopancreas," *J. Agric. Food Chem.*, vol. 46, pp. 4973-4976 (1998).

Dassa, et al., "The Complete Nucleotide Sequence of the *Escherichia coli* Gene appA Reveals Signification Homology between pH 2.5 Acid Phosphatase and Glucose-1-Phosphatase," *J. of Bacteriology*, vol. 172(9), pp. 5497-5500 (1990).

Han, et al., "Development of Phytase Overexpressing Microbes for Nutritional Use," Poster Presentation at Cornell University's Biotechnology Symposium, Ithaca, New York (Oct. 15, 1997).

Lei, et al., "Biotechnological Developments of Effective Phyyases for Mineral Nutrition and Environmental Protection," *Appl. Microbiol. Biotech.*, vol. 57(4), pp. 474-481 (2001).

Lei, et al., "Nutritional Benefits of Phytase and Dietary Determinants of Its Efficacy," *J. Appl. Anim. Res.*, vol. 17, pp. 97-112 (2000).

Chiarugi, et al., "Differential Role of Four Cysteines on the Activity of a Low M, Phosphotyrosine Protein Phosphatase," *FEBS Letters*, vol. 310(1), pp. 9-12 (1992).

Lim, et al., "Crystal Structure of *Escherichia coli* Phytase and Its Complex with Phytate," *Nature Structure Biol.*, vol. 7(2), pp. 108-113 (2000).

Lim, et al., "Studies of Reaction Kinetics in Relation to the $T_g$ of Polymers in Frozen Model Systems," in Levine, eds., *Water Relationships in Food*, New York: Plenum Press, pp. 103-122 (1991).

Boctor, et al., "Enhancement of the Stability of Thrombin by Polyols: Microcalorimetric Studies," *J. Pharm. Pharmacol.*, vol. 44, pp. 600-603 (1992).

Lozano, et al., "Influence of Polyhydroxylic Cosolvents on Papain Thermostability," *Enzyme Microbiol. Technol.*, vol. 15, pp. 868-873 (1993).

Lozano, et al., "Effect of Polyols on α-Chymotrypsin Thermostability: A Mechanistic Analysis of the Enzyme Stabilization," *J. Biotechnol.*, vol. 35, pp. 9-18 (1994).

Rossi, et al., "Stabilization of the Restriction Enzyme EcoRI Dried with Trehalose and Other Selected Glass-Forming Solutes," *Biotechnol. Prog.*, vol. 13, pp. 609-616 (1997).

Schebor, et al., "Glassy State and Thermal Inactivation of Invertase and Lactase in Dried Amorphous Matrices," *Biotechnol. Prog.*, vol. 13, pp. 857-863 (1997).

Golovan, et al., Characterization and Overproduction of the *E. coli* appA Encoded Biofunctional Enzyme that Exhibits Both Phytase and Acid Phosphatase Activities, Can. J. Microbiol., vol. 46, pp. 59-71 (2000).

Ralf Greiner et al., "Purification and Characterization of a Phytase from *Klebsiella terrigena*", *Archives of Biochemistry and Biophysics*, vol. 341, No. 2, pp. 201-206, ( May 15, 1997).

Abul H.J. Ulah, "*Aspergillus Ficuum* Phytase: Partial Primary Structure, Substrate Selectivity, and Kinetic Characterization", *Preparative Biochemistry*, 18(4), pp. 459-471, (1988).

Opposition Brief DSM Nutritional Products (10 pages).

Opposition Brief Opposition by Novozymes A/S (18 Pages).

ATCC Catalog for Yeasts, 19th Edition (1995).

Belin et al., "A Pleiotropic Acid Phosphatase-Deficient Mutant of *Escherichia coli* Shows Premature Termination in the *dsbA* Gene. Use of *dsbA::phoA* fusions to Localize a Structurally Important Domain in DsbA," *Mol. Gen. Genet.* 242:23-32 (1994).

Genbank Accession No. AAB96872 (Jan. 16, 1998).

Genbank Accession No. M94550 (Apr. 27, 1993).

Genbank Accession No. P34752 (Jan. 25, 2005).

Kostrewa et al., "Crystal Structure of *Aspergillus niger* pH 2.5 Acid Phosphatase at 2.4 Å Resolution," *J. Mol. Biol.* 288:965-974 (1999).

Kostrewa et al., "Crystal Structure of Phytase from *Aspergillus ficuum* at 2.5 Å Resolution," *Nat. Struct. Biol.* 4:185-190 (1997).

Lehmann et al., "Exchanging the Active Site Between Phytases for Altering the Functional Properties of the Enzyme," *Protein Sci.* 9(10):1866-1872 (2000).

Lehmann et al., "From DNA Sequence to Improved Functionality: Using Protein Sequence Comparisons to Rapidly Design a Thermostable Consensus Phytase," *Protein Eng.* 13(1):49-57 (2000).

Lei et al., "Calcium Level Affects the Efficacy of Supplemental Microbial Phytase in Corn-Soybean Meal Diets of Weanling Pigs," *J. Anim. Sci.* 72(1):139-143 (1994).

Lei et al., "Supplemental Microbial Phytase Improves Bioavailability of Dietary Zinc to Weanling Pigs," *J. Nutr.* 123:1117-1123 (1993).

Lei et al., "Supplementing Corn-Soybean Meal Diets with Microbial Phytase Linearly Improves Phosphorus Utilization by Weanling Pigs," *J. Anim. Sci.* 71:3359-3367 (1993).

Mitchell et al., "The Phytase Subfamily of Histidine Acid Phosphatases: Isolation of genes for Two Novel Phytases from the Fungi *Aspergillus terreus* and *Myceliophthora thermophila*," *Microbiol.* 143:245-252 (1997).

Mullaney et al., "Advances in Phytase Research," *Adv. Appl. Microbiol.* 47:157-199 (2000).

Mullaney et al., "Phytase Astivity in *Aspergillus fumigatus* Isolates," *Biochem. Biophys. Res. Commun.* 275:759-763 (2000).

Mullaney et al., "Positive Identification of a Lambda gt11 Clone Containing a Region of Fungal Phytase Gene by Immunoprobe and Sequence Verfication," *Appl. Microbiol. Biotechnol.* 35:611-614 (1991).

Mullaney et al., "Site-Directed Mutagenesis of *Aspergillus niger* NRRL 3135 Phytase at Reidue 300 to Enhance Catalysis at pH 4.0," *Biochem. Biophys. Res. Commun.* 297(4):1016-1020 (2000).

Nielsen et al., "The Determinants of α-Amylase pH-Activity Profiles," *Protein Eng.* 14(7):505-512 (2001).

Pasamontes et al., "Gene Cloning, Purification, and Characterization of a Heat-Stable Phytase from the Fungus *Aspergillus fumigatus*," *Appl. Environ. Microbiol.* 63(5): 1696-1700 (1997).

Rodriguez et al., "Expression of the *Aspergillus fumigatus* Phytase gene in *Pichia pastoris* and Characterization of the Recombinant Enzyme," *Biochem. Biophys. Res. Commun.* 268:373-378 (2000).

Tomschy et al., "Active Site Residue 297 of *Aspergillus niger* Phytase Critically Affects the Catalytic Properties," *FEBS Lett.* 472(2-3):169-172 (2000).

Tomschy et al., "Engineering of Phytase for Improved Activity at Low pH," *Appl. Environ. Microbiol.* 68(4):1907-1913 (2002).

Tomschy et al., "Optimization of the Catalytic Properties of *Aspergillus fumigatus* Phytase Based on the Three-Dimensional Structure," *Protein Sci.* 9(7):1304-1311 (2000).

Ullah et al., "Cyclohexanedione Modification of Arginine at the Active Site of *Aspergillus ficuum* Phytase," *Biochem. Biophys. Res. Commun.* 178(1):45-53 (1991).

Ullah et al., "Extracurriculas Phytase (E.C. 3.1.3.8) from *Aspergillus ficuum* NRRL 3135: Purification and Characterization," *Prep. Biochem.* 17(1):63-91 (1987).

Van Dijck, P.W.M., "Chymosin and Phytase. Made by Genetic Engineering (No. 10 in a Series of Articles to Promote a Better Understanding of the Use of Genetic Engineering)," *J. BIotechnol.* 67:77-80 (1999).

Van Etten et al., "Covalent Structure, Disulfide Bonding, and Identification of Reactive Surface and Active Site Residues of Human Prostatic Acid Phosphatase," *J. Biol. Chem.* 266(4):2313-2319 (1991).

Yi et al., "Sites of Phytase Activity in the Gastrointestinal Tract of Young Pigs," *Anim. feed Sci. Technol.* 61:361-368 (1996).

Ullah et al., "Differences in the Active Site Environment of *Aspergillus ficuum* Phytases," *Biochemical and Biophysical Research Communications* 243, 458-462 (1998).

```
        Pf1
  1 taaggagcagaaaca ATG TGG TAT TTC CTT TGG TTC GTC GGC ATT TTG TTG ATG TGT TCG CTC  63
  1                 M   W   Y   F   L   W   F   V   G   I   L   L   M   C   S   L    16

64 TCC ACC CTT GTG TTG GTA TGG CTG GAC CCG CGA TTG AAA AGT TAAcgaacgtaagcctgatccgg 128
 17  S   T   L   V   L   V   W   L   D   P   R   L   K   S   *                      31

129 cgcattagcgtcgatcaggcaataatatcggatatcaaagcggacacatatcg ATG AAA GCG ATC TTA ATC    201
  1                                                      M   K   A   I   L   I       6

E2
202 CCA TTT TTA TCT CTT TTG ATT CCG TTA ACC CCG CAA TCT GCA TTC GCT CAG AGT GAG CCG  261
  7  P   F   L   S   L   L   I   P   L   T   P   Q   S   A   F   A   Q   S   E   P   26

262 GAG CTG AAG CTG GAA AGT GTG GTG ATT GTC AGC CGT CAT GGT GTG CGT GCC CCA ACC AAG  321
 27  E   L   K   L   E   S   V   V   I   V   S   R   H   G   V   R   A   P   T   K   46

322 GCC ACG CAA CTG ATG CAG GAT GTC ACC CCA GAC GCA TGG CCA ACC TGG CCG GTA AAA CTG  381
 47  A   T   Q   L   M   Q   D   V   T   P   D   A   W   P   T   W   P   V   K   L   66

382 GGT TGG CTG ACA CCA CGC GGT GGT GAG CTA ATC GCC TAT CTC GGA CAT TAC CAA CGC CAG  441
 67  G   W   L   T   P   R   G   G   E   L   I   A   Y   L   G   H   Y   Q   R   Q   86

442 CGT CTG GTG GCC GAC GGA TTG CTG GCG AAA AAG GGC TGC CCG CAG CCT GGT CAG GTC GCG  501
 87  R   L   V   A   D   G   L   L   A   K   K   G   C   P   Q   P   G   Q   V   A  106

502 ATT ATT GCT GAT GTC GAC GAG CGT ACC CGT AAA ACA GGC GAA GCC TTC GCC GCG GGG CTG  561
107  I   I   A   D   V   D   E   R   T   R   K   T   G   E   A   F   A   A   G   L  126

562 GCA CCT GAC TGT GCA ATA ACC GTA CAT ACC CAG GCA GAT ACG TCC AGT CCC GAT CCG TTA  621
127  A   P   D   C   A   I   T   V   H   T   Q   A   D   T   S   S   P   D   P   L  146

622 TTT AAT CCT CTA AAA ACT GGC GTT TGC CAA CTG GAT AAC GCG AAC GTG ACT GAC GCG ATC  681
147  F   N   P   L   K   T   G   V   C   Q   L   D   N   A   N   V   T   D   A   I  166

682 CTC AGC AGG GCA GGA GGG TCA ATT GCT GAC TTT ACC GGG CAT CGG CAA ACG GTG TTT CGC  741
167  L   S   R   A   G   G   S   I   A   D   F   T   G   H   R   Q   T   V   F   R  186

742 GAA CTG GAA CGG GTG CTT AAT TTT TCC CAA TTA AAC TTG TGC CTT AAC CGT GAG AAA CAG  801
187  E   L   E   R   V   L   N   F   S   Q   L   N   L   C   L   N   R   E   K   Q  206

802 GAC GAA AGC TGT TCA TTA ACG CAG GCA TTA CCA TCG GAA CTC AAG GTG AGC GCC GAC AAT  861
207  D   E   S   C   S   L   T   Q   A   L   P   S   E   L   K   V   S   A   D   N  226

862 GTT TCA TTA ACC GGT GCG GTA AGC CTC GCA TCA ATG CTG ACG GAA ATA TTT CTC CTG CAA  921
227  V   S   L   T   G   A   V   S   L   A   S   M   L   T   E   I   F   L   L   Q  246

922 CAA GCA CAG GGA ATG CCG GAG CCG GGG TGG GGA AGG ATC ACT GAT TCA CAC CAG TGG AAC  981
247  Q   A   Q   G   M   P   E   P   G   W   G   R   I   T   D   S   H   Q   W   N  266

982 ACC TTG CTA AGT TTG CAT AAC GCG CAA TTT TAT TTA CTA CAA CGC ACG CCA GAG GTT GCC 1041
267  T   L   L   S   L   H   N   A   Q   F   Y   L   L   Q   R   T   P   E   V   A  286

1042 CGC AGT CGC GCC ACC CCG TTA TTG GAT TTG ATC ATG GCA GCG TTG ACG CCC CAT CCA CCG 1101
287   R   S   R   A   T   P   L   L   D   L   I   M   A   A   L   T   P   H   P   P  306

1102 CAA AAA CAG GCG TAT GGT GTG ACA TTA CCC ACT TCA GTG CTG TTT ATT GCC GGA CAC GAT 1161
307   Q   K   Q   A   Y   G   V   T   L   P   T   S   V   L   F   I   A   G   H   D  326

1162 ACT AAT CTG GCA AAT CTC GGC GGC GCA CTG GAG CTC AAC TGG ACG CTT CCA GGT CAG CCG 1221
327   T   N   L   A   N   L   G   G   A   L   E   L   N   W   T   L   P   G   Q   P  346

1222 GAT AAC ACG CCG CCA GGT GGT GAA CTG GTG TTT GAA CGC TGG CGT CGG CTA AGC GAT AAC 1281
347   D   N   T   P   P   G   G   E   L   V   F   E   R   W   R   R   L   S   D   N  366

1282 AGC CAG TGG ATT CAG GTT TCG CTG GTC TTC CAG ACT TTA CAG CAG ATG CGT GAT AAA ACG 1341
367   S   Q   W   I   Q   V   S   L   V   F   Q   T   L   Q   Q   M   R   D   K   T  386

1342 CCG CTA TCA TTA AAT ACG CCG CCC GGA GAG GTG AAA CTG ACC CTG GCA GGA TGT GAA GAG 1401
387   P   L   S   L   N   T   P   P   G   E   V   K   L   T   L   A   G   C   E   E  406

1402 CGA AAT GCG CAG GGC ATG TGT TCG TTG GCC GGT TTT ACG CAA ATC GTG AAT GAA GCG CGC 1461
407   R   N   A   Q   G   M   C   S   L   A   G   F   T   Q   I   V   N   E   A   R  426

K2
1462 ATA CCG GCG TGC AGT TTG TAA TGGTACCCC                                            1491
427   I   P   A   C   S   L   *                                                       433
```

FIG. 1

Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
            35                  40                  45

Gln Leu Met Gln Asp Val Thr Pro Asp Ala Trp Pro Thr Trp Pro Val
        50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
            85                  90                  95

Lys Gly Cys Pro Gln Pro Gly Gln Val Ala Ile Ile Ala Asp Val Asp
            100                 105                 110

Glu Arg Thr Arg Lys Thr Gly Glu Ala Phe Ala Ala Gly Leu Ala Pro
            115                 120                 125

Asp Cys Ala Ile Thr Val His Thr Gln Ala Asp Thr Ser Ser Pro Asp
        130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
            165                 170                 175

Phe Thr Gly His Arg Gln Thr Ala Phe Arg Glu Leu Glu Arg Val Leu
            180                 185                 190

Asn Phe Pro Gln Ser Asn Leu Asn Leu Lys Arg Glu Lys Gln Asn Glu
        195                 200                 205

FIG. 2A

```
Ser Cys Asn Leu Thr Gln Ala Leu Pro Ser Glu Leu Lys Val Ser Ala
    210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
            275                 280                 285

Arg Ala Thr Pro Leu Leu Asp Leu Ile Lys Thr Ala Leu Thr Pro His
        290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Arg Leu Ser Asp Asn Ser Gln
            355                 360                 365

Trp Ile Gln Val Ser Leu Val Phe Gln Thr Leu Gln Gln Met Arg Asp
            370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
            420                 425                 430

FIG. 2B
```

```
1    taa gga gca gaa aca ATG TGG TAT TTA CTT TGG TTC GTC GGC ATT
46   TTG TTG ATG TGT TCG CTC TCC ACC CTT GTG TTG GTA TGG CTG GAC
91   CCG CGA TTG AAA AGT T aac gaa cgt agg cct gat gcg gcg cat
134  tag cat cgc atc agg caa tca ata atg tca gat atg aaa agc gga
179  aac ata tcg ATG AAA GCG ATC TTA ATC CCA TTT TTA TCT CTT CTG
224  ATT CCG TTA ACC CCG CAA TCT GCA TTC GCT CAG AGT GAG CCG GAG
269  CTG AAG CTG GAA AGT GTG GTG ATT GTC AGC CGT CAT GGT GTG CGT
314  GCC CCA ACC AAG GCC ACG CAA CTG ATG CAG GAT GTC ACC CCA GAC
359  GCA TGG CCA ACC TGG CCG GTA AAA CTG GGT TGG CTG ACA CCA CGC
404  GGT GGT GAG CTA ATC GCC TAT CTC GGA CAT TAC CAA CGC CAG CGT
449  CTG GTG GCC GAC GGA TTG CTG GCG AAA AAG GGC TGC CCG CAG CCT
494  GGT CAG GTC GCG ATT ATT GTC GAT GTC GAC GAG CGT ACC CGT AAA
539  ACA GGC GAA GCC TTC GCC GCC GGG CTG GCA CCT GAC TGT GCA ATA
584  ACC GTA CAT ACC CAG GCA GAT ACG TCC AGT CCC GAT CCG TTA TTT
629  ATT CCT CTA AAA ACT GGC GTT TGC CAA CTG GAT AAC GCG AAC GTG
674  ACT GAC GCG ATC CTC AGC AGG GCA GGA GGG TCA ATT GCT GAC TTT
719  ACC GGG CAT CGG CAA ACG GCG TTT CGC GAA CTG AAA CGG GTG CTT
764  AAT TTT CCG CAA TCA AAC TTG AAC CTT AAA CGT GAG AAA CAG AAT
809  GAA AGC TGT AAC TTA ACG CAC GCA TTA CCA TCG AAC TC AAG GTG
854  ACC GCC GAC AAT GTT TCA TTA ACC GGT GCG GTA AGC CTC GCA TCA
899  ATG CTG ACG GAA ATA TTT CTC CTG CAA CAA GCA CAG GGA ATG CCG
944  GAG CCG GGG TGG GGA AGG ATC ACT GAT TCA CAC CAG TGG AAC ACC
989  TTG CTA AGT TTG CAT AAC GCG CAA TTT TAT TTA CTA CAA CGC ACG
```

FIG. 2C

```
1034 CCA GAG GTT GCC CGC AGT CGC GCC ACC CCG TTA TTG GAT TTG ATC

1079 AAG ACA GCG TTG ACG CCC CAT CCA CCG CAA AAA CAG GCG TAT GGT

1124 GTG ACA TTA CCC ACT TCA GTG CTG TTT ATT GCC GCA CAC GAT ACT

1169 AAT CTG GCA AAT CTC GGC GGC GCA CTG GAG CTC AAC TGG ACG CTT

1214 CCA GGT CAG CCG GAT AAC ACG CCG CCA GGT GGT GAA CTG GTG TTT

1259 GAA CGC TGG CGT CGG CTA AGC GAT AAC AGC CAG TGG ATT CAG GTT

1304 TCG CTG GTC TTC CAG ACT TTA CAG CAG ATG CGT GAT AAA ACG CCG

1349 CTA TCA TTA AAT ACG CCG CCC GGA GAG GTG AAA CTG ACC CTG GCA

1394 GGA TGT GAA GAG CGA AAT GCG CAG GGC ATG TGT TCG TTG GCC GGT

1439 TTT ACG CAA ATC GTG AAT GAA GCG CGC ATA CCG GCG TGC AGT TTG

1484 TAA
```

FIG. 2D

PHYTASE-CONTAINING ANIMAL FOOD AND METHOD

CROSS REFERENCE TO RELATED APPLICATIONS

This application claims priority under 35 U.S.C § 119(e) to U.S. Provisional Application Ser. No. 60/335,303, filed on Oct. 31, 2001.

FIELD OF THE INVENTION

The present invention is related to a method of improving the nutritional value of a foodstuff and to an improved foodstuff. More particularly, the invention relates to a method of improving the nutritional value of a foodstuff comprising myo-inositol hexakisphosphate by feeding the foodstuff to an animal in combination with a phytase expressed in yeast.

BACKGROUND AND SUMMARY OF THE INVENTION

Phytases are myo-inositol hexakisphosphate phosphohydrolases that catalyze the stepwise removal of inorganic orthophosphate from phytate (myo-inositol hexakisphosphate). Phytate is the major storage form of phosphate in plant feeds, including cereals and legumes. Because monogastric animals such as pigs, poultry, and humans have little phytase in their gastrointestinal tracts nearly all of the ingested phytate phosphate is indigestible. Accordingly, these animals require supplementation of their diets with phytase or inorganic phosphate. In contrast, ruminants have microorganisms in the rumen that produce phytases and these animals do not require phytase supplementation of their diets.

The unutilized phytate phosphate in monogastric animals creates additional problems. The unutilized phytate phosphate is excreted in manure and pollutes the environment. Furthermore, in monogastric animals phytate passes largely intact through the upper gastrointestinal tract where it chelates essential minerals (e.g., calcium and zinc), binds amino acids and proteins, and inhibits enzyme activities. Accordingly, phytase supplementation of the diets of monogastric animals not only decreases requirements for supplementation with inorganic phosphate, but also reduces pollution of the environment caused by phytate, diminishes the antinutritional effects of phytate, and increases the nutritional value of the feed.

There are two types of phytases including a 3-phytase (EC.3.1.3.8) which removes phosphate groups at the 1 and 3 positions of the myo-inositol ring, and a 6-phytase (EC.3.1.3.6) which first frees the phosphate at the 6-position of the ring. Plants usually contain 6-phytases and a broad range of microorganisms, including bacteria, filamentous fungi, and yeasts, produce 3-phytases. Two phytases, phyA and phyB from *Aspergillus niger*, have been cloned and sequenced. PhyA has been expressed in *Aspergillus niger* and the recombinant enzyme is available commercially for use in supplementing animal diets.

Phytase genes have also been isolated from *Aspergillus terreus, Myceliophthora thermophila, Aspergillus fumigatus, Emericella nidulans, Talaromyces thermophilus, Escherichia coli* (appA), and maize. Additionally, phytase enzymes have been isolated and/or purified from *Bacillus* sp., *Enterobacter* sp., *Klebsiella terrigena*, and *Aspergillus ficum*.

The high cost of phytase production has restricted the use of phytase in the livestock industry as phytase supplements are generally more expensive than the less environmentally desirable inorganic phosphorous supplements. The cost of phytase can be reduced by enhancing production efficiency and/or producing an enzyme with superior activity.

Yeast expression systems can be used to effectively produce enzymes, in part, because yeast are grown in simple and inexpensive media. Additionally, with a proper signal sequence, the expressed enzyme can be secreted into the culture medium for convenient isolation and purification. Some yeast expression systems are also accepted in the food industry as being safe for the production of food products unlike fungal expression systems which may in some cases be unsafe, for example, for human food manufacturing.

Thus, one aspect of this invention is a method of improving the nutritional value of a foodstuff by supplementing the foodstuff with a yeast-expressed phytase with superior capacity to release phosphate from phytate in foodstuffs. The invention is also directed to a foodstuff with improved nutritional value comprising the yeast-expressed phytase. The phytase can be efficiently and inexpensively produced because the yeast-expressed phytase of the present invention is suitable for commercial use in the feed and food industries with minimal processing.

In one embodiment, a method is provided of improving the nutritional value of a foodstuff consumed by a monogastric animal by increasing the bioavailability of phosphate from phytate wherein the foodstuff comprises myo-inositol hexakisphosphate. The method comprises the step of feeding to the animal the foodstuff in combination with less than 1200 units of a phytase expressed in yeast per kilogram of the foodstuff, wherein the phytase is *Escherichia coli*-derived AppA2, and wherein the bioavailability of phosphate from phytate is increased by at least 2-fold compared to the bioavailability of phosphate from phytate obtained by feeding the foodstuff in combination with the same units of a phytase expressed in a non-yeast host cell.

In another embodiment, a method is provided of reducing the feed to weight gain ratio of a monogastric animal by feeding the animal a foodstuff wherein the foodstuff comprises myo-inositol hexakisphosphate. The method comprises the step of feeding to the animal the foodstuff in combination with a phytase expressed in yeast, wherein the phytase is selected from the group consisting of *Escherichia coli*-derived AppA2 and a site-directed mutant of *Escherichia coli*-derived AppA, and wherein the feed to weight gain ratio of the animal is reduced.

In an alternate embodiment, a method of improving the nutritional value of a foodstuff consumed by a monogastric animal by increasing the bone mass and mineral content of the animal wherein the foodstuff comprises myo-inositol hexakisphosphate. The method comprises the step of feeding to the animal the foodstuff in combination with a phytase expressed in yeast wherein the phytase is selected from the group consisting of *Escherichia coli*-derived AppA2 and a site-directed mutant of *Escherichia coli*-derived AppA, and wherein the bone mass and mineral content of the animal is increased.

In yet another embodiment, a feed additive composition for addition to an animal feed is provided. The feed additive composition comprises a yeast-expressed phytase and a carrier for the phytase wherein the concentration of the phytase in the feed additive composition is greater than the concentration of the phytase in the final feed mixture.

In still another embodiment, a foodstuff is provided. The foodstuff comprises the above-described feed additive composition wherein the concentration of the phytase in the final feed mixture is less than 1200 units of the phytase per kilogram of the final feed mixture.

In another embodiment, a method is provided of improving the nutritional value of a foodstuff consumed by a monogastric animal wherein the foodstuff comprises myo-inositol hexakisphosphate. The method comprises the steps of spray drying a phytase selected from the group consisting of *Escherichia coli*-derived AppA2 and a site-directed mutant of *Escherichia coli*-derived AppA, mixing the phytase with a carrier for the phytase and, optionally, other ingredients to produce a feed additive composition for supplementing a foodstuff with the phytase, mixing the feed additive composition with the foodstuff, and feeding the animal the foodstuff supplemented with the feed additive composition.

In an alternate embodiment, a method is provided of improving the nutritional value of a foodstuff consumed by an avian species by increasing the bioavailability of phosphate from phytate wherein the foodstuff comprises myo-inositol hexakisphosphate. The method comprises the step of feeding to the avian species the foodstuff in combination with less than 1200 units of a phytase expressed in yeast per kilogram of the foodstuff, wherein the bioavailability of phosphate from phytate is increased by at least 1.5-fold compared to the bioavailability of phosphate from phytate obtained by feeding to a non-avian species the foodstuff in combination with the phytase expressed in yeast.

In yet another embodiment, a method is provided of reducing the feed to weight gain ratio of an avian species by feeding the avian species a foodstuff wherein the foodstuff comprises myo-inositol hexakisphosphate. The method comprises the step of feeding to the avian species the foodstuff in combination with a phytase expressed in yeast wherein the feed to weight gain ratio of the animal is reduced.

In still another embodiment, a method is provided of improving the nutritional value of a foodstuff consumed by an avian species by increasing the bone mass and mineral content of the avian species wherein the foodstuff comprises myo-inositol hexakisphosphate. The method comprises the step of feeding to the avian species the foodstuff in combination with a phytase expressed in yeast wherein the bone mass and mineral content of the avian species is increased.

In another embodiment, a method is provided of improving the nutritional value of a foodstuff consumed by an avian species wherein the foodstuff comprises myo-inositol hexakisphosphate. The method comprises the step of feeding to the avian species the foodstuff in combination with a phytase expressed in yeast wherein the number of eggs laid and the weight of the eggs laid by the avian species is increased.

BRIEF DESCRIPTION OF THE DRAWINGS

FIG. 1 shows the amino acid and nucleotide sequences of AppA2.

FIG. 2 shows the amino acid and nucleotide sequences of Mutant U.

DETAILED DESCRIPTION OF THE INVENTION

Figure 3:
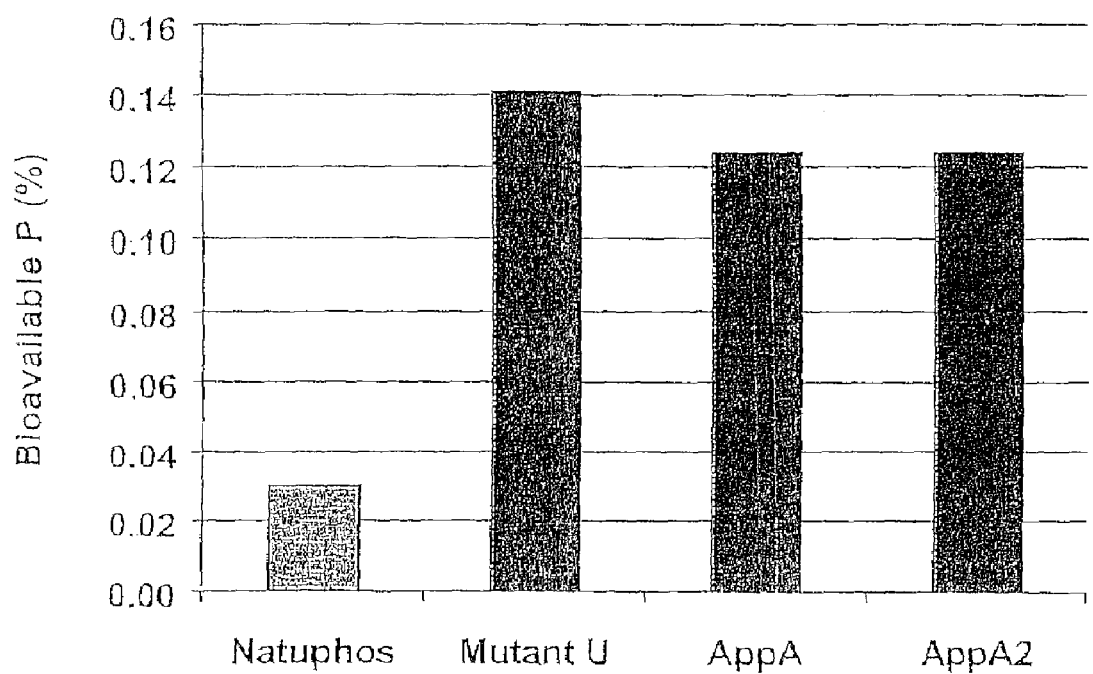
FIG. 3 shows the percent increase in bioavailable phosphate in vivo in chickens fed an animal feed supplemented with Natuphos®, Mutant U, AppA or AppA2.

The present invention provides a method of improving the nutritional value of a foodstuff consumed by an animal wherein the foodstuff comprises myo-inositol hexakisphosphate, the substrate for the phytase enzymes of the invention. The method comprises the step of feeding to an animal the foodstuff in combination with a phytase expressed in yeast wherein the bioavailability of phosphate from phytate is increased, the feed to weight gain ratio is reduced, the bone mass and mineral content of the animal is increased or, for avian species, additionally the egg weight or number of eggs laid is increased. The phytase can be selected from the group consisting of *Escherichia coli*-derived AppA2 and a site-directed mutant of *Escherichia coli* derived-AppA. In an alternative embodiment, for avian species, the phytase can be any phytase, including phytases selected from the group consisting of *Escherichia coli*-derived AppA, *Escherichia coli*-derived AppA2, and a site-directed mutant of *Escherichia coli*-derived AppA. In some embodiments, the bioavailability of phosphate from phytate, the feed to weight gain ratio, and bone mass and mineral content are improved by at least 2-fold, for example, in an avian species, such as poultry, compared to the improvement in nutritional value obtained by feeding the foodstuff in combination with the same weight percent of a phytase expressed in a non-yeast host cell. The bioavailability of phosphate from phytate is also increased by at least 1.5-fold in porcine species compared to the improvement in nutritional value obtained by feeding the foodstuff in combination with the same weight percent of a phytase expressed in a non-yeast host cell. Additionally, the bioavailability of phosphate from phytate and the bone mass and mineral content obtained by feeding an avian species the foodstuff in combination with the phytase expressed in yeast is increased by at least 1.5-fold compared to the bioavailability of phosphate from phytate and the bone mass and mineral content obtained by feeding a non-avian species the foodstuff in combination with the yeast-expressed phytase.

As used herein "improving nutritional value" or "increased nutritional value" means an improvement in the nutritional value of a foodstuff as reflected by an increase in the bioavailability of phosphate from phytate, a reduction in the feed to weight gain ratio, an increase in bone mass and mineral content, an increase in the bioavailability of inositol from phytate, an increase in the bioavailability from phytate of minerals such as magnesium, manganese, calcium, iron and zinc in an animal fed the foodstuff, or an increase in egg weight or number of eggs laid for an avian species fed the foodstuff (e.g., for laying hens in the first or subsequent round of laying eggs).

As used herein an increase in the "bioavailability of phosphate from phytate" means an increase in availability of phosphate from phytate as reflected by an increase in weight gain or bone ash weight.

As used herein the term "non-yeast host cell" includes a fungal cell.

As used herein, the term "phytase" means an enzyme capable of catalyzing the removal of inorganic phosphate from myo-inositol hexakisphosphate.

As used herein, the term "phytate" means a composition comprising myo-inositol hexakisphosphate.

In accordance with the invention, the feed to weight gain ratio is calculated by dividing weight gain by feed intake. An increase in bone mass or mineral content is reflected by an increase in the dry weight of tibia or fibula bones or by an increase in ash weight.

A variety of phytase genes may be expressed to produce phytase for use in accordance with the invention. Exemplary of genes that can be used in accordance with the invention are phytase genes derived from bacteria, filamentous fungi, plants, and yeast, such as the appA (Gene Bank accession number M58708) and appA2 (Gene Bank accession number 250016) genes derived from *Escherichia coli* (*E. coli*) and the phyA and phyB genes derived from the fungus *Aspergillus niger*, or any site-directed mutant of these genes that retains or has improved myo-inositol hexakisphosphate phosphohydrolase activity.

Phytase genes can be obtained from isolated microorganisms, such as bacteria, fungus, or yeast, that exhibit particularly high phytase activity. As described below, the appA2 gene was cloned from such an *E. coli* isolate, and it is exemplary of such a phytase gene.

The expressed phytase gene can be a heterologous gene, or can be a homologous gene. A heterologous gene is defined herein as a gene originating from a different species than the species used for expression of the gene. For example, in the case of expression of a heterologous phytase gene, a phytase gene derived from *E. coli* or another species of bacteria can be expressed in a yeast species such as *Saccharomyces cerevisiae* or *Pichia pastoris*. A homologous gene is described herein as a gene originating from the same species used for expression of the gene. In the case of expression of a homologous phytase gene, a phytase gene derived from *Saccharomyces cerevisiae* can be expressed, for example, in the same yeast species.

Exemplary genes for use in producing phytase for use in accordance with the invention are appA, appA2, and site-directed mutants of appA or appA2. Substituted, deleted, and truncated phytase genes, wherein the resulting expressed phytase, or a fragment thereof, retains substantially the same phytase activity as the phytases specifically exemplified herein, are considered equivalents of the exemplified phytase genes and are within the scope of the present invention.

The appA gene was isolated from *E. coli* (see U.S. Pat. No. 6,451,572, incorporated herein by reference). The appA2 gene was isolated from a bacterial colony that exhibited particularly high phytase activity obtained from the colon contents of crossbred Hampshire-Yorkshire-Duroc pigs (see U.S. patent application Ser. No. 09/540,149, incorporated herein by reference). The AppA2 protein product exhibits a pH optimum between about 2.5 and about 3.5. The amino acid sequence of AppA2 is as shown in SEQ ID Nos.: 2, 3, and 10. FIG. 1 shows the amino acid and nucleotide sequences of AppA2. The untranslated region is indicated by lowercase letters. The underlined sequences are the primers used to amplify appA2 (Pfl: 1-22, and K2: 1468-1490), appA2 (E2: 243-252, and K2: 1468-1490). Potential N-glycosylation sites are boxed. The sequence of appA2 has been transmitted to Genebank data library with accession number 250016. The nucleotide sequence of AppA2 is as shown in SEQ ID No.: 1.

Several site-directed mutants of appA have been isolated (see PCT Publication No. WO 01/36607 A1 (U.S. patent application Ser. No. 60/166,179, incorporated herein by reference)). These mutants were designed to enhance glycosylation of the AppA enzyme. The mutants include A131N/V134N/D207N/S211N, C200N/D207N/S211N (Mutant U), and A131N/V134N/C200N/D207N/S211N (see Rodriguez et al., *Arch. of Biochem. and Biophys.* 382: 105-112 (2000), incorporated herein by reference). Mutant U has a higher specific activity than AppA, and, like AppA2, has a pH optimum of between about 2.5 and about 3.5. The C200N mutation in Mutant U is in a gapped region and C200 is involved with C210 in forming a unique disulfide bond in AppA. FIG. 2 shows the amino acid and nucleotide sequences of Mutant U. The amino acid sequence of Mutant U is shown in SEQ ID No.: 5, and the nucleotide sequence of Mutant U is shown in SEQ ID No.: 4.

Any yeast expression system or other eukaryotic expression system known to those skilled in the art can be used in accordance with the present invention. For example, various yeast expression systems are described in U.S. patent application Ser. No. 09/104,769 (now U.S. Pat. No. 6,451,572), U.S. patent application Ser. No. 09/540,149, and in U.S. patent application Ser. No. 60/166,179 (PCT Publication No. WO 01/36607 A1), all incorporated herein by reference. Any of these yeast expression systems can be used. Alternatively, other eukaryotic expression systems can be used such as an insect cell expression system (e.g., Sf9 cells), a fungal cell expression system (e.g., *Trichoderma*), or a mammalian cell expression system.

A yeast expression system can be used to produce a sufficient amount of the phytase being secreted from the yeast cells so that the phytase can be conveniently isolated and purified from the culture medium. Secretion into the culture medium is controlled by a signal peptide (e.g., the phyA signal peptide or yeast α-factor signal peptide) capable of directing the expressed phytase out of the yeast cell. Other signal peptides suitable for facilitating secretion of the phytase from yeast cells are known to those skilled in the art. The signal peptide is typically cleaved from the phytase after secretion.

If a yeast expression system is used, any yeast species suitable for expression of a phytase gene can be used including such yeast species as *Saccharomyces* species (e.g., *Saccharomyces cerevisiae*), *Kluyveromyces* species, *Torulaspora* species, *Schizosaccharomyces* species, and methylotrophic yeast species such as *Pichia* species (e.g., *Pichia pastoris*), *Hansenula* species, *Torulopsis* species, *Candida* species, and *Karwinskia* species. In one embodiment the phytase gene is expressed in the methylotrophic yeast *Pichia pastoris*. Methylotrophic yeast are capable of utilizing methanol as a sole carbon source for the production of the energy resources necessary to maintain cellular function, and contain a gene encoding alcohol oxidase for methanol utilization.

Any host-vector system known to the skilled artisan (e.g., a system wherein the vector replicates autonomously or integrates into the host genome) and compatible with yeast or another eukaryotic cell expression system can be used. In one embodiment, the vector has restriction endonuclease cleavage sites for the insertion of DNA fragments, and genetic markers for selection of transformants. The phytase gene can be functionally linked to a promoter capable of directing the expression of the phytase, for example, in yeast, and, in one embodiment, the phytase gene is spliced in frame with a transcriptional enhancer element and has a terminator sequence for transcription termination (e.g., HSP150 terminator). The promoter can be a constitutive (e.g., the 3-phospho-glycerate kinase promoter or the α-factor promoter) or an inducible promoter (e.g., the ADH2, GAL-1-10, GAL 7, PHO5, T7, or metallothionine promoter). Various host-vector systems are described in U.S. patent application Ser. No. 09/104,769 (now U.S. Pat. No. 6,451,572), U.S. patent application Ser. No. 09/540,149, and in U.S. patent application Ser. No. 60/166,179 (PCT Publication No. WO 01/36607 A1), all incorporated herein by reference.

Yeast cells are transformed with a gene-vector construct comprising a phytase gene operatively coupled to a yeast expression system using procedures known to those skilled in the art. Such transformation protocols include electroporation and protoplast transformation.

The transformed yeast cells may be grown by a variety of techniques including batch and continuous fermentation in a liquid medium or on a semi-solid medium. Culture media for yeast cells are known in the art and are typically supplemented with a carbon source (e.g., glucose). The transformed yeast cells can be grown aerobically at 30° C. in a controlled pH environment (a pH of about 6) and with the carbon source (e.g., glucose) maintained continuously at a predetermined level known to support growth of the yeast cells to a desired density within a specific period of time.

The yeast-expressed phytase for use in accordance with the method of the present invention can be produced in purified form by conventional techniques (for example, at least about 60% pure, or at least about 70-80% pure). Typically, the phytase is secreted into the yeast culture medium and is collected from the culture medium. For purification from the culture medium the phytase can, for example, be subjected to ammonium sulfate precipitation followed by DEAE-Sepharose column chromatography. Other conventional techniques known to those skilled in the art can be used such as gel filtration, ion exchange chromatography, DEAE-Sepharose column chromatography, affinity chromatography, solvent-solvent extraction, ultrafiltration, and HPLC. Alternatively, purification steps may not be required because the phytase may be present in such high concentrations in the culture medium that the phytase is essentially pure in the culture medium (e.g., 70-80% pure).

In cases where the phytase is not secreted into the culture medium, the yeast cells can be lysed, for example, by sonication, heat, or chemical treatment, and the homogenate centrifuged to remove cell debris. The supernatant can then be subjected to ammonium sulfate precipitation, and additional fractionation techniques as required, such as gel filtration, ion exchange chromatography, DEAE-Sepharose column chromatography, affinity chromatography, solvent-solvent extraction, ultrafiltration, and HPLC to purify the phytase. It should be understood that the purification methods described above for purification of phytases from the culture medium or from yeast cells are nonlimiting and any purification techniques known to those skilled in the art can be used to purify the yeast-expressed phytase if such techniques are required to obtain a substantially pure phytase.

In one embodiment, the phytase is collected from the culture medium without further purification steps by chilling the yeast culture (e.g., to about 8° C.) and removing the yeast cells using such techniques as centrifugation, microfiltration, and rotary vacuum filtration. The phytase in the cell-free medium can be concentrated by such techniques as, for example, ultrafiltration and tangential flow filtration.

Various formulations of the purified phytase preparation may be prepared. The phytase enzymes can be stabilized through the addition of other proteins (e.g., gelatin and skim milk powder), chemical agents (e.g., glycerol, polyethylene glycol, EDTA, potassium sorbate, sodium benzoate, and reducing agents and aldehydes), polysaccharides, monosaccharides, lipids (hydrogenated vegetable oils), sodium phytate, and other phytate-containing compounds, and the like. Phytase enzyme suspensions can also be dried (e.g., spray drying, drum drying, and lyophilization) and formulated as powders, granules, pills, mineral blocks, liquids, and gels through known processes. Gelling agents such as gelatin, alginate, collagen, agar, pectin and carrageenan can be used. The invention also extends to a feed innoculant preparation comprising lyophilized nonpathogenic yeast which can express the phytases of the present invention in the gastrointestinal tract of the animal when the animal is fed the preparation.

In one embodiment, the phytase in the cell-free culture medium is concentrated such as by ultrafiltration and spray drying of the ultrafiltration retentate. The spray dried powder can be blended directly with a foodstuff, or the spray dried powder can be blended with a carrier for use as a feed additive composition for supplementation of a foodstuff with phytase. In one embodiment, the phytase in the retentate is co-dried with a carrier and/or stabilizer. In another embodiment, the phytase is spray dried with an ingredient that helps the spray dried phytase to adhere to a carrier, or, alternatively, the phytase can loosely associate with the carrier. The feed additive composition (i.e., the phytase/carrier composition and, optionally, other ingredients) can be used for blending with the foodstuff to achieve more even distribution of the phytase in the foodstuff.

Exemplary feed additive compositions (i.e., phytase/carrier compositions and, optionally, other ingredients) can contain 600 units of phytase/gram of the carrier to 5000 units of phytase/gram of the carrier. These phytase/carrier compositions can contain additional ingredients. For example, the compositions can be formulated to contain rice hulls or wheat middlings as a carrier (25-80 weight percent), the phytase (0.5 to 20 weight percent), calcium carbonate (10 to 50 weight percent), and oils (1 to 3 weight percent). Alternatively, the feed additive composition can include the phytase and the carrier and no additional ingredients. The feed additive composition may be mixed with the feed to obtain a final feed mixture with from about 50 to about 2000 units of phytase/kilogram of the feed.

Thus, a foodstuff comprising a source of myo-inositol hexakisphosphate, a yeast-expressed phytase, and a carrier is also provided in accordance with the invention. Additionally, a method of improving the nutritional value of a foodstuff consumed by a monogastric animal wherein the foodstuff comprises myo-inositol hexakisphosphate is provided wherein the method comprises the steps of spray drying a phytase, including a phytase selected from the group consisting of *Escherichia coli*-derived AppA, *Escherichia coli*-derived AppA2, and a site-directed mutant of *Escherichia coli*-derived AppA, mixing the phytase with a carrier, and, optionally, other ingredients, to produce a feed additive composition for supplementing a foodstuff with the phytase, mixing the feed additive composition with the foodstuff, and feeding the animal the foodstuff supplemented with the feed additive composition.

In these embodiments, the carrier can be any suitable carrier for making a feed additive composition known in the art including, but not limited to, rice hulls, wheat middlings, a polysaccharide (e.g., specific starches), a monosaccharide, mineral oil, vegetable fat, hydrogenated lipids, calcium carbonate, gelatin, skim milk powder, phytate and other phytate-containing compounds, a base mix, and the like. A base mix typically comprises most of the ingredients, including vitamins and minerals, of a final feed mixture except for the feed blend (e.g., cornmeal and soybean meal). The phytase for use in the feed additive composition is preferably *E. coli*-derived AppA, *E. coli*-derived AppA2, or a site-directed mutant of *E. coli*-derived AppA.

The feed additive composition containing the spray dried phytase and a carrier and, optionally, other ingredients, is mixed with the final feed mixture to obtain a feed with a predetermined number of phytase units/kilogram of the feed (e.g., about 50 to about 2000 units phytase/kilogram of the feed). Before blending with the carrier, the spray dried phytase is assayed for phytase activity to determine the amount of dried powder to be blended with the carrier to obtain a feed additive composition with a predetermined number of phytase units/gram of the carrier. The phytase-containing carrier is then blended with the final feed mixture to obtain a final feed mixture with a predetermined number of phytase units/kilogram of the feed. Accordingly, the phytase concentration in the feed additive composition is greater than the phytase concentration in the final feed mixture.

In accordance with one embodiment of the invention the foodstuff is fed in combination with the yeast-expressed phytase to any monogastric animal (i.e., an animal having a stomach with a single compartment). Monogastric animals that can be fed a foodstuff in combination with a yeast-expressed phytase include agricultural animals, such as porcine species (e.g., barrows (i.e., castrated male pigs), gilts (i.e., female pigs prior to first mating) and any other type of swine), chickens, turkeys (poults (i.e., first several weeks post-hatching) and older animals), ducks, and pheasants, any other avian species, marine or fresh water aquatic species, animals held in captivity (e.g., zoo animals), or domestic animals (e.g., canine and feline).

Agricultural monogastric animals are typically fed animal feed compositions comprising plant products which contain phytate (e.g., cornmeal and soybean meal contain phytate (myo-inositol hexakisphosphate)) as the major storage form of phosphate, and, thus, it is advantageous to supplement the feed with phytase. Accordingly, the foodstuffs that can be supplemented with phytase in accordance with the invention include feed for agricultural animals such pig feed and poultry feed, and any foodstuff for avian species or marine or fresh water aquatic species (e.g., fish food). In addition, humans can be fed any foodstuff, such as a cereal product, containing phytate in combination with the yeast-expressed phytase of the present invention.

In the case of an animal feed fed to monogastric animals, any animal feed blend known in the art can be used in accordance with the present invention such as rapeseed meal, cottonseed meal, soybean meal, and cornmeal, but soybean meal and cornmeal are particularly preferred. The animal feed blend is supplemented with the yeast-expressed phytase, but other ingredients can optionally be added to the animal feed blend. Optional ingredients of the animal feed blend include sugars and complex carbohydrates such as both water-soluble and water-insoluble monosaccharides, disaccharides and polysaccharides. Optional amino acid ingredients that can be added to the feed blend are arginine, histidine, isoleucine, leucine, lysine, methionine, phenylalanine, threonine, tryptophan, valine, tyrosine ethyl HCl, alanine, aspartic acid, sodium glutamate, glycine, proline, serine, cysteine ethyl HCl, and analogs, and salts thereof. Vitamins that can be optionally added are thiamine HCl, riboflavin, pyridoxine HCl, niacin, niacinamide, inositol, choline chloride, calcium pantothenate, biotin, folic acid, ascorbic acid, and vitamins A, B, K, D, E, and the like. Minerals, protein ingredients, including protein obtained from meat meal or fish meal, liquid or powdered egg, fish solubles, whey protein concentrate, oils (e.g., soybean oil), cornstarch, calcium, inorganic phosphate, copper sulfate, salt, and limestone can also be added. Any medicament ingredients known in the art can be added to the animal feed blend such as antibiotics.

The feed compositions can also contain enzymes other than the yeast-expressed phytase. Exemplary of such enzymes are proteases, cellulases, xylanases, and acid phosphatases. For example, complete dephosphorylation of phytate may not be achieved by the phytase alone and addition of an acid phosphatase may result in additional phosphate release. A protease (e.g., pepsin) can be added, for example, to cleave the yeast-expressed phytase to enhance the activity of the phytase. Such a protease-treated phytase may exhibit enhanced capacity to increase the bioavailability of phosphate from phytate, to reduce the feed to weight gain ratio, to increase bone mass and mineral content, and to increase the egg weight or number of eggs laid for an avian species compared to intact yeast-expressed phytase. Additionally, combinations of phytases can be used, such as any combinations that may act synergistically to increase the bioavailability of phosphate from phytate, or proteolytic fragments of phytases or combinations of proteolytic fragments can be used. In this regard, the phytase gene expressed in yeast could be used to produce a truncated product directly for use in the method of the present invention.

Antioxidants can also be added to the foodstuff, such as an animal feed composition, to prevent oxidation of the phytase protein used to supplement the foodstuff. Oxidation can be prevented by the introduction of naturally-occurring antioxidants, such as beta-carotene, vitamin E, vitamin C, and tocopherol or of synthetic antioxidants such as butylated hydroxytoluene, butylated hydroxyanisole, tertiary-butylhydroquinone, propyl gallate or ethoxyquin to the foodstuff. Compounds which act synergistically with antioxidants can also be added such as ascorbic acid, citric acid, and phosphoric acid. The amount of antioxidants incorporated in this manner depends on requirements such as product formulation, shipping conditions, packaging methods, and desired shelf-life.

In accordance with one method of the present invention, the foodstuff, such as an animal feed, is supplemented with amounts of the yeast-expressed phytase sufficient to increase the nutritional value of the foodstuff. For example, in one embodiment, the foodstuff is supplemented with less than 2000 units (U) of the phytase expressed in yeast per kilogram (kg) of the foodstuff. This amount of phytase is equivalent to adding about 34 mg of the phytase to one kg of the foodstuff (about 0.0034% w/w). In another embodiment, the foodstuff is supplemented with less than 1500 U of the phytase expressed in yeast per kg of the foodstuff. This amount of phytase is equivalent to adding about 26 mg of the phytase to one kg of the foodstuff (about 0.0026% w/w). In another embodiment, the foodstuff is supplemented with less than 1200 U of the phytase expressed in yeast per kg of the foodstuff. This amount of phytase is equivalent to adding about 17 mg of the phytase to one kg of the foodstuff (about 0.0017% w/w). In another embodiment the foodstuff, such as an animal feed composition, is supplemented with about 50 U/kg to about 1000 U/kg of the yeast-expressed phytase (i.e., about 0.7 to about 14.3 mg/kg or about 0.00007% to about 0.0014% (w/w)). In yet another embodiment the foodstuff is supplemented with about 50 U/kg to about 700 U/kg of the yeast-expressed phytase (i.e., about 0.7 to about 10 mg/kg or about 0.00007% to about 0.001% (w/w)). In still another embodiment the foodstuff is supplemented with about 50 U/kg to about 500 U/kg of the yeast-expressed phytase (i.e., about 0.7 to about 7 mg/kg or about 0.00007% to about 0.007% (w/w)). In yet another embodiment, the foodstuff is supplemented with about 50 U/kg to about 200 U/kg of the yeast-expressed phytase (i.e., about 0.7 to about 2.9 mg/kg or about 0.00007% to about 0.0003% (w/w)). In each of these embodiments it is to be understood that "kg" refers to kilograms of the foodstuff, such as the final feed composition in the case of an animal feed blend (i.e., the feed in the composition as a final mixture). In addition, one unit (U) of phytase activity is defined as the quantity of enzyme required to produce 1 µmol of inorganic phosphate per minute from 1.5 mmol/L of sodium phytate at 37° C. and at a pH of 5.5.

The yeast-expressed phytase can be mixed with the foodstuff, such as an animal feed (i.e., the feed composition as a final mixture), prior to feeding the animal the foodstuff or the phytase can be fed to the animal with the foodstuff without prior mixing. For example, the phytase can be added directly to an untreated, pelletized, or otherwise processed foodstuff, such as an animal feed, or the phytase can be provided separately from the foodstuff in, for example, a mineral block, a pill, a gel formulation, a liquid formulation, or in drinking water. In accordance with the invention, feeding the animal the foodstuff "in combination with" the phytase means feeding the foodstuff mixed with the phytase or feeding the foodstuff and phytase separately without prior mixing.

The yeast expressed-phytase can be in an unencapsulated or an encapsulated form for feeding to the animal or for mixture with an animal feed blend. Encapsulation protects the phytase from breakdown and/or oxidation prior to ingestion by the animal (i.e., encapsulation increases the stability of the protein) and provides a dry product for easier feeding to the animal or for easier mixing with, for example, an animal feed blend. The yeast-expressed phytase can be protected in this manner, for example, by coating the phytase with another protein or any other substances known in the art to be effective encapsulating agents such as polymers, waxes, fats, and hydrogenated vegetable oils. For example, the phytase can be encapsulated using an art-recognized technique such as a $Na^{2+}$-alginate encapsulation technique wherein the phytase is coated with $Na^{2+}$-alginate followed by conversion to $Ca^{2+}$-alginate in the presence of $Ca^{2+}$ ions for encapsulation. Alternatively, the phytase can be encapsulated by an art-recognized technique such as prilling (i.e., atomizing a molten liquid and cooling the droplets to form a bead). For example, the phytase can be prilled in hydrogenated cottonseed flakes or hydrogenated soy bean oil to produce a dry product. The phytase can be used in an entirely unencapsulated form, an entirely encapsulated form, or mixtures of unencapsulated and encapsulated phytase can be added to the foodstuff, such as an animal feed composition, or fed directly to the animal without prior mixing with the foodstuff. Any phytase for use in accordance with the method of the present invention can be similarly treated.

In accordance with the method of the present invention, the phytase-containing foodstuff can be administered to animals orally in a foodstuff, such as an animal feed, or in a mineral block or in drinking water, but any other effective method of administration known to those skilled in the art can be utilized (e.g., a pill form). The foodstuff containing yeast-expressed phytase can be administered to the animals for any time period that is effective to increase the bioavailability of phosphate from phytate, to reduce the feed to weight gain ratio, or to increase the bone mass and mineral content of the animal. For example, in the case of a feed composition fed to a monogastric animal, the feed composition containing yeast-expressed phytase can be fed to the animal daily for the lifetime of the animal. Alternatively, the phytase-containing feed composition can be fed to the animal for a shorter time period. The time periods for feeding the phytase-containing foodstuff to animals are nonlimiting and it should be appreciated that any time period determined to be effective to enhance animal nutrition by administering the phytase-containing foodstuff can be used.

EXAMPLE 1

Animal Feed Blend Composition

The composition of the animal feed blend for chicks and pigs (i.e., the feed composition without phytase) was as follows:

TABLE 1

Composition of the animal feed blend used in chick and pig assays.

| Ingredient | Chick Assays | Pig Assay |
|---|---|---|
| Cornstarch | to 100.0 | to 100.0 |
| Corn | 50.89 | 61.35 |
| Soybean meal, dehulled | 39.69 | 31.19 |
| Soybean oil | 5.00 | 3.00 |
| Limestone, ground | 1.67 | 1.06 |
| Salt | 0.40 | — |
| Chick vitamin mix | 0.20 | — |
| Pig vitamin mix | — | 0.20 |
| Chick trace mineral mix | 0.15 | — |
| Pig trace vitamin mix | — | 0.35 |
| Choline chloride (60%) | 0.20 | — |
| Pig antibiotic premix (CSP) | — | 0.50 |
| Bacitracin premix | 0.05 | — |
| Copper sulfate | — | 0.08 |
| L-Lysine HCl, feed grade | — | 0.17 |
| DL-Methionine, feed grade | 0.20 | 0.05 |

EXAMPLE 2

Phytase Preparation

Yeast seed cultures were inoculated in growth medium with *Pichia pastoris* X33 transformed with either AOX1-appA, pGAP-appA2, or AOX1-Mutant U. The seed cultures were grown at 30° C. for about 24 hours until an $OD_{600}$ of about 50 was reached. The seed cultures were then used to inoculate fermentors (batch process) containing sterile FM-22 growth medium containing 5% glucose. The 24-hour seed cultures were diluted about 1:25 to about 1:50 into the FM-22 growth medium. The yeast cultures were incubated aerobically in the fermentors at 30° C. with pH control at 6.0 (using $NH_2OH$) and with continuous glucose feed until the cultures reached an $OD_{600}$ of about 400 (about 36 hours).

To collect the phytases from the culture medium, the yeast cultures were rapidly chilled to 8° C. The cells were separated from the culture medium by centrifugation and by microfiltration. The phytases were 70-80% pure in the culture medium and were prepared for blending with a carrier as a feed additive as follows.

The cell-free media containing the secreted phytases were concentrated by ultrafiltration (10,000 MW exclusion limit). The ultrafiltration retentates (7-5% solids) were transferred to sterile containers for spray drying. The retentates were spray dried using standard techniques known in the art and the resulting powder was collected (4-6% moisture).

Microbiological testing of the powder was performed and the powder was assayed for phytase activity. The phytase activity of the powder (units of phytase activity/mg of powder) was used to determine the amount of dried powder to be blended with wheat middlings (i.e., the carrier) to obtain a phytase/carrier mixture with a predetermined number of phytase units/gram of the carrier. The dried phytase powder was mixed with the wheat middlings and packaged in moisture-proof containers. The phytase-containing wheat middlings were mixed with an animal feed blend as needed to obtain a final feed mixture with a predetermined number of phytase units/kg of the feed (about 400 to about 1000 U/kg).

EXAMPLE 3

Feed Additive Composition

The following compositions are exemplary of feed additive compositions that may be mixed with an animal feed blend, such as the animal feed blend described in Example 1, to obtain a final feed mixture with, for example, about 50 U of phytase/kilogram of the final feed mixture to about 2000 U of phytase/kilogram of the feed. The feed additive compositions described below are nonlimiting and it should be appreciated that any phytase-containing feed additive composition determined to be effective to enhance the nutritional value of animal feed may be used. Exemplary feed additive compositions are shown for a feed additive composition containing 600 units of phytase/gram of the feed additive composition or 5000 units of phytase/gram of the feed additive composition.

|  | 600 phytase units/gram (weight percent) | 5000 phytase units/gram (weight percent) |
| --- | --- | --- |
| Rice hulls | 82.64 | 76.35 |
| Calcium carbonate | 15.00 | 15.00 |
| Oil | 1.5 | 1.5 |
| Enzyme | 0.86 | 7.15 |
| Wheat middlings | 82.64 | 76.35 |
| Calcium carbonate | 15.00 | 15.00 |
| Oil | 1.5 | 1.5 |
| Enzyme | 0.86 | 7.15 |

EXAMPLE 4

Feeding Protocol

Chicks were fed using the protocol described in Biehl, et al. (J. Nutr. 125:2407-2416 (1995)). Briefly, assays were conducted with male and female chicks from the cross of New Hampshire males and Columbian females and were conducted in an environmentally controlled laboratory room with 24 hour fluorescent lighting. From day 0 to day 7 posthatching, chicks were fed a basal diet of 23% crude protein, methionine-fortified corn-soybean meal as described above in Example 1. On day 8, chicks were weighed, wingbanded and assigned randomly to experimental treatments. Five pens of three or four chicks per pen received each dietary treatment for a 13-day experimental feeding period, and the chicks had an average initial weight of 80 to 100 grams.

Throughout the 13-day feeding period, chicks were confined in thermostatically controlled stainless-steel chick batteries, and stainless-steel feeders and waterers were also used. These steps were taken to avoid mineral contamination from the environment. Diets and distilled deionized water were freely available throughout the feeding period.

Pigs were fasted for 12 hours before the beginning of each assay, were fed the experimental diets for 23 days, and were fasted for 12 hours after each assay was completed. Ten pigs were used per treatment group and the pigs averaged about 8-120 kg at the initiation of the assay. Pigs were housed in individual pens that contained a stainless-steel feeder, a stainless-steel waterer, and galvanized round-bar fencing.

All of the chicks in each treatment group and the five median-weight pigs of each treatment group were euthanized for testing. Body weight gain was measured and tibia (chicks) or fibula (pigs) bones were harvested for bone ash analysis as a reflection of bone mass and mineral content.

EXAMPLE 5

Measurement of Inorganic Phosphate and Bioavailable Phospate

Total phosphate in the feed samples used to generate a standard curve was quantified calorimetrically according to AOAC (1984) as described in Biehl et al. Monobasic potassium phosphate ($KH_2PO_4$) served as the standard. A standard curve was generated by measuring inorganic phosphate levels in basal feed supplemented with $KH_2PO_4$ (X-axis) and determining tibia ash weight (mg) or weight gain (g) (Y-axis) for animals fed basal feed supplemented with various levels of $KH_2PO_4$. The bioavailability of phosphate from phytate was then determined for animals fed basal feed supplemented with phytase by comparison of tibia ash weight and weight gain in these animals to the standard curve.

EXAMPLE 6

Bone Ash Analysis

At the end of each experiment, chicks or pigs were euthanized, and right tibia or fibula bones were removed quantitatively from chicks or pigs, respectively. The bones were pooled by replicate pen and, after removal of adhering tissue, were dried for 24 hours at 100° C. and were weighed. After weighing, the bones were dry ashed for 24 hours at 600° C. in a muffle furnace. Ash weight was expressed as a percentage of dry bone weight and also as ash weight per bone.

EXAMPLE 7

Phytase Expression in Yeast

In accordance with the present invention, any phytase gene may be expressed in yeast, and any yeast expression system may be used according to methods known to those skilled in the art. Yeast expression systems are described for exemplary phytase genes, such as the *E. coli*-derived appA and appA2 genes, and for a site-directed mutant of *E. coli*-derived AppA, in U.S. patent application Ser. No. 09/104,769 (now U.S. Pat. No. 6,451,572), U.S. patent application Ser. No. 09/540,149, and in U.S. patent application Ser. No. 60/166,179 (PCT Publication No. WO 01/36607 A1), all incorporated herein by reference. Exemplary yeast expression systems for expressing the AppA and AppA2 enzymes and a site-directed mutant of AppA are described briefly below.

Expression of the appA gene in *Saccharomyces cerevisiae*.

The appA gene was expressed in *Saccharomyces cerevisiae* linked to the signal peptide of the phyA gene (phytase gene from *Aspergillus niger*). The appA gene was obtained from the ATCC, P.O. Box 1549, Manassas, Va. 20108, where it was deposited pursuant to the requirements of the Budapest Treaty, under ATCC accession number 87441. The appA gene (1.3 kb) was transformed into *E. coli* strain BL21 using the pappA1 expression vector (Ostanin et al., J. Biol. Chem., 267:22830-36 (1992)). To prepare the appA-phyA signal peptide construct, the polymerase chain reaction (PCR) was used. Two primers were synthesized and the 5' primer was 80 base pairs in length and contained the phyA signal peptide sequence, a KpnI restriction enzyme cut site, and sequence complementary to the template as follows: 5' GGG GTA CCA TGG GCG TCT CTG CTG TTC TAC TTC CTT TGT ATC TCC TGT CTG GAG TCA CCT CCG GAC AGA GTG AGC CGG AG 3' (SEQ. ID No.: 6). The 3' primer was 24 base pairs in length and contained an EcoRI site and sequence complementary to the template as follows: 5' GGG AAT TCA TTA CAA ACT GCA GGC 3' (SEQ. ID No.: 7). The PCR reaction was run for 25 cycles with 1 minute of denaturation at 95° C., 1 minute of annealing at 58° C., and 1 minute of chain extension at 72° C.

A 1.3 kb fragment was amplified by PCR, and was digested with KpnI and EcoRI and ligated into pYES2, a vector for expression in *Saccharomyces cerevisiae*. The pYES2-appA-phyA signal peptide construct was transformed into the yeast (INVScI, Invitrogen, San Diego, Calif.) by the lithium acetate method.

Selected transformants were inoculated into YEPD medium and expression was induced with galactose after an $OD_{600}$ of 2 was reached. The cells were harvested 15-20 hours after induction. The AppA phytase enzyme was isolated from the culture supernatant and was the major protein present eliminating the need for a tedious purification.

Expression of the appA or appA2 gene in *Pichia pastoris*.

appA. The template for the PCR reaction was as described above. The 5' primer used for the PCR reaction was as follows: 5' GGA ATT CCA GAG TGA GCC GGA 3' (SEQ ID No.: 8). The 3' primer was as follows: 5' GGG GTA CCT TAC AAA CTG CAC G 3' (SEQ ID No.: 9). The amplification reaction included 1 cycle at 94° C. (3 min.), 30 cycles at 94° C. (0.8 min), 30 cycles at 54° C. (1 min.), 30 cycles at 72° C. (2 min.), and 1 cycle at 72° C. (10 min). The product was first inserted into the pGEM T-easy vector (Promega), and *E. coli* strain TOP10F' was used as the host to amplify the construct. The construct was then inserted into the yeast expression vector pPIcZαA (Invitrogen) at the EcoRI site, and *E. coli* strain TOP10F' was again used as the host to amplify the construct.

The PIcZα vector containing appA was transformed into *Pichia pastoris* strain X33 by electroporation. The transformed cells were plated into YPD-Zeocin agar medium and positive colonies were incubated in minimal media with glycerol (BMGY) for 24 hours. When an $OD_{600}$ of 5 was reached, the cells were centrifuged and were resuspended in 0.5% methanol medium (BMMY) for induction. Methanol (100%) was added every 24 hours to maintain a concentration of 0.5-1%. The cells were harvested at 192 hours after induction and the AppA protein was purified by ammonium sulfate precipitation and DEAE-Sepharose column chromatography.

appA2. The appA2 gene was isolated (see U.S. patent application Ser. No. 09/540,179) from a bacterial colony that exhibited particularly high phytase activity obtained from the colon contents of crossbred Hampshire-Yorkshire-Duroc pigs. To isolate a bacterial colony exhibiting high phytase activity the colon contents sample was diluted in an anaerobic rumen fluid glucose medium, was shaken vigorously for 3 minutes, and was serially diluted. The diluted samples were cultured at 37° C. for 3 days on a modified rumen fluid-glucose-cellobiose-Agar medium containing insoluble calcium phytate. Colonies with a clear zone were assayed for phytase activity using sodium phytate as a substrate. The colony identified as producing the highest phytase activity was identified as an *E. coli* strain. Accordingly, the appA2 gene was isolated using the primers as described above for appA expression in *Pichia pastoris* (SEQ. ID Nos. 8 and 9). The appA2 gene was cloned into the PIcZα vector and *Pichia pastoris* strain X33 was transformed with the PIcZα-appA2 construct as described above for appA expression in *Pichia pastoris*. The AppA2 enzyme was expressed as described above for AppA, and the AppA2 protein was collected from the yeast culture supernatant.

AppA Site-Directed Mutants.

Site-directed mutants of appA were prepared as described in U.S. patent application Ser. No. 06/166,179 (PCT Publication No. WO 01/36607 A1), incorporated herein by reference. Briefly, the *E. coli* appA mutants were constructed using the megaprimer site-directed mutagenesis method (Seraphin, B. et al., *Nucleic Acids Res.* 24:3276-77 (1996); Smith, A. M. et al., *Biotechniques* 22: 438-39 (1997), which are hereby incorporated by reference).

The template for mutagenesis was obtained from ATCC, and the gene (1.3 kb) was transformed into *E. coli* strain BL21 (No. 87441) using the pappA1 expression vector (Ostanin et al., J. Biol. Chem., 267:22830-36 (1992)). The template was amplified as described above for appA expressed in *Pichia pastoris* using the primers used above for appA expression in *Pichia pastoris* (SEQ. ID Nos.: 8 and 9). The amplification reaction included 1 cycle at 94° C. (3 min.), 30 cycles at 94° C. (0.5 min), 30 cycles at 54° C. (1 min.), 30 cycles at 72° C. (1.5 min.), and 1 cycle at 72° C. (10 min).

The mutagenesis PCR reaction was performed as described above using the primers as follows:

```
                             (SEQ ID No.: 10)
5'CTGGGTATGGTTGGTTATATTACAGTCAGGT3'   A131N
                                      V134N
                             (SEQ ID No.: 11)
5'CAAACTTGAACCTTAAACGTGAG3'           C200N
                             (SEQ ID No.: 12)
5'CCTGCGTTAAGTTACAGCTTTCATTCTGTTT3'   D207N
                                      S211N
```

The mutagenic PCR reactions incorporated appropriate primers to make the A131N/V134N/D207N/S211N, C200N/D207N/S211N (Mutant U), and A131N/V134N/C200N/D207N/S211N mutants of appA. The first mutagenic PCR reaction (100 µl) was performed as described above, using 4 µl of the intact appA PCR reaction mixture and the appropriate modified primers listed above. All megaprimer PCR products were resolved in a 1.5% low melting agarose gel. The expected fragments were excised and eluted with a GENECLEAN II kit. The final mutagenic PCR reaction (100 µl) was set up as described above, using 4 µl of the appA PCR product and varying concentrations of the purified megaprimer (50 ng to 41 µg), depending on its size. Five thermal cycles were set up at 94° C. for 1 minute and 70° C. for 2 minutes. While at 70° C., 1 µmol of forward primer and 2 U of AmpliTaq DNA polymerase were added and gently mixed with the reaction mixture, and thermal cycling continued for 25 cycles at 94° C. for 1 minute and 70° C. for 1.5 minutes.

The genes encoding the site-directed mutants were expressed in *Pichia pastoris* as described above for the appA2 gene. The protein products were expressed as described above for AppA, and the site-directed mutants were purified from the yeast culture supernatant by ammonium sulfate precipitation and DEAE-Sepharose chromatography.

EXAMPLE 8

In Vivo Effects of Yeast—Expressed Phytases Fed to Chicks

To evaluate their potential as animal feed supplements, the yeast-expressed phytases AppA and AppA2, were dried and added to the animal feed blend (23% crude protein) described above in Example 1 using wheat middlings as a carrier. Chicks (four chicks per pen; average initial weight of 97 grams) were fed phytase-supplemented feed compositions as described above in Example 4. The treatment groups included various level of $KH_2PO_4$ to construct the standard curve, 500 U/kg of Natuphos®, a commercially available (Gist-Brocades) phytase expressed in the fungus *Aspergillus niger*, 500 U/kg of AppA expressed in *Pichia pastoris* or in *E. coli,* and various levels of AppA2/p (AppA2 expressed in *Pichia pastoris* using the constitutive pGAP promoter for gene expression) as follows:

Treatment Groups:

| | |
|---|---|
| 1. | Basal Diet (0.10% P, 0.75% Ca) |
| 2. | Same as 1 + 0.05% P from $KH_2PO_4$ |
| 3. | Same as 1 + 0.10% P from $KH_2PO_4$ |
| 4. | Same as 1 + 0.15% P from $KH_2PO_4$ |
| 5. | Same as 1 + 500 U/kg AppA (yeast) |
| 6. | Same as 1 + 500 U/kg AppA (*E. coli*) |
| 7. | Same as 1 + 500 U/kg AppA2/p |
| 8. | Same as 1 + 1000 U/kg AppA2/p |
| 9. | Same as 1 + 1500 U/kg AppA2/p |
| 10. | Same as 1 + 500 U/kg Natuphos ® |

For the various treatment groups weight gain, feed intake, the feed to weight gain ratio, dry tibia weight, tibia ash weight, tibia ash weight as a percent of dry tibia weight, and the percentage of bioavailable phosphate based on both tibia ash weight and weight gain were determined. The results are expressed below as a mean for the four chicks for each of the five pens (R1, R2, R3, R4, and R5), and the mean for the five pens was also calculated (labeled "mean" in the tables). The treatment groups are labeled T1-T10 in the tables, and "g/c/d" indicates weight gain or feed intake in grams/chick/day.

Weight gain (g/c)

| | T1 | T2 | T3 | T4 | T5 | T6 | T7 | T8 | T9 | T10 |
|---|---|---|---|---|---|---|---|---|---|---|
| R1 | 185 | 282 | 315 | 321 | 314 | 284 | 334 | 352 | 334 | 269 |
| R2 | 219 | 286 | 315 | 336 | 317 | 322 | 315 | 326 | 348 | 274 |
| R3 | 234 | 277 | 327 | 335 | 321 | 312 | 318 | 321 | 342 | 267 |
| R4 | 234 | 291 | 309 | 311 | 316 | 308 | 326 | 342 | 333 | 276 |
| R5 | 223 | 278 | 303 | 332 | 316 | 268 | 313 | 336 | 361 | 294 |
| Mean | 219[g] | 283[ef] | 314[cd] | 327[bc] | 317[c] | 299[de] | 321[bc] | 335[ab] | 344[a] | 276[f] |
| g/c/d | 16.8 | 21.8 | 24.2 | 25.2 | 24.4 | 23.0 | 24.7 | 25.8 | 26.5 | 21.2 |

Pooled SEM = 6
LSD = 16

13-d Feed intake (g/c)

| | T1 | T2 | T3 | T4 | T5 | T6 | T7 | T8 | T9 | T10 |
|---|---|---|---|---|---|---|---|---|---|---|
| R1 | 303 | 392 | 434 | 434 | 426 | 389 | 450 | 474 | 465 | 397 |
| R2 | 330 | 462 | 448 | 454 | 429 | 430 | 425 | 449 | 472 | 396 |
| R3 | 336 | 391 | 445 | 458 | 446 | 425 | 428 | 445 | 464 | 397 |
| R4 | 350 | 416 | 432 | 424 | 432 | 420 | 441 | 464 | 449 | 386 |
| R5 | 335 | 388 | 421 | 467 | 425 | 389 | 453 | 461 | 483 | 420 |
| Mean | 331[f] | 410[e] | 436[c] | 447[abc] | 432[cd] | 411[de] | 439[bc] | 459[ab] | 467[a] | 399[e] |
| g/c/d | 25.5 | 31.5 | 33.5 | 34.4 | 33.2 | 31.6 | 33.8 | 35.3 | 35.9 | 30.7 |

Pooled SEM = 7
LSD = 21

Gain/feed (g/kg)

| | T1 | T2 | T3 | T4 | T5 | T6 | T7 | T8 | T9 | T10 |
|---|---|---|---|---|---|---|---|---|---|---|
| R1 | 611 | 718 | 726 | 740 | 738 | 729 | 742 | 742 | 720 | 678 |
| R2 | 665 | 618 | 703 | 741 | 738 | 749 | 741 | 727 | 738 | 692 |
| R3 | 696 | 708 | 736 | 730 | 719 | 736 | 743 | 722 | 736 | 671 |

-continued

Gain/feed (g/kg)

|  | T1 | T2 | T3 | T4 | T5 | T6 | T7 | T8 | T9 | T10 |
|---|---|---|---|---|---|---|---|---|---|---|
| R4 | 668 | 700 | 715 | 733 | 731 | 733 | 738 | 738 | 743 | 715 |
| R5 | 665 | 717 | 721 | 710 | 742 | 688 | 691 | 730 | 749 | 710 |
| Mean | 661[c] | 692[b] | 720[a] | 731[a] | 734[a] | 727[a] | 731[a] | 732[a] | 737[a] | 691[b] |

Pooled SEM = 10
LSD = 28

Dry tibia weight (mg/c)

|  | T1 | T2 | T3 | T4 | T5 | T6 | T7 | T8 | T9 | T10 |
|---|---|---|---|---|---|---|---|---|---|---|
| R1 | 659 | 804 | 883 | 981 | 892 | 787 | 914 | 1059 | 1106 | 757 |
| R2 | 655 | 769 | 891 | 977 | 907 | 918 | 873 | 997 | 1083 | 759 |
| R3 | 713 | 751 | 878 | 1008 | 901 | 820 | 905 | 964 | 1065 | 726 |
| R4 | 740 | 742 | 931 | 925 | 823 | 809 | 923 | 1083 | 1096 | 729 |
| R5 | 714 | 714 | 866 | 942 | 841 | 809 | 931 | 1036 | 1132 | 764 |
| Mean | 698[g] | 756[f] | 890[d] | 967[c] | 873[de] | 829[e] | 909[d] | 1028[b] | 1096[a] | 747[f] |

Pooled SEM = 16
LSD = 45

Tibia Ash (mg/c)

|  | T1 | T2 | T3 | T4 | T5 | T6 | T7 | T8 | T9 | T10 |
|---|---|---|---|---|---|---|---|---|---|---|
| R1 | 232 | 307 | 406 | 492 | 434 | 345 | 439 | 590 | 617 | 278 |
| R2 | 215 | 315 | 415 | 507 | 445 | 435 | 420 | 546 | 600 | 305 |
| R3 | 259 | 300 | 406 | 520 | 435 | 382 | 451 | 523 | 604 | 284 |
| R4 | 237 | 297 | 442 | 462 | 392 | 372 | 454 | 590 | 616 | 267 |
| R5 | 242 | 277 | 396 | 471 | 432 | 373 | 471 | 548 | 642 | 316 |
| Mean | 237[h] | 299[g] | 413[e] | 490[c] | 428[de] | 381[f] | 447[d] | 559[b] | 616[a] | 290[g] |

Pooled SEM = 10
LSD = 28

Supplemental P Intake (g)

|  | T1 | T2 | T3 | T4 |
|---|---|---|---|---|
| R1 | 0 | 0.196 | 0.434 | 0.651 |
| R2 | 0 | 0.231 | 0.448 | 0.680 |
| R3 | 0 | 0.196 | 0.445 | 0.687 |
| R4 | 0 | 0.208 | 0.432 | 0.636 |
| R5 | 0 | 0.194 | 0.421 | 0.701 |
| Mean | 0[d] | 0.205[c] | 0.436[b] | 0.671[a] |

Pooled SEM = 0.007
LSD = 0.022

Tibia ash (%)

|  | T1 | T2 | T3 | T4 | T5 | T6 | T7 | T8 | T9 | T10 |
|---|---|---|---|---|---|---|---|---|---|---|
| R1 | 35.15 | 38.22 | 46.03 | 50.12 | 48.64 | 43.78 | 47.98 | 55.64 | 55.79 | 36.78 |
| R2 | 32.86 | 40.92 | 46.53 | 51.86 | 49.06 | 47.31 | 48.07 | 54.69 | 55.35 | 40.15 |
| R3 | 36.30 | 39.96 | 46.22 | 51.61 | 48.31 | 46.62 | 49.85 | 54.23 | 56.69 | 39.14 |
| R4 | 32.01 | 40.02 | 47.47 | 49.96 | 47.70 | 45.96 | 49.19 | 54.44 | 56.23 | 36.68 |
| R5 | 33.45 | 38.82 | 45.74 | 49.95 | 51.40 | 46.11 | 50.54 | 52.86 | 56.71 | 41.32 |
| Mean | 33.95[g] | 39.59[f] | 46.40[e] | 50.70[c] | 49.02[d] | 45.96[e] | 49.13[cd] | 54.37[b] | 56.15[a] | 38.81[f] |

Pooled SEM = 0.57
LSD = 1.62

Phosphorus Equivalency Estimates

Tibia Ash Weight

KH$_2$PO$_4$ Standard Curve:　Y = tibia ash (mg)
　　　　　　　　　　　　　　X = supplemental or equivalent P intake (g)
Y = 232.0 + 389.9X
r$^2$ = 0.97

For 500 U/kg Phytase activity
(example calculations using tibia ash treatment means)

|  |  | % Bioavailable P |
|---|---|---|
| AppA (yeast): | (428−232.0)/389.9 = 0.503 g P from 432 g FI = | 0.116% |
| AppA (*E. coli*): | (381 − 232.0)/389.9 = 0.382 g P from 411 g FI = | 0.093% |
| AppA2/p: | (447 − 232.0)/389.9 = 0.551 g P from 439 g FI = | 0.126% |
| Natuphos ®: | (290 − 232.0)/389.9 = 0.149 g P from 399 g FI = | 0.037% |

** Results from ANOVA (calculation performed for each pen of four birds; treatment legend on previous page)

Bioavailable P (%)

|  | T5 | T6 | T7 | T8 | T9 | T10 |
|---|---|---|---|---|---|---|
| R1 | 0.122 | 0.075 | 0.118 | 0.194 | 0.212 | 0.030 |
| R2 | 0.127 | 0.121 | 0.113 | 0.179 | 0.200 | 0.047 |
| R3 | 0.117 | 0.091 | 0.131 | 0.168 | 0.206 | 0.034 |
| R4 | 0.095 | 0.085 | 0.129 | 0.198 | 0.219 | 0.023 |
| R5 | 0.121 | 0.093 | 0.135 | 0.176 | 0.218 | 0.051 |
| Mean | 0.116$^c$ | 0.093$^d$ | 0.125$^c$ | 0.183$^b$ | 0.211$^a$ | 0.037$^e$ |

Pooled SEM = 0.005
LSD = 0.016

| Contrasts | Significance (P-value) |
|---|---|
| AppA (yeast) vs. AppA (*E. coli*) | 0.006 |
| AppA2/p linear | 0.001 |
| AppA2/p quadratic | 0.039 |

Weight Gain

KH$_2$PO$_4$ Standard Curve:　X = weight gain (g)
　　　　　　　　　　　　　　Y = supplemental P intake (g)
Y = 234.1 + 157.2X
r$^2$ = 0.84

Results from ANOVA (calculation performed for each pen of four birds; treatment legend on previous page)

Bioavailable P (%)

|  | T5 | T6 | T7 | T8 | T9 | T10 |
|---|---|---|---|---|---|---|
| R1 | 0.119 | 0.082 | 0.141 | 0.158 | 0.137 | 0.056 |
| R2 | 0.123 | 0.130 | 0.121 | 0.130 | 0.154 | 0.064 |
| R3 | 0.124 | 0.117 | 0.125 | 0.124 | 0.148 | 0.053 |
| R4 | 0.121 | 0.112 | 0.133 | 0.148 | 0.140 | 0.069 |
| R5 | 0.123 | 0.055 | 0.111 | 0.141 | 0.167 | 0.091 |
| Mean | 0.122$^b$ | 0.099$^d$ | 0.126$^b$ | 0.140$^{ab}$ | 0.149$^a$ | 0.067$^d$ |

Pooled SEM = 0.007
LSD = 0.021

| Contrasts | Significance (P-value) |
|---|---|
| AppA (yeast) vs. AppA (*E. coli*) | 0.038 |
| AppA2/p linear | 0.036 |
| AppA2/p quadratic | 0.768 |

Supplementation of the animal feed blend with increasing amounts of KH$_2$PO$_4$ resulted in linear (p<0.001) increases in weight gain, tibia ash. Supplementation of the animal feed blend with Natuphos® resulted in linear increases (p<0.001) in weight gain, tibia ash, and % bioavailable phoshate. At 500 U/kg the yeast-expressed enzymes (AppA and AppA2/p) were more effective than *E. coli*-expressed AppA or Natuphos® at improving each of the in vivo responses tested, including the feed to weight gain ratio, tibia weight, and % bioavailable phosphate. In fact, AppA and AppA2/p were 2-6 times more effective at increasing the level of bioavailable phosphate than Natuphos®, depending on whether tibia ash weight or weight gain was used to calculate the percent of bioavailable phosphate.

EXAMPLE 9

In Vivo Effects of Yeast-Expressed Phytases Fed to Chicks

The procedure was as described in Example 8 except that the chicks had an average initial weight of 91 grams, and the treatment groups were as follows:

Treatment Groups:

| 1. | Basal Diet (0.10% P, 0.75% Ca) |
|---|---|
| 2. | Same as 1 + 0.05% P from KH$_2$PO$_4$ |
| 3. | Same as 1 + 0.10% P from KH$_2$PO$_4$ |
| 4. | Same as 1 + 300 U/kg Natuphos ® phytase |
| 5. | Same as 1 + 500 U/kg Natuphos ® phytase |
| 6. | Same as 1 + 700 U/kg Natuphos ® phytase |
| 7. | Same as 1 + 900 U/kg Natuphos ® phytase |
| 8. | Same as 1 + 1100 U/kg Natuphos ® phytase |
| 9. | Same as 1 + 1300 U/kg Natuphos ® phytase |
| 10. | Same as 1 + 1500 U/kg Natuphos ® phytase |
| 11. | Same as 1 + 500 U/kg Ronozyme ® phytase |
| 12. | Same as 1 + 300 U/kg Mutant U phytase |
| 13. | Same as 1 + 500 U/kg Mutant U phytase |
| 14. | Same as 1 + 500 U/kg AppA phytase |
| 15. | Same as 1 + 500 U/kg AppA2 phytase |

The Ronozyme® (Roche) phytase is a phytase expressed in fungus. Mutant U is the site-directed mutant of AppA described above. The tables are labeled as described in Example 8. The in vivo effects of phytase supplementation described in Example 8 were measured and the results were as follows:

Weight gain (g/c)

|    | T1  | T2  | T3  | T4  | T5  | T6  | T7  | T8  | T9  | T10 | T11 | T12 | T13 | T14 | T15 |
|----|-----|-----|-----|-----|-----|-----|-----|-----|-----|-----|-----|-----|-----|-----|-----|
| R1 | 287 | 295 | 318 | 269 | 295 | 271 | 301 | 305 | 304 | 317 | 256 | 324 | 340 | 319 | 343 |
| R2 | 271 | 291 | 342 | 288 | 297 | 282 | 313 | 295 | 323 | 327 | 231 | 289 | 349 | 325 | 342 |
| R3 | 268 | 302 | 326 | 286 | 278 | 267 | 298 | 309 | 308 | 327 | 274 | 332 | 337 | 348 | 336 |
| R4 | 256 | 282 | 317 | 255 | 304 | 280 | 294 | 295 | 289 | 310 | 287 | 310 | 338 | 324 | 330 |
| R5 | 215 | 279 | 310 | 292 | 270 | 290 | 302 | 270 | 295 | 306 | 284 | 316 | 329 | 319 | 331 |
| Mean | 259 | 290 | 323 | 278 | 289 | 278 | 302 | 295 | 304 | 317 | 266 | 314 | 339 | 327 | 336 |
| g/c/d | 18.5 | 20.7 | 23.1 | 19.9 | 20.6 | 19.9 | 21.6 | 21.1 | 21.7 | 22.6 | 19.0 | 22.4 | 24.2 | 23.4 | 24.0 |

Pooled SEM = 6
LSD = 18

Feed intake (g/c)

|    | T1  | T2  | T3  | T4  | T5  | T6  | T7  | T8  | T9  | T10 | T11 | T12 | T13 | T14 | T15 |
|----|-----|-----|-----|-----|-----|-----|-----|-----|-----|-----|-----|-----|-----|-----|-----|
| R1 | 463 | 450 | 489 | 428 | 450 | 435 | 466 | 479 | 445 | 489 | 422 | 500 | 487 | 483 | 503 |
| R2 | 424 | 439 | 565 | 443 | 427 | 454 | 470 | 469 | 490 | 489 | 394 | 459 | 518 | 459 | 519 |
| R3 | 425 | 446 | 526 | 444 | 417 | 425 | 444 | 480 | 483 | 485 | 427 | 522 | 496 | 520 | 535 |
| R4 | 406 | 437 | 472 | 398 | 450 | 437 | 462 | 442 | 425 | 505 | 439 | 478 | 499 | 496 | 491 |
| R5 | 381 | 443 | 478 | 421 | 423 | 438 | 447 | 423 | 455 | 452 | 437 | 463 | 496 | 476 | 519 |
| Mean | 420 | 443 | 506 | 427 | 433 | 438 | 458 | 459 | 460 | 484 | 424 | 484 | 499 | 487 | 513 |
| g/c/d | 30.0 | 31.6 | 36.1 | 30.5 | 30.9 | 31.3 | 32.7 | 32.8 | 32.9 | 34.6 | 30.3 | 34.6 | 35.6 | 34.8 | 36.6 |

Pooled SEM =10
LSD = 27

Gain/feed (g/kg)

|    | T1  | T2  | T3  | T4  | T5  | T6  | T7  | T8  | T9  | T10 | T11 | T12 | T13 | T14 | T15 |
|----|-----|-----|-----|-----|-----|-----|-----|-----|-----|-----|-----|-----|-----|-----|-----|
| R1 | 620 | 656 | 650 | 627 | 655 | 623 | 645 | 636 | 683 | 648 | 605 | 648 | 699 | 661 | 681 |
| R2 | 639 | 662 | 606 | 651 | 696 | 621 | 665 | 629 | 659 | 668 | 587 | 629 | 672 | 709 | 659 |
| R3 | 630 | 677 | 619 | 644 | 666 | 628 | 671 | 644 | 637 | 673 | 641 | 635 | 680 | 669 | 629 |
| R4 | 631 | 645 | 671 | 641 | 675 | 642 | 636 | 668 | 679 | 614 | 654 | 649 | 678 | 652 | 671 |
| R5 | 564 | 630 | 649 | 694 | 639 | 662 | 675 | 639 | 648 | 678 | 649 | 683 | 663 | 669 | 638 |
| Mean | 617 | 654 | 639 | 651 | 666 | 635 | 658 | 643 | 661 | 656 | 627 | 649 | 678 | 672 | 656 |

Pooled SEM = 10
LSD = 28

Dry tibia weight (mg/c)

|    | 1   | 2   | 3   | 4   | 5   | 6   | 7   | 8   | 9   | 10  | 11  | 12  | 13  | 14  | 15  |
|----|-----|-----|-----|-----|-----|-----|-----|-----|-----|-----|-----|-----|-----|-----|-----|
| R1 | 970 | 1010 | 1146 | 952 | 1028 | 1011 | 1007 | 995 | 1027 | 1131 | —   | 1150 | 1169 | 1160 | 1234 |
| R2 | 920 | 1029 | 1175 | 974 | 937 | 1047 | 1013 | 993 | 1077 | 1077 | 828 | 995 | 1251 | 1130 | 1209 |
| R3 | 1038 | 872 | 1147 | 981 | 932 | 917 | 1049 | 1072 | 1030 | 1137 | 1029 | 1151 | 1238 | 1178 | 1215 |
| R4 | 890 | 944 | 1125 | 957 | 1008 | 964 | 1073 | 1005 | 961 | 1100 | 919 | 1116 | 1273 | 1177 | 1128 |
| R5 | 882 | 970 | 1078 | 954 | 976 | 1004 | 961 | 963 | 1065 | 1101 | 937 | 1046 | 1172 | 1141 | 1145 |
| Mean | 940 | 965 | 1134 | 964 | 976 | 989 | 1021 | 1006 | 1032 | 1109 | 928 | 1092 | 1221 | 1157 | 1186 |

Pooled SEM = 22
LSD = 61

Supplemental P intake (g)

|      | 1   | 2         | 3         |
|------|-----|-----------|-----------|
| R1   | 0   | 0.225     | 0.489     |
| R2   | 0   | 0.220     | 0.565     |
| R3   | 0   | 0.223     | 0.526     |
| R4   | 0   | 0.219     | 0.472     |
| R5   | 0   | 0.222     | 0.478     |
| Mean | 0[c] | 0.222[b] | 0.506[a] |

Tibia ash (mg/c)

|      | 1   | 2   | 3   | 4   | 5   | 6   | 7   | 8   | 9   | 10  | 11  | 12  | 13  | 14  | 15  |
|------|-----|-----|-----|-----|-----|-----|-----|-----|-----|-----|-----|-----|-----|-----|-----|
| R1   | 284 | 333 | 437 | 279 | 303 | 305 | 328 | 324 | 340 | 369 | —   | 401 | 428 | 453 | 457 |
| R2   | 270 | 318 | 447 | 298 | 290 | 336 | 336 | 325 | 383 | 363 | 226 | 355 | 481 | 441 | 470 |
| R3   | 291 | 271 | 398 | 302 | 278 | 263 | 326 | 357 | 345 | 403 | 293 | 410 | 479 | 420 | 455 |
| R4   | 234 | 305 | 398 | 281 | 314 | 297 | 341 | 317 | 324 | 364 | 264 | 406 | 500 | 447 | 413 |
| R5   | 243 | 327 | 388 | 287 | 279 | 309 | 302 | 305 | 352 | 368 | 279 | 354 | 447 | 424 | 443 |
| Mean | 264 | 311 | 414 | 289 | 293 | 302 | 327 | 326 | 349 | 373 | 266 | 385 | 467 | 437 | 448 |

Pooled SEM = 10
LSD = 28

Tibia ash (%)

|      | 1     | 2     | 3     | 4     | 5     | 6     | 7     | 8     | 9     | 10    | 11    | 12    | 13    | 14    | 15    |
|------|-------|-------|-------|-------|-------|-------|-------|-------|-------|-------|-------|-------|-------|-------|-------|
| R1   | 29.30 | 32.94 | 38.15 | 29.25 | 29.48 | 30.18 | 32.55 | 32.54 | 33.10 | 32.60 | —     | 34.90 | 36.63 | 39.07 | 37.06 |
| R2   | 29.29 | 30.97 | 38.03 | 30.61 | 30.99 | 32.06 | 33.21 | 32.73 | 35.51 | 33.67 | 27.33 | 35.66 | 38.48 | 39.04 | 38.89 |
| R3   | 28.03 | 31.08 | 34.70 | 30.81 | 29.79 | 28.71 | 31.12 | 33.26 | 33.45 | 35.49 | 28.50 | 35.63 | 38.73 | 35.63 | 37.48 |
| R4   | 26.30 | 32.33 | 35.34 | 29.35 | 31.17 | 30.80 | 31.73 | 31.55 | 33.71 | 33.11 | 28.74 | 36.38 | 39.29 | 38.00 | 36.63 |
| R5   | 27.52 | 33.76 | 35.98 | 30.13 | 28.60 | 30.81 | 31.44 | 31.67 | 33.09 | 33.41 | 29.77 | 33.81 | 38.14 | 37.18 | 38.70 |
| Mean | 28.09 | 32.21 | 36.44 | 30.03 | 30.00 | 30.51 | 32.01 | 32.35 | 33.77 | 33.65 | 28.58 | 35.28 | 38.25 | 37.78 | 37.75 |

Pooled SEM = 0.49
LSD = 1.39

Phosphorus Equivalency Estimates

KH$_2$PO$_4$ Standard Curve: Y = tibia ash (mg)
X = supplemental or equivalent P intake (g)
Y = 257.1 + 299.0X
r$^2$ = 0.88

For 500 U/kg Phytase activity

| (example calculations using tibia ash treatment mean) | | % Bioavailable P |
|---|---|---|
| Natuphos ®: | (293 − 257.1)/299.0 = 0.120 g P from 433 g FI = | 0.030% |
| Ronozyme ®: | (266 − 257.1)/299.0 = 0.030 g P from 424 g FI = | 0.007% |
| Mutant U: | (467 − 257.1)/299.0 = 0.702 g P from 499 g FI = | 0.141% |
| AppA: | (437 − 257.1)/299.0 = 0.602 g P from 487 g FI = | 0.124% |
| AppA2: | (448 − 257.1)/299.0 = 0.638 g P from 513 g FI = | 0.124% |

Results from ANOVA (calculation performed for each pen of four birds; treatment legend on previous page)

Bioavailable P (%)

|      | 4     | 5     | 6     | 7     | 8     | 9     | 10    | 11     | 12    | 13    | 14    | 15    |
|------|-------|-------|-------|-------|-------|-------|-------|--------|-------|-------|-------|-------|
| R1   | 0.017 | 0.034 | 0.037 | 0.051 | 0.047 | 0.062 | 0.076 | —      | 0.097 | 0.117 | 0.136 | 0.133 |
| R2   | 0.031 | 0.026 | 0.058 | 0.057 | 0.049 | 0.086 | 0.072 | −0.026 | 0.071 | 0.145 | 0.134 | 0.137 |
| R3   | 0.034 | 0.017 | 0.005 | 0.052 | 0.069 | 0.061 | 0.101 | 0.028  | 0.098 | 0.150 | 0.105 | 0.124 |
| R4   | 0.020 | 0.043 | 0.030 | 0.060 | 0.045 | 0.053 | 0.071 | 0.006  | 0.104 | 0.163 | 0.128 | 0.106 |
| R5   | 0.024 | 0.018 | 0.040 | 0.034 | 0.038 | 0.071 | 0.082 | 0.017  | 0.070 | 0.128 | 0.117 | 0.120 |
| Mean | 0.025 | 0.027 | 0.034 | 0.051 | 0.050 | 0.066 | 0.080 | 0.006  | 0.088 | 0.140 | 0.124 | 0.124 |

Pooled SEM = 0.006
LSD = 0.018

| Contrasts | Significance (P-value) |
|---|---|
| Linear response to Natuphos ® (treatment groups 5 (trt) 4–10) | 0.001 |
| Quadratic response to Natuphos ® | 0.208 |
| 500 U/kg Natuphos ® (trt 5) vs 500 U/kg yeast-expressed phytases (trt 13–15) | 0.001 |

| -continued | |
|---|---|
| 500 U/kg Natuphos ® (trt 5) vs 500 U/kg Ronozyme ® (trt 11) | 0.031 |
| 500 U/kg Ronozyme ® (trt 11) vs 500 U/kg yeast-expressed phytases (trt 13–15) | 0.001 |
| 300 U/kg Mutant U (trt 12) vs 500 U/kg Mutant U (trt 13) | 0.001 |
| 500 U/kg Mutant U (trt 12) vs 500 U/kg AppA (trt 14) | 0.074 |
| 500 U/kg Mutant U (trt 12) vs 500 U/kg AppA2 (trt 15) | 0.074 |

Multiple Linear Regression:    Y = tibia ash (mg)
                                X = phytase intake (U)
Y = 263.462 + 0.144(Natuphos ®) + 0.014(Ronozyme ®) + 0.823 (Mutant U) + 0.711(AppA) + 0.718(AppA2)
$R^2 = 0.93$

| Relative Phytase Activity | Ratio (%) | Eq. To 500 U/kg Natuphos ® |
|---|---|---|
| Ronozyme ®: | (0.014/0.144) * 100 = 10 | 50 |
| Mutant U: | (0.823/0.144) * 100 = 572 | 2860 |

| -continued | | |
|---|---|---|
| AppA: | (0.711/0.144) * 100 = 494 | 2470 |
| AppA2: | (0.718/0.144) * 100 = 499 | 2495 |

At 500 U/kg, the yeast-expressed enzymes (Mutant U, AppA and AppA2) were more effective than Natuphos® or Ronozyme® (both enzymes are expressed in fungal expression systems) at improving the in vivo responses tested. For example, Mutant U, AppA and AppA2 were four times more effective than Natuphos® in releasing phosphate (see FIG. 3).

EXAMPLE 10

In Vivo Effects of Yeast-Expressed Phytases Fed to Pigs

The procedure was as described in Example 8 except that pigs (average initial weight of 10 kg) were fed the phytase-supplemented feed composition. The treatment groups were as follows:

Treatment Groups:
1) Basal diet (0.75 P; 0.60% Ca)
2) Same as 1+0.05% P from $KH_2PO_4$
3) Same as 1+0.10% P from $KH_2PO_4$
4) Same as 1+0.15% P from $KH_2PO_4$
5) Same as 1+400 U/kg phytase from Natuphos®
6) Same as 1+400 U/kg phytase from Mutant U phytase
7) Same as 1+400 U/kg AppA phytase
8) Same as 1+400 U/kg AppA2 phytase For the various treatment groups weight gain, feed to weight gain ratio, fibula ash weight, fibula ash weight as a percentage of dry fibula weight, and the percentage of bioavailable phosphate based on fibula ash weight were determined. The results were as follows:

TABLE 3

Pig Assay[a]

| | | Fibula Composition | | | |
|---|---|---|---|---|---|
| Treatment Groups | Weight gain, g/d | G:F, g/kg | Ash, % | Ash, mg | Bio-available P, %[b] |
| Basal Diet | 369 | 533 | 29.31 | 666 | |
| Same as 1 + 0.05% P from $KH_2PO_4$ | 435 | 576 | 32.83 | 766 | |
| Same as 1 + 0.10% P from $KH_2PO_4$ | 446 | 618 | 36.62 | 972 | |
| Same as 1 + 0.15% P from $KH_2PO_4$ | 509 | 660 | 36.57 | 1123 | |
| Same as 1 + 400 U/kg Natuphos ® phytase | 460 | 605 | 34.37 | 889 | 0.081 |
| Same as 1 + 400 U/kg Mutant U phytase | 458 | 645 | 35.45 | 961 | 0.116 |
| Same as 1 + 400 U/kg AppA phytase | 458 | 606 | 35.97 | 1035 | 0.136 |
| Same as 1 + 400 U/kg AppA2 phytase | 443 | 583 | 34.96 | 968 | 0.108 |
| Contrast | Significance (P-value) | | | | |
| Natuphos ® (treatment group (trt) 5) vs. yeast-expressed phytases (trt 6–8) | NS | NS | NS | 0.05 | 0.048 |
| Mutant U (trt 6) AppA vs. (trt 7) and AppA2 (trt 8) | 0.10 | 0.10 | NS | 0.001 | 0.239 |

[a]Data are means of ten replicates per treatment of individually housed pigs during a period of 23 days; average initial weight was 8.4 ± 0.2 kg.
[b]Percent bioavailable P calculations are estimates of P equivalency based on $KH_2PO_4$ standard curve (treatments 1–4). Calculations based on $KH_2PO_4$ standard curve where Y = fibula ash (mg) and X = supplemental or equivalent P intake (g): Y = 664.49 + 15.29X ($r^2 = 0.87$).

At 400 U/kg, the yeast-expressed enzymes (Mutant U, AppA, and AppA2) were more effective than Natuphos® (expressed in fungus) at improving the responses tested.

EXAMPLE 11

In Vivo Effects of Yeast-Expressed Phytases in Chicks

The procedure was as described in Example 8 except that the chicks had an average initial weight of 83 grams, and the treatment groups were as follows:

Treatment Groups:

| | |
|---|---|
| 1. | Basal Diet (0.10% P; 0.75% Ca) |
| 2. | Same as 1 + 0.05% P from $KH_2PO_4$ |
| 3. | Same as 1 + 0.10% P from $KH_2PO_4$ |
| 4. | Same as 1 + 0.15% P from $KH_2PO_4$ |
| 5. | Same as 1 + 500 U/kg Natuphos ® phytase (batch 1) |
| 6. | Same as 1 + 500 U/kg Natuphos ® phytase (batch 2) |
| 7. | Same as 1 + 1000 U/kg Natuphos ® phytase (batch 2) |
| 8. | Same as 1 + 500 U/kg Ronozyme ® phytase (batch 1) |
| 9. | Same as 1 + 500 U/kg Ronozyme ® phytase (batch 2) |
| 10. | Same as 1 + 1000 U/kg Ronozyme ® phytase (batch 2) |
| 11. | Same as 1 + 500 U/kg Mutant U phytase |
| 12. | Same as 1 + 500 U/kg AppA phytase |
| 13. | Same as 1 + 500 U/kg AppA2 phytase |
| 14. | Same as 1 + 500 U/kg AppA2 + novel promoter phytase (AppA2/p) |

The tables are as labeled in Example 8. The in vivo effects of phytase supplementation described in Example 8 were measured and the results were as follows:

Weight gain (g/c)

| | T1 | T2 | T3 | T4 | T5 | T6 | T7 | T8 | T9 | T10 | T11 | T12 | T13 | T14 |
|---|---|---|---|---|---|---|---|---|---|---|---|---|---|---|
| R1 | 152 | 252 | 295 | 299 | 215 | 235 | 241 | 223 | 256 | 254 | 325 | 308 | 322 | 314 |
| R2 | 199 | 238 | 290 | 332 | 206 | 210 | 256 | 237 | 212 | 243 | 312 | 316 | 309 | 306 |
| R3 | 163 | 257 | 297 | 347 | 235 | 254 | 250 | 215 | 218 | 246 | 324 | 309 | 313 | 335 |
| R4 | 176 | 262 | 288 | 330 | 242 | 250 | 288 | 228 | 195 | 223 | 329 | 318 | 310 | 317 |
| R5 | 190 | 257 | 295 | 356 | 193 | 230 | 288 | 218 | 214 | 259 | 306 | 307 | 314 | 317 |
| Mean | 176 | 253 | 293 | 333 | 218 | 236 | 265 | 224 | 219 | 245 | 319 | 312 | 314 | 318 |
| g/c/d | 12.6 | 18.1 | 20.9 | 23.8 | 15.6 | 16.9 | 18.9 | 16.0 | 15.6 | 17.5 | 22.8 | 22.3 | 22.4 | 22.7 |

Pooled SEM = 7
LSD = 19

Feed intake (g/c)

| | T1 | T2 | T3 | T4 | T5 | T6 | T7 | T8 | T9 | T10 | T11 | T12 | T13 | T14 |
|---|---|---|---|---|---|---|---|---|---|---|---|---|---|---|
| R1 | 279 | 373 | 431 | 424 | 347 | 386 | 352 | 359 | 284 | 321 | 435 | 429 | 447 | 424 |
| R2 | 335 | 352 | 407 | 441 | 333 | 340 | 375 | 363 | 325 | 368 | 395 | 441 | 427 | 465 |
| R3 | 291 | 374 | 419 | 472 | 369 | 400 | 381 | 330 | 348 | 367 | 439 | 459 | 440 | 472 |
| R4 | 292 | 386 | 400 | 457 | 366 | 370 | 405 | 358 | 328 | 356 | 451 | 473 | 421 | 441 |
| R5 | 344 | 374 | 427 | 483 | 341 | 370 | 450 | 336 | 344 | 394 | 425 | 420 | 449 | 445 |
| Mean | 308 | 372 | 417 | 455 | 351 | 373 | 393 | 349 | 326 | 361 | 429 | 444 | 437 | 449 |
| g/c/d | 22.0 | 26.6 | 29.8 | 32.5 | 25.1 | 26.6 | 28.1 | 24.9 | 23.3 | 25.8 | 30.6 | 31.7 | 31.2 | 32.1 |

Pooled SEM = 10
LSD = 28

Gain/feed (g/kg)

| | T1 | T2 | T3 | T4 | T5 | T6 | T7 | T8 | T9 | T10 | T11 | T12 | T13 | T14 |
|---|---|---|---|---|---|---|---|---|---|---|---|---|---|---|
| R1 | 544 | 674 | 684 | 705 | 618 | 608 | 684 | 621 | 676 | 793 | 747 | 718 | 719 | 742 |
| R2 | 593 | 676 | 713 | 752 | 617 | 616 | 682 | 653 | 651 | 659 | 790 | 716 | 722 | 657 |
| R3 | 558 | 686 | 709 | 736 | 636 | 635 | 656 | 650 | 626 | 671 | 737 | 673 | 713 | 708 |
| R4 | 601 | 680 | 720 | 723 | 662 | 677 | 711 | 637 | 594 | 627 | 729 | 673 | 737 | 719 |
| R5 | 551 | 685 | 690 | 737 | 565 | 622 | 641 | 649 | 624 | 658 | 721 | 732 | 700 | 712 |
| Mean | 569 | 680 | 703 | 731 | 620 | 632 | 675 | 642 | 634 | 682 | 745 | 702 | 718 | 708 |

Pooled SEM = 13
LSD = 37

Dry tibia weight (mg/c)

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| R1 | 671 | 886 | 1048 | 1002 | 919 | 840 | 912 | 825 | 891 | 831 | 1117 | 1041 | 1057 | 1091 |
| R2 | 815 | — | 1003 | 1298 | 752 | 765 | 906 | 865 | 756 | 916 | 1113 | 1152 | 1041 | 1070 |
| R3 | 730 | 884 | 1036 | 1296 | 849 | 942 | 937 | 864 | 849 | 816 | 1154 | 1017 | 1130 | 1220 |
| R4 | 698 | 911 | 931 | 1232 | 802 | 901 | 918 | 837 | 807 | 872 | 1163 | 1165 | 1047 | 1078 |

-continued

Dry tibia weight (mg/c)

|    | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| R5 | 773 | 929 | 1037 | 1266 | 793 | 845 | 867 | 768 | 825 | 962 | 1044 | 1054 | 1130 | 1140 |
| Mean | 737 | 903 | 1011 | 1219 | 823 | 859 | 908 | 832 | 826 | 879 | 1118 | 1086 | 1081 | 1120 |

Pooled SEM = 27
LSD = 77

Supplemental P intake (g)

|    | 1 | 2 | 3 | 4 |
|---|---|---|---|---|
| R1 | 0 | 0.187 | 0.431 | 0.636 |
| R2 | 0 | 0.176 | 0.407 | 0.661 |
| R3 | 0 | 0.187 | 0.419 | 0.708 |
| R4 | 0 | 0.193 | 0.400 | 0.685 |
| R5 | 0 | 0.187 | 0.427 | 0.724 |
| Mean | $0^d$ | $0.186^c$ | $0.417^b$ | $0.683^a$ |

Tibia ash (mg/c)

|    | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| R1 | 174 | 255 | 381 | 367 | 254 | 230 | 246 | 239 | 253 | 224 | 415 | 385 | 404 | 411 |
| R2 | 197 | 279 | 343 | 483 | 199 | 198 | 244 | 242 | 200 | 249 | 395 | 425 | 357 | 353 |
| R3 | 185 | 279 | 361 | 486 | 238 | 261 | 276 | 230 | 228 | 231 | 410 | 370 | 389 | 454 |
| R4 | 175 | 287 | 315 | 459 | 220 | 262 | 282 | 222 | 210 | 244 | 416 | 455 | 371 | 396 |
| R5 | 183 | 261 | 335 | 481 | 211 | 229 | 264 | 202 | 222 | 262 | 383 | 380 | 406 | 431 |
| Mean | 183 | 272 | 347 | 455 | 224 | 236 | 262 | 227 | 223 | 242 | 404 | 403 | 385 | 409 |

Pooled SEM = 12
LSD = 32

Tibia ash (%)

|    | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| R1 | 25.88 | 28.82 | 36.31 | 36.67 | 27.60 | 27.39 | 26.91 | 29.01 | 28.42 | 26.99 | 37.15 | 37.03 | 38.24 | 37.64 |
| R2 | 24.20 | — | 34.21 | 37.18 | 26.51 | 25.89 | 26.86 | 27.97 | 26.44 | 27.16 | 35.49 | 36.90 | 34.33 | 32.98 |
| R3 | 25.43 | 31.61 | 34.87 | 37.53 | 28.06 | 27.75 | 29.52 | 26.65 | 26.85 | 28.35 | 35.54 | 36.34 | 34.40 | 37.22 |
| R4 | 25.04 | 31.53 | 33.85 | 37.22 | 27.42 | 29.15 | 30.73 | 26.46 | 26.03 | 27.97 | 35.76 | 39.09 | 35.43 | 36.71 |
| R5 | 23.72 | 28.11 | 32.27 | 38.02 | 26.61 | 27.17 | 30.41 | 26.26 | 26.88 | 27.22 | 36.67 | 36.02 | 35.99 | 37.80 |
| Mean | 24.85 | 30.02 | 34.30 | 37.32 | 27.24 | 27.47 | 28.89 | 27.27 | 26.92 | 27.54 | 36.12 | 37.08 | 35.68 | 36.47 |

Pooled SEM = 0.57
LSD = 1.61

Phosphorus Equivalency Estimates

KH$_2$PO$_4$ Standard Curve: Y = tibia ash (mg)
X = supplemental or equivalent P intake (g)

Y = 187.9 + 393.4X $r^2$ = 0.95

For 500 U/kg Phytase activity

| (example calculations using tibia ash treatment means) | | % Bioavailable P |
|---|---|---|
| Natuphos ® 1: | (224 − 187.9)/393.4 = 0.092 g P from 351 g FI = | 0.026% |
| Natuphos ® 2: | (236 − 187.9)/393.4 = 0.122 g P from 373 g FI = | 0.033% |
| Ronozyme ® 1: | (227 − 187.9)/393.4 = 0.099 g P from 349 g FI = | 0.028% |
| Ronozyme ® 2: | (223 − 187.9)/393.4 = 0.089 g P from 326 g FI = | 0.027% |
| Mutant U: | (404 − 187.9)/393.4 = 0.549 g P from 429 g FI = | 0.128% |
| AppA: | (403 − 187.9)/393.4 = 0.547 g P from 444 g FI = | 0.123% |
| AppA2: | (385 − 187.9)/393.4 = 0.501 g P from 437 g FI = | 0.115% |
| AppA2/p: | (409 − 187.9)/393.4 = 0.562 g P from 449 g FI = | 0.125% |

Results from ANOVA (calculation performed for each pen of four birds; treatment legend on previous page)

| | Bioavailable P (%) | | | | | | | | | |
|---|---|---|---|---|---|---|---|---|---|---|
| | 5 | 6 | 7 | 8 | 9 | 10 | 11 | 12 | 13 | 14 |
| R1 | 0.048 | 0.028 | 0.042 | 0.036 | 0.058 | 0.029 | 0.133 | 0.117 | 0.123 | 0.138 |
| R2 | 0.008 | 0.008 | 0.038 | 0.038 | 0.009 | 0.042 | 0.133 | 0.137 | 0.101 | 0.090 |
| R3 | 0.035 | 0.047 | 0.059 | 0.032 | 0.029 | 0.030 | 0.129 | 0.101 | 0.116 | 0.143 |
| R4 | 0.022 | 0.051 | 0.059 | 0.024 | 0.017 | 0.040 | 0.144 | 0.111 | 0.111 | 0.120 |
| R5 | 0.017 | 0.028 | 0.043 | 0.011 | 0.025 | 0.048 | 0.117 | 0.116 | 0.123 | 0.139 |
| Mean | $0.026^c$ | $0.032^{bc}$ | $0.048^b$ | $0.028^c$ | $0.028^c$ | $0.038^{bc}$ | $0.128^a$ | $0.123^a$ | $0.115^a$ | $0.125^a$ |

Pooled SEM = 0.006
LSD = 0.018

At 500 U/kg, the yeast-expressed enzymes (Mutant U, AppA, AppA2, and AppA2/p) were more effective than Natuphos® or Ronozyme® at improving the in vivo responses tested including weight gain, feed to weight gain ratio, bone mass and mineral content, and percent bioavailable phosphate. The yeast-expressed enzymes were about four times more effective at increasing the level of bioavailable phosphate than either of the fungus-expressed enzymes.

EXAMPLE 12

In Vivo Effects of Yeast-Expressed Phytases Fed to Post-Molt Laying Hens

The procedure was as described in Example 8 except post-molt laying hens were tested, egg production and egg weight was determined, and the treatment groups and basal diet were as follows:

Treatments:
1. P-deficient corn-soybean meal basal diet (0.10% Pa; 3.8% Ca; 17% CP)
2. As 1+0.10% Pi from $KH_2PO_4$
3. As 1+150 U/kg r-AppA2 phytase
4. As 1+300 U/kg r-AppA2 phytase
5. As 1+10,000 U/kg r-AppA2 phytase

| Basal Diet: Ingredient | % |
|---|---|
| Corn | 63.65 |
| Soybean meal, dehulled | 25.65 |
| Limestone, ground | 9.80 |
| Salt | 0.40 |
| Mineral premix | 0.20 |
| Vitamin premix | 0.15 |
| DL-methionine, feed-grade | 0.10 |
| Choline chloride | 0.05 |

** Note:
Treatment 1 discontinued after week 4 due to egg production below 50%.

The following tables are labeled as described in Example 8 and some of the same responses as described in Example 8 were measured. The results show that AppA2 increases egg production and egg weight in post-molt laying hens.

Treatments:

1. P-deficient corn-soybean meal basal diet (0.10% pa; 3.8% Ca; 17% CP)
2. As 1 + 0.10% Pi from $KH_2PO_4$
3. As 1 + 150 U/kg r-AppA2 phytase
4. As 1 + 300 U/kg r-AppA2 phytase
5. As 1 + 10,000 U/kg r-AppA2 phytase

| Initial body weights (g; mean of 12 hens) | | | | | |
|---|---|---|---|---|---|
| | T1 | T2 | T3 | T4 | T5 |
| R1 | 1699 | 1792 | 1682 | 1790 | 1707 |
| R2 | 1785 | 1698 | 1734 | 1855 | 1694 |
| R3 | 1690 | 1665 | 1775 | 1724 | 1824 |
| R4 | 1688 | 1745 | 1739 | 1823 | 1760 |
| mean | 1716 | 1725 | 1733 | 1798 | 1746 |

Pooled SEM = 26
LSD = 78

| 4-wk body weights (g; mean of 12 hens) | | | | | |
|---|---|---|---|---|---|
| | T1 | T2 | T3 | T4 | T5 |
| R1 | 1566 | 1802 | 1763 | 1769 | 1748 |
| R2 | 1558 | 1734 | 1816 | 1860 | 1723 |
| R3 | 1633 | 1707 | 1744 | 1769 | 1850 |
| R4 | 1615 | 1749 | 1762 | 1827 | 1757 |
| mean | 1593 | 1748 | 1771 | 1806 | 1770 |

Pooled SEM = 21
LSD = 64

| 12-wk body weights (g; mean of 12 hens) | | | | | |
|---|---|---|---|---|---|
| | T1 | T2 | T3 | T4 | T5 |
| R1 | — | 1876 | 1831 | 1792 | 1781 |
| R2 | — | 1791 | 1775 | 1856 | 1791 |
| R3 | — | 1800 | 1765 | 1806 | 1933 |
| R4 | — | 1853 | 1814 | 1876 | 1815 |
| mean | — | 1830 | 1796 | 1833 | 1830 |

Pooled SEM = 24
LSD = 74

Treatments:

1. P-deficient corn-soybean meal basal diet (0.10% pa; 3.8% Ca; 17% CP)
2. As 1 + 0.10% Pi from $KH_2PO_4$
3. As 1 + 150 U/kg r-AppA2 phytase
4. As 1 + 300 U/kg r-AppA2 phytase
5. As 1 + 10,000 U/kg r-AppA2 phytase

| Feed intake (g/h/d)[1] | | | | | |
|---|---|---|---|---|---|
| | T1 | T2 | T3 | T4 | T5 |
| R1 | 89 | 118 | 122 | 115 | 116 |
| R2 | 92 | 125 | 114 | 122 | 119 |
| R3 | 89 | 117 | 118 | 116 | 124 |
| R4 | 94 | 123 | 119 | 115 | 123 |
| mean | 91[b] | 121[a] | 118[a] | 117[a] | 121[a] |

Pooled SEM = 2
LSD = 5
[1]Means are average daily feed intakes of hens for the first 4-wk period for treatment 1, and for the entire 12-wk period for treatments 2–5.

| Egg weights (g)[1] | | | | | |
|---|---|---|---|---|---|
| | T1 | T2 | T3 | T4 | T5 |
| R1 | 57.5 | 64.0 | 65.4 | 65.7 | 64.5 |
| R2 | 63.5 | 64.7 | 64.3 | 66.0 | 65.5 |
| R3 | 60.3 | 64.3 | 64.6 | 64.8 | 65.6 |
| R4 | 62.8 | 63.3 | 62.2 | 65.3 | 63.7 |
| mean | 61.0[b] | 64.1[a] | 64.1[a] | 65.5[a] | 64.8[a] |

Pooled SEM = 0.7
LSD = 2.2
[1]Means are average egg weights of hens for the first 4-wk period for treatment 1, and for the entire 12-wk period for treatments 2–5.

Treatments:
1. P-deficient corn-soybean meal basal diet (0.10% pa; 3.8% Ca; 17% CP)
2. As 1+0.10% Pi from $KH_2PO_4$
3. As 1+150 U/kg r-AppA2 phytase
4. As 1+300 U/kg r-AppA2 phytase
5. As 1+10,000 U/kg r-AppA2 phytase

| Egg production by week(%) | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| D1 | 75.3 | 55.7 | 36.0 | 22.9 | — | — | — | — | — | — | — | — |
| D2 | 88.4 | 90.8 | 88.1 | 87.8 | 88.4 | 85.4 | 86.0 | 81.8 | 80.4 | 79.8 | 80.7 | 78.3 |
| D3 | 84.5 | 85.1 | 83.3 | 85.1 | 83.3 | 82.1 | 83.6 | 79.2 | 77.4 | 77.4 | 79.5 | 76.5 |
| D4 | 86.6 | 86.3 | 83.9 | 82.4 | 82.1 | 84.5 | 81.5 | 77.4 | 78.0 | 74.7 | 73.8 | 72.0 |
| D5 | 82.4 | 83.3 | 83.6 | 84.8 | 80.7 | 81.3 | 82.7 | 78.6 | 80.1 | 78.9 | 76.8 | 72.6 |
| SEM | 3.0 | 3.2 | 3.4 | 3.5 | 3.3 | 3.2 | 3.2 | 4.1 | 3.4 | 4.5 | 3.5 | 3.9 |

| Egg production (%)[1] | | | | | |
|---|---|---|---|---|---|
| | T1 | T2 | T3 | T4 | T5 |
| R1 | 44.6 | 86.5 | 73.0 | 81.0 | 80.7 |
| R2 | 60.1 | 85.7 | 78.1 | 81.7 | 74.7 |
| R3 | 43.2 | 87.2 | 84.3 | 83.9 | 87.8 |
| R4 | 42.0 | 80.9 | 90.8 | 74.6 | 85.3 |
| mean | 47.5 | 85.1 | 81.6 | 80.3 | 82.1 |
| Least-squares means[2] | 53.8[b] | 81.2[a] | 80.7[a] | 77.8[a] | 82.9[a] |

Pooled SEM = 2.1
[1]Means are the average egg production of hens for the first 4-wk period for treatment 1, and for the entire i2-wk period for treatments 2–5.
[2]Due to variation in week 1 egg production (above), covariance was used to analyze overall egg production, with least-squares means showing the effect of the covariable.

EXAMPLE 13

In Vivo Effects of Yeast-Expressed Phytases Fed to Finishing Pigs

The procedure was as described in Example 8 except finishing pigs (i.e., gilts and barrows) were tested and the basal diet and treatment groups were as follows:

Treatments:
1. P-deficient corn-soybean meal basal diet
2. As 1+0.10% Pi from $KH_2PO_4$
3. As 1+250 FTU/kg r-AppA2 phytase
4. As 1+500 FTU/kg r-AppA2 phytase
5. As 1+1,000 FTU/kg r-AppA2 phytase
6. As 1+10,000 FTU/kg r-AppA2 phytase Basal Diets:

| | Weight range (kg) | |
|---|---|---|
| Ingredient | 50–80 | 80–120 |
| Cornstarch | to 100 | to 100 |
| Corn | 78.42 | 83.85 |
| Soybean meal, dehulled | 18.08 | 12.65 |
| Limestone, ground | 1.06 | 1.07 |
| Dicalcium phosphate | 0.16 | — |
| Trace mineral premix | 0.35 | 0.35 |
| Vitamin premix | 0.10 | 0.10 |
| L-Lysine-HCl, feed-grade | 0.16 | 0.11 |
| L-threonine, feed-grade | 0.02 | — |
| Antibiotic premix | 0.75 | 0.75 |
| Calculated composition (NRC, 1998) | | |
| Crude protein, % | 15.1 | 13.0 |

-continued

| | Weight range (kg) | |
|---|---|---|
| Ingredient | 50–80 | 80–120 |
| Lysine, total % | 0.88 | 0.69 |
| Calcium, % | 0.50 | 0.45 |
| Phosphorus, total % | 0.38 | 0.32 |
| Phosphorus, estimated bioavailable, % | 0.09 | 0.05 |
| ME, kcal/kg | 3293 | 3295 |

The following tables are labeled as described in Example 8 and some of the responses described in Example 8 were measured. Gain/feed ratio is shown rather than a feed/gain ratio.

The results show that AppA2 was as effective as phosphate at increasing bone mass and mineral content, and at improving the gain/feed ratio.

Treatments:
1. P-deficient corn-soybean meal basal diet
2. As 1+0.10% Pi from $KH_2PO_4$
3. As 1+250 FTU/kg r-AppA2 phytase
4. As 1+500 FTU/kg r-AppA2 phytase
5. As 1+1,000 FTU/kg r-AppA2 phytase
6. As 1+10,000 FTU/kg r-AppA2 phytase

| | Initial pig weights (kg) | | | | | | | | | | | |
|---|---|---|---|---|---|---|---|---|---|---|---|---|
| | Barrows | | | | | | Gilts | | | | | |
| | 1 | 2 | 3 | 4 | 5 | 6 | 1 | 2 | 3 | 4 | 5 | 6 |
| R1 | 52.2 | 52.8 | 53.0 | 51.8 | 52.0 | 51.8 | 51.2 | 50.8 | 52.2 | 52.2 | 51.3 | 52.4 |
| R2 | 51.0 | 51.1 | 51.7 | 50.3 | 51.6 | 50.4 | 49.6 | 49.6 | 50.3 | 50.0 | 50.4 | 50.8 |
| R3 | 48.2 | 49.6 | 49.8 | 49.6 | 50.1 | 49.2 | 48.1 | 49.6 | 47.9 | 47.1 | 48.8 | 48.4 |
| R4 | 46.4 | 46.5 | 46.5 | 46.9 | 47.4 | 47.9 | 45.9 | 45.4 | 44.3 | 46.6 | 46.5 | 45.7 |
| R5 | 52.0 | 44.1 | 51.0 | 52.4 | 46.4 | 50.7 | 43.4 | 43.9 | 44.0 | 43.1 | 44.1 | 44.0 |
| mean | 50.0 | 48.8 | 50.4 | 50.2 | 49.5 | 50.0 | 47.6 | 47.9 | 47.7 | 47.8 | 48.2 | 48.3 |

Pooled SEM = 0.4

| | Phase-switch pig weights (kg) | | | | | | | | | | | |
|---|---|---|---|---|---|---|---|---|---|---|---|---|
| | Barrows | | | | | | Gilts | | | | | |
| | 1 | 2 | 3 | 4 | 5 | 6 | 1 | 2 | 3 | 4 | 5 | 6 |
| R1 | 78.8 | 83.0 | 85.0 | 76.0 | 79.6 | 79.2 | 79.7 | 80.1 | 88.6 | 84.1 | 83.1 | 89.6 |
| R2 | 76.8 | 80.6 | 86.9 | 79.9 | 82.2 | 83.8 | 80.0 | 83.5 | 87.7 | 84.5 | 87.3 | 83.5 |
| R3 | 73.7 | 79.8 | 77.1 | 79.1 | 79.0 | 75.9 | 77.1 | 77.6 | 81.3 | 79.9 | 82.6 | 82.4 |
| R4 | 82.3 | 82.5 | 79.2 | 79.1 | 84.4 | 84.5 | 74.7 | 78.1 | 73.9 | 84.6 | 78.9 | 79.1 |
| R5 | 84.5 | 78.5 | 84.7 | 83.2 | 85.3 | 85.2 | 83.3 | 80.5 | 84.4 | 87.2 | 81.7 | 82.5 |
| mean | 79.2 | 80.9 | 82.6 | 79.5 | 82.1 | 81.7 | 78.9 | 79.9 | 83.2 | 83.4 | 82.7 | 83.4 |

Pooled SEM = 0.8

| | Final pig weights (kg) | | | | | | | | | | | |
|---|---|---|---|---|---|---|---|---|---|---|---|---|
| | Barrows | | | | | | Gilts | | | | | |
| | 1 | 2 | 3 | 4 | 5 | 6 | 1 | 2 | 3 | 4 | 5 | 6 |
| R1 | 111.3 | 121.2 | 121.9 | 115.9 | 112.9 | 111.1 | 105.9 | 109.5 | 119.9 | 116.1 | 105.4 | 130.1 |
| R2 | 111.5 | 119.6 | 132.7 | 111.9 | 121.3 | 116.3 | 105.8 | 115.6 | 118.3 | 115.3 | 123.3 | 112.5 |
| R3 | 115.9 | 126.4 | 117.1 | 119.9 | 114.0 | 120.7 | 104.9 | 107.9 | 123.6 | 125.2 | 127.1 | 130.8 |
| R4 | 116.6 | 117.9 | 110.0 | 110.0 | 119.7 | 122.1 | 120.2 | 121.6 | 117.9 | 127.7 | 109.3 | 123.0 |
| R5 | 118.3 | 111.6 | 122.3 | 114.2 | 123.0 | 117.1 | 115.2 | 110.4 | 119.2 | 135.1 | 119.1 | 117.1 |
| mean | 114.7 | 119.3 | 120.8 | 114.4 | 118.2 | 117.5 | 110.3 | 113.0 | 119.8 | 123.9 | 116.8 | 122.7 |

Pooled SEM = 3.0 (Sex × Diet, P < 0.10)
Contrasts: Sex × Pi (2) vs Phytase (3–6), P < 0.05.

Treatments:
1. P-deficient corn-soybean meal basal diet
2. As 1+0.10% Pi from $KH_2PO_4$
3. As 1+250 FTU/kg r-AppA2 phytase
4. As 1+500 FTU/kg r-AppA2 phytase
5. As 1+1,000 FTU/kg r-AppA2 phytase
6. As 1+10,000 FTU/kg r-AppA2 phytase

| | Weight gain, initial-switch (g/d) | | | | | | | | | | | |
|---|---|---|---|---|---|---|---|---|---|---|---|---|
| | Barrows | | | | | | Gilts | | | | | |
| | 1 | 2 | 3 | 4 | 5 | 6 | 1 | 2 | 3 | 4 | 5 | 6 |
| R1 | 1024 | 1163 | 1233 | 931 | 1061 | 1055 | 816 | 836 | 1040 | 911 | 909 | 1063 |
| R2 | 993 | 1135 | 1353 | 1140 | 1178 | 1283 | 867 | 966 | 1068 | 986 | 1055 | 936 |
| R3 | 979 | 1162 | 1048 | 1131 | 1109 | 1028 | 829 | 801 | 955 | 935 | 965 | 971 |
| R4 | 1025 | 1028 | 936 | 921 | 1057 | 1046 | 822 | 936 | 847 | 1001 | 925 | 952 |
| R5 | 931 | 983 | 963 | 881 | 1109 | 984 | 950 | 870 | 962 | 1048 | 895 | 918 |
| mean | 990 | 1094 | 1107 | 1001 | 1103 | 1079 | 857 | 882 | 974 | 976 | 950 | 968 |

Pooled SEM = 0.24
Contrasts: Barrows (Ba) vs Gilts (Gi), $P < 0.01$; 1 vs 2–6, $P < 0.01$

| | Weight gain, switch-final (g/d) | | | | | | | | | | | |
|---|---|---|---|---|---|---|---|---|---|---|---|---|
| | Barrows | | | | | | Gilts | | | | | |
| | 1 | 2 | 3 | 4 | 5 | 6 | 1 | 2 | 3 | 4 | 5 | 6 |
| R1 | 832 | 979 | 945 | 1023 | 855 | 818 | 706 | 794 | 844 | 865 | 604 | 1095 |
| R2 | 890 | 1000 | 1174 | 822 | 1001 | 833 | 688 | 874 | 835 | 830 | 974 | 784 |
| R3 | 919 | 1013 | 870 | 889 | 762 | 974 | 545 | 593 | 829 | 888 | 871 | 949 |
| R4 | 927 | 971 | 832 | 833 | 954 | 1015 | 893 | 854 | 861 | 904 | 596 | 862 |
| R5 | 912 | 895 | 1018 | 836 | 1020 | 864 | 531 | 499 | 581 | 798 | 624 | 577 |
| mean | 896 | 972 | 968 | 881 | 918 | 901 | 673 | 723 | 790 | 857 | 734 | 853 |

Pooled SEM = 37
Contrasts: Ba vs Gi, $P < 0.05$

| | Weight gain, overall (g/d) | | | | | | | | | | | |
|---|---|---|---|---|---|---|---|---|---|---|---|---|
| | Barrows | | | | | | Gilts | | | | | |
| | 1 | 2 | 3 | 4 | 5 | 6 | 1 | 2 | 3 | 4 | 5 | 6 |
| R1 | 909 | 1053 | 1060 | 986 | 937 | 913 | 760 | 814 | 940 | 887 | 752 | 1079 |
| R2 | 931 | 1054 | 1246 | 949 | 1072 | 1013 | 775 | 919 | 948 | 906 | 1013 | 858 |
| R3 | 941 | 1066 | 934 | 976 | 888 | 993 | 660 | 678 | 880 | 907 | 910 | 958 |
| R4 | 975 | 1006 | 882 | 876 | 1004 | 1030 | 864 | 887 | 855 | 944 | 730 | 898 |
| R5 | 922 | 938 | 992 | 858 | 1063 | 922 | 703 | 652 | 738 | 901 | 735 | 717 |
| mean | 935 | 1023 | 1023 | 929 | 993 | 974 | 752 | 790 | 872 | 909 | 828 | 902 |

Pooled SEM = 38 (Sex × diet, $P < 0.10$)
Contrasts: Sex × Pi (2) vs Phytase (3–6), $P < 0.05$ Treatments:
1. P-deficient corn-soybean meal basal diet
2. As 1+0.10% Pi from $KH_2PO_4$
3. As 1+250 FTU/kg r-AppA2 phytase
4. As 1+500 FTU/kg r-AppA2 phytase
5. As 1+1,000 FTU/kg r-AppA2 phytase
6. As 1+10,000 FTU/kg r-AppA2 phytase

| | Feed intake, initial-switch (g/d) | | | | | | | | | | | |
|---|---|---|---|---|---|---|---|---|---|---|---|---|
| | Barrows | | | | | | Gilts | | | | | |
| | 1 | 2 | 3 | 4 | 5 | 6 | 1 | 2 | 3 | 4 | 5 | 6 |
| R1 | 2670 | 2733 | 2947 | 2271 | 2516 | 2448 | 2152 | 2029 | 2437 | 2074 | 2211 | 2579 |
| R2 | 2541 | 2564 | 2940 | 2590 | 2484 | 2899 | 2425 | 2068 | 2543 | 2326 | 2363 | 1979 |
| R3 | 2277 | 2499 | 2338 | 2385 | 2601 | 2066 | 2134 | 2020 | 2388 | 2168 | 2207 | 2093 |

-continued

Feed intake, initial-switch (g/d)

| | Barrows | | | | | | Gilts | | | | | |
|---|---|---|---|---|---|---|---|---|---|---|---|---|
| | 1 | 2 | 3 | 4 | 5 | 6 | 1 | 2 | 3 | 4 | 5 | 6 |
| R4 | 2371 | 2370 | 2311 | 2206 | 2457 | 2077 | 2104 | 2230 | 1919 | 2139 | 2260 | 2215 |
| R5 | 2665 | 2312 | 2603 | 2308 | 2696 | 2366 | 2008 | 1289 | 2396 | 2237 | 1494 | 1866 |
| mean | 2505 | 2496 | 2628 | 2352 | 2551 | 2371 | 2165 | 1927 | 2337 | 2189 | 2107 | 2146 |

Pooled SEM = 67
Contrasts: Ba vs Gi, $P < 0.01$

Feed intake, switch-final (g/d)

| | Barrows | | | | | | Gilts | | | | | |
|---|---|---|---|---|---|---|---|---|---|---|---|---|
| | 1 | 2 | 3 | 4 | 5 | 6 | 1 | 2 | 3 | 4 | 5 | 6 |
| R1 | 3181 | 3427 | 3559 | 3270 | 2962 | 2918 | 2443 | 2615 | 2890 | 2651 | 2094 | 3739 |
| R2 | 2922 | 3039 | 3833 | 3011 | 3141 | 3147 | 2481 | 2652 | 2936 | 2796 | 3316 | 2565 |
| R3 | 3087 | 3330 | 2847 | 2877 | 2904 | 2686 | 2241 | 2110 | 2849 | 2692 | 2820 | 2952 |
| R4 | 2978 | 2945 | 2872 | 2646 | 3104 | 2876 | 2935 | 2946 | 2373 | 2685 | 2481 | 2836 |
| R5 | 3244 | 2958 | 3549 | 3106 | 3517 | 3008 | 2307 | 1747 | 2728 | 2947 | 2224 | 2385 |
| mean | 3082 | 3140 | 3332 | 2982 | 3126 | 2926 | 2482 | 2414 | 2755 | 2754 | 2587 | 2895 |

Pooled SEM = 105
Contrasts: Ba vs Gi, $P < 0.01$

Feed intake, overall (g/d)

| | Barrows | | | | | | Gilts | | | | | |
|---|---|---|---|---|---|---|---|---|---|---|---|---|
| | 1 | 2 | 3 | 4 | 5 | 6 | 1 | 2 | 3 | 4 | 5 | 6 |
| R1 | 2977 | 3149 | 3314 | 2870 | 2784 | 2726 | 2302 | 2330 | 2670 | 2370 | 2151 | 3175 |
| R2 | 2770 | 2849 | 3476 | 2842 | 2878 | 3048 | 2454 | 2368 | 2745 | 2568 | 2853 | 2280 |
| R3 | 2794 | 3030 | 2663 | 2699 | 2794 | 2462 | 2197 | 2073 | 2661 | 2479 | 2571 | 2603 |
| R4 | 2683 | 2632 | 2599 | 2432 | 2790 | 2488 | 2597 | 2655 | 2188 | 2463 | 2391 | 2583 |
| R5 | 2963 | 2644 | 3089 | 2718 | 3118 | 2696 | 2184 | 1559 | 2591 | 2654 | 1993 | 2171 |
| mean | 2837 | 2861 | 3028 | 2712 | 2873 | 2684 | 2347 | 2197 | 2571 | 2507 | 2378 | 2562 |

Pooled SEM = 81
Contrasts: Ba vs GI, $P < 0.01$

Treatments:
1. P-deficient corn-soybean meal basal diet
2. As 1+0. 10% Pi from $KH_2PO_4$
3. As 1+250 FTU/kg r-AppA2 phytase
4. As 1+500 FTU/kg r-AppA2 phytase
5. As 1+1,000 FTU/kg r-AppA2 phytase
6. As 1+10,000 FTU/kg r-AppA2 phytase Gain/feed, initial-switch (g/kg)

| | Barrows | | | | | | Gilts | | | | | |
|---|---|---|---|---|---|---|---|---|---|---|---|---|
| | 1 | 2 | 3 | 4 | 5 | 6 | 1 | 2 | 3 | 4 | 5 | 6 |
| R1 | 383 | 425 | 418 | 410 | 421 | 431 | 379 | 412 | 427 | 439 | 411 | 412 |
| R2 | 391 | 443 | 460 | 440 | 474 | 442 | 357 | 467 | 420 | 424 | 447 | 473 |
| R3 | 430 | 465 | 448 | 474 | 427 | 498 | 388 | 396 | 400 | 431 | 437 | 464 |
| R4 | 432 | 434 | 405 | 418 | 430 | 504 | 390 | 420 | 441 | 468 | 409 | 430 |

-continued

Gain/feed, initial-switch (g/kg)

| | Barrows | | | | | | Gilts | | | | | |
|---|---|---|---|---|---|---|---|---|---|---|---|---|
| | 1 | 2 | 3 | 4 | 5 | 6 | 1 | 2 | 3 | 4 | 5 | 6 |
| R5 | 349 | 425 | 370 | 382 | 411 | 416 | 473 | 675 | 402 | 469 | 599 | 492 |
| mean | 397 | 438 | 420 | 425 | 433 | 458 | 397 | 474 | 418 | 446 | 461 | 454 |

Pooled SEM = 12
Contrasts: 1 vs. 2–6, $P < 0.01$; 3 vs 4–6, $P < 0.10$

Gain/feed, switch-final (g/d)

| | Barrows | | | | | | Gilts | | | | | |
|---|---|---|---|---|---|---|---|---|---|---|---|---|
| | 1 | 2 | 3 | 4 | 5 | 6 | 1 | 2 | 3 | 4 | 5 | 6 |
| R1 | 262 | 286 | 265 | 313 | 289 | 281 | 289 | 304 | 292 | 326 | 289 | 293 |
| R2 | 305 | 329 | 306 | 273 | 319 | 265 | 277 | 329 | 285 | 297 | 294 | 306 |
| R3 | 298 | 304 | 307 | 309 | 262 | 363 | 243 | 281 | 291 | 330 | 309 | 321 |
| R4 | 311 | 329 | 290 | 315 | 307 | 353 | 304 | 290 | 363 | 337 | 240 | 304 |
| R5 | 281 | 303 | 287 | 269 | 290 | 287 | 230 | 285 | 213 | 271 | 281 | 242 |
| mean | 291 | 310 | 291 | 296 | 293 | 310 | 269 | 298 | 289 | 312 | 283 | 293 |

Pooled SEM = 8

Gain/feed overall (g/d)

| | Barrows | | | | | | Gilts | | | | | |
|---|---|---|---|---|---|---|---|---|---|---|---|---|
| | 1 | 2 | 3 | 4 | 5 | 6 | 1 | 2 | 3 | 4 | 5 | 6 |
| R1 | 305 | 334 | 320 | 344 | 337 | 335 | 330 | 349 | 352 | 374 | 350 | 340 |
| R2 | 336 | 370 | 358 | 334 | 372 | 332 | 316 | 388 | 345 | 353 | 355 | 376 |
| R3 | 337 | 352 | 351 | 362 | 318 | 403 | 301 | 327 | 331 | 366 | 354 | 368 |
| R4 | 363 | 381 | 339 | 361 | 360 | 414 | 333 | 334 | 391 | 383 | 305 | 348 |
| R5 | 311 | 355 | 321 | 316 | 341 | 342 | 322 | 418 | 285 | 340 | 382 | 330 |
| mean | 331 | 358 | 338 | 343 | 346 | 365 | 320 | 363 | 341 | 363 | 349 | 352 |

Pooled SEM = 8
Contrasts: 1 vs 2–6, $P < 0.01$

Treatments:
1. P-deficient corn-soybean meal basal diet
2. As 1+0.10% Pi from $KH_2PO_4$
3. As 1+250 FTU/kg r-AppA2 phytase
4. As 1+500 FTU/kg r-AppA2 phytase
5. As 1+1,000 FTU/kg r-AppA2 phytase
6. As 1+10,000 FTU/kg r-AppA2 phytase

Fibula Dry Weight (g)

| | Barrows | | | | | | Gilts | | | | | |
|---|---|---|---|---|---|---|---|---|---|---|---|---|
| | 1 | 2 | 3 | 4 | 5 | 6 | 1 | 2 | 3 | 4 | 5 | 6 |
| R1 | 8.18 | 10.90 | 11.45 | 12.11 | 10.08 | 12.08 | 7.54 | 10.95 | 9.92 | 9.42 | 9.87 | 11.29 |
| R2 | 8.84 | 11.74 | 8.66 | 10.98 | 11.21 | 11.66 | 7.96 | 8.81 | 9.33 | 11.41 | 10.70 | 12.73 |
| R3 | 8.54 | 11.29 | 9.81 | 11.90 | 10.10 | 12.77 | 8.62 | 10.25 | 9.94 | 10.50 | 11.86 | 12.46 |
| R4 | 9.82 | 10.69 | 9.06 | 10.22 | 11.05 | 12.40 | 8.26 | 11.61 | 9.67 | 10.92 | 10.91 | 10.49 |
| R5 | 7.88 | 8.88 | 10.33 | 10.51 | 12.01 | 11.26 | 7.68 | 9.51 | 11.16 | 11.48 | 10.10 | 11.44 |
| mean | 8.65 | 10.70 | 9.86 | 11.14 | 10.89 | 12.03 | 8.01 | 10.23 | 10.00 | 10.75 | 10.69 | 11.68 |

Pooled SEM = 0.27
Contrasts: 1 vs 2–6, $P < 0.01$; 3 vs 4–6, $P < 0.01$

| | Fibula Ash Weight (g) | | | | | | | | | | | |
|---|---|---|---|---|---|---|---|---|---|---|---|---|
| | Barrows | | | | | | Gilts | | | | | |
| | 1 | 2 | 3 | 4 | 5 | 6 | 1 | 2 | 3 | 4 | 5 | 6 |
| R1 | 4.37 | 6.32 | 6.34 | 6.90 | 6.03 | 6.94 | 4.06 | 6.42 | 5.21 | 5.33 | 5.61 | 6.78 |
| R2 | 4.26 | 7.05 | 5.12 | 6.49 | 6.24 | 6.80 | 4.36 | 5.18 | 5.51 | 6.25 | 6.21 | 7.16 |
| R3 | 4.51 | 6.54 | 5.78 | 7.17 | 5.81 | 7.49 | 4.35 | 5.91 | 6.11 | 5.79 | 6.93 | 7.23 |
| R4 | 5.34 | 6.35 | 5.19 | 5.90 | 6.73 | 7.33 | 4.28 | 7.13 | 5.66 | 6.35 | 6.56 | 6.22 |
| R5 | 4.37 | 5.22 | 6.02 | 6.34 | 7.06 | 6.64 | 3.91 | 5.64 | 7.02 | 6.25 | 5.88 | 6.93 |
| mean | 4.57 | 6.30 | 5.69 | 6.56 | 6.37 | 7.04 | 4.19 | 6.06 | 5.90 | 5.99 | 6.24 | 6.86 |

Pooled SEM = 0.17
Contrasts: Ba vs Gi, $P < 0.10$; 1 vs 2–6, $P < 0.01$; 3 vs 4–6, $P < 0.01$; 4 vs 5–6, $P < 0.10$; 5 vs 6, $P < 0.01$

| | Fibula Ash Percent (%) | | | | | | | | | | | |
|---|---|---|---|---|---|---|---|---|---|---|---|---|
| | Barrows | | | | | | Gilts | | | | | |
| | 1 | 2 | 3 | 4 | 5 | 6 | 1 | 2 | 3 | 4 | 5 | 6 |
| R1 | 53.42 | 57.98 | 55.37 | 56.98 | 59.82 | 57.45 | 53.85 | 58.63 | 52.52 | 56.58 | 56.84 | 60.05 |
| R2 | 48.19 | 60.05 | 59.12 | 59.11 | 55.66 | 58.32 | 54.77 | 58.80 | 59.06 | 54.78 | 58.04 | 56.25 |
| R3 | 52.81 | 57.93 | 58.92 | 60.25 | 57.52 | 58.65 | 50.46 | 57.66 | 61.47 | 55.14 | 58.43 | 58.03 |
| R4 | 54.38 | 59.40 | 57.28 | 57.73 | 60.90 | 59.11 | 51.82 | 61.41 | 58.53 | 58.15 | 60.13 | 59.29 |
| R5 | 55.46 | 58.78 | 58.28 | 60.32 | 58.78 | 58.97 | 50.91 | 59.31 | 62.90 | 54.44 | 58.22 | 60.58 |
| mean | 52.85 | 58.83 | 57.79 | 58.88 | 58.54 | 58.50 | 52.36 | 59.16 | 58.90 | 55.82 | 58.33 | 58.84 |

Pooled SEM = 0.65
Contrasts: 1 vs 2–6, $P < 0.01$

Treatments:
1. P-deficient corn-soybean meal basal diet
2. As 1+0.10% Pi from $KH_2PO_4$
3. As 1+250 FTU/kg r-AppA2 phytase
4. As 1+500 FTU/kg r-AppA2 phytase
5. As 1+1,000 FTU/kg r-AppA2 phytase
6. As 1+10,000 FTU/kg r-AppA2 phytase

| | Metatarsal Dry Weight (g) | | | | | | | | | | | |
|---|---|---|---|---|---|---|---|---|---|---|---|---|
| | Barrows | | | | | | Gilts | | | | | |
| | 1 | 2 | 3 | 4 | 5 | 6 | 1 | 2 | 3 | 4 | 5 | 6 |
| R1 | 11.42 | 14.03 | 15.84 | 15.36 | 14.43 | 13.85 | 11.77 | 15.90 | 16.00 | 15.48 | 12.65 | 15.05 |
| R2 | 11.89 | 14.52 | 13.27 | 14.26 | 13.73 | 15.06 | 11.66 | 13.74 | 14.14 | 14.19 | 13.75 | 14.87 |
| R3 | 14.01 | 14.45 | 13.20 | 13.99 | 14.91 | 17.43 | 10.52 | 12.20 | 11.95 | 16.31 | 17.53 | 18.03 |
| R4 | 12.25 | 14.38 | 12.54 | 15.99 | 15.26 | 17.01 | 11.68 | 13.49 | 13.16 | 14.20 | 12.77 | 14.23 |
| R5 | 12.55 | 13.30 | 14.30 | 14.36 | 17.79 | 14.29 | 11.26 | 12.76 | 12.47 | 16.93 | 12.78 | 13.10 |
| mean | 12.42 | 14.14 | 13.83 | 14.79 | 15.22 | 15.53 | 11.38 | 13.62 | 13.54 | 15.42 | 13.90 | 14.88 |

Pooled SEM = 0.44
Contrasts: 1 vs 2–6, $P < 0.01$; 3 vs 4–6, $P < 0.05$

| | Metatarsal Ash Weight (g) | | | | | | | | | | | |
|---|---|---|---|---|---|---|---|---|---|---|---|---|
| | Barrows | | | | | | Gilts | | | | | |
| | 1 | 2 | 3 | 4 | 5 | 6 | 1 | 2 | 3 | 4 | 5 | 6 |
| R1 | 5.28 | 6.59 | 7.97 | 6.93 | 6.74 | 6.86 | 4.74 | 7.21 | 6.72 | 7.09 | 6.07 | 7.50 |
| R2 | 6.81 | 7.10 | 5.94 | 6.74 | 6.32 | 7.44 | 4.84 | 6.28 | 6.40 | 6.55 | 6.71 | 7.07 |
| R3 | 4.82 | 6.95 | 6.41 | 6.77 | 6.72 | 7.88 | 4.82 | 5.59 | 6.67 | 6.99 | 8.13 | 8.11 |

-continued

Metatarsal Ash Weight (g)

| | Barrows | | | | | | Gilts | | | | | |
|---|---|---|---|---|---|---|---|---|---|---|---|---|
| | 1 | 2 | 3 | 4 | 5 | 6 | 1 | 2 | 3 | 4 | 5 | 6 |
| R4 | 4.83 | 6.81 | 6.26 | 7.73 | 7.88 | 7.48 | 4.86 | 7.27 | 5.92 | 7.15 | 6.97 | 7.13 |
| R5 | 5.20 | 5.75 | 7.22 | 6.99 | 8.33 | 7.14 | 5.24 | 6.61 | 6.65 | 7.07 | 6.04 | 6.55 |
| mean | 5.39 | 6.64 | 6.76 | 7.03 | 7.20 | 7.36 | 4.90 | 6.59 | 6.47 | 6.97 | 6.78 | 7.27 |

Pooled SEM = 0.18
Contrasts: 1 vs 2–6, $P < 0.01$; 3 vs 4–6, $P < 0.05$

Metatarsal Ash Percent (%)

| | Barrows | | | | | | Gilts | | | | | |
|---|---|---|---|---|---|---|---|---|---|---|---|---|
| | 1 | 2 | 3 | 4 | 5 | 6 | 1 | 2 | 3 | 4 | 5 | 6 |
| R1 | 46.25 | 46.99 | 50.31 | 45.15 | 46.75 | 49.56 | 40.22 | 45.37 | 42.01 | 45.80 | 47.96 | 49.84 |
| R2 | 39.90 | 48.90 | 44.75 | 47.16 | 46.02 | 49.39 | 41.50 | 45.72 | 45.27 | 46.18 | 48.80 | 47.55 |
| R3 | 34.38 | 48.12 | 48.59 | 48.36 | 45.09 | 45.18 | 45.84 | 45.78 | 55.84 | 42.87 | 46.39 | 47.35 |
| R4 | 39.44 | 47.27 | 49.89 | 48.36 | 51.65 | 43.98 | 41.63 | 53.93 | 44.97 | 50.32 | 54.59 | 50.11 |
| R5 | 41.44 | 43.26 | 50.50 | 48.69 | 46.81 | 49.95 | 46.50 | 51.82 | 53.33 | 41.74 | 47.28 | 50.00 |
| mean | 40.28 | 46.91 | 48.81 | 47.54 | 47.26 | 47.61 | 43.14 | 48.52 | 48.28 | 45.38 | 49.00 | 48.97 |

Pooled SEM = 1.05
Contrasts: 1 vs 2–6, $P < 0.01$

EXAMPLE 14

In Vivo Effects of Yeast-Expressed Phytases Fed to Pigs

The procedure was as described in Example 8 except that the treatment groups were as follows:

| | 28-day period |
|---|---|
| 1. | Basal – .08% available phosphorus |
| 2. | Basal + .05 phosphorus from monosodium phosphate |
| 3. | Basal + .10 phosphorus from monosodium phosphate |
| 4. | Basal + .15 phosphorus from monosodium phosphate |
| 5. | Basal + 250 FTU/kg experimental phytase product |
| 6. | Basal + 500 FTU/kg experimental phytase product |
| 7. | Basal + 1,000 FTU/kg experimental phytase product |
| 8. | Basal + 2,000 FTU/kg experimental phytase product |
| 9. | Basal + Natuphos ® 500 FTU/kg |

The results are shown in the following table. The results show that AppA2 increases bone mass and mineral content and improves the gain/feed ratio as effectively as phosphate.

Effect of phytase supplementation on pig growth performance and bone ash[a]

| Added $NaH_2PO_4H_2O$[b] Phytase units/g[c] | 0.00 | 0.05 | 0.10 | 0.15 | 250 | 500 | 1,000 | 2,000 | 500 BASF | S.E. |
|---|---|---|---|---|---|---|---|---|---|---|
| Daily gain, kg[i,j] | 0.35[g] | 0.39[fg] | 0.46[de] | 0.49[d] | 0.38[g] | 0.42[el] | 0.47[d] | 0.49[d] | 0.42[l] | 0.01 |
| Daily feed intake, kg[j] | 0.75[f] | 0.75[f] | 0.81[def] | 0.85[d] | 0.77[ef] | 0.79[def] | 0.83[def] | 0.85[d] | 0.85[de] | 0.07 |
| G:F[i,j,k] | 0.48[f] | 0.53[de] | 0.57[d] | 0.58[d] | 0.50[ef] | 0.54[de] | 0.57[d] | 0.57[d] | 0.49[ef] | 0.02 |
| Fibula ash, g[i,j] | 0.57[h] | 0.65[gh] | 0.77[f] | 0.88[e] | 0.59[h] | 0.72[f] | 0.85[e] | 0.97[d] | 0.70[fg] | 0.03 |
| Fibula ash, %[i,j] | 34.6[h] | 36.0[gh] | 37.8[g] | 41.5[de] | 33.9[h] | 38.2[fg] | 40.4[ef] | 42.6[d] | 38.5[f] | 0.84 |
| % Available P[l] | 18.43[g] | — | — | — | 22.56[g] | 38.31[f] | 53.56[e] | 66.71[d] | 34.47[f] | 4.07 |
| aP Intake, g/d[i,j,l] | 0.58[g] | 0.92[g] | 1.45[f] | 1.92[e] | 0.68[g] | 1.22[f] | 1.81[e] | 2.31[d] | 1.17[f] | 0.13 |
| Supplemental aP Intake, g/d[i,j,m] | 0.02[h] | 0.34[gh] | 0.84[f] | 1.27[e] | 0.12[h] | 0.62[fg] | 1.17[e] | 1.64[d] | 0.57[fg] | 0.13 |

[a]Six replications of two pigs per pen for performance data; six replications of two pigs per pen for bone data except for the treatment with phytase added at 500 units/g, which has five replications.
[b]Added P from monosodium phosphate ($NaH_2PO_4H_2O$) to the basal diet.
[c]Supplemental phytase added to the basal diet.
[d,e,f,g,h]Means Within a row without common superscripts differ ($P < 0.05$).
[i]Linear effect of added P from monosodium phosphate ($P < 0.001$).
[j]Linear effect of supplemental phytase ($P < 0.001$).
[k]UF phytase v. BASF phytase ($P < 0.07$)
[l]Assumes that the P in corn, soybean meal, and monosodium phosphate is 11.25, and 100% available, respectively.
[m]Assumes that the P in monosodium phosphate is 100% available.

EXAMPLE 15

In Vivo Effects of Yeast-Expressed Phytases Fed to Chicks and Pigs

The procedure for the studies summarized in the following tables was as described in Example 8. The treatment groups are shown in each table and the basal diet compositions are shown in the following table (see next page). The results show that AppA2 (ECP) is as effective as phosphate in improving the gain/feed ratio and in increasing bone mass and mineral content. The results also show that AppA2 is more effective than Natuphos® and Ronozyme® at increasing bioavailable phosphate. Furthermore, the results show that AppA2 increases egg weight and egg production in laying hens as effectively as phosphate.

Assessment of relative phosphorus bioavailability in chicks as affected by two different phytase enzymes (Chick assay 1)[a].

| Diet | Weight gain, g | Gain/feed, g/kg | Tibia ash % | Tibia ash mg | Bioavailable P, % |
|---|---|---|---|---|---|
| 1. Basal diet | 259[e] | 617[d] | 28.1[f] | 264[f] | — |
| 2. As 1 + 0.05% P$_i$ (KH$_2$PO$_4$) | 290[d] | 654[e] | 32.2[d] | 311[e] | — |
| 3. As 1 + 0.10% P$_i$ (KH$_2$PO$_4$) | 323[c] | 639[cd] | 36.4[c] | 414[d] | — |
| 4. As 1 + 500 FTU/kg Natuphos® | 289[d] | 666[e] | 30.0[e] | 293[e] | 0.027[d] |

Percentage composition of diets (as-fed basis).

| Ingredient | Chick assays | Young pig assay | Finishing pig assay 50–80 kg | Finishing pig assay 80–120 kg | Laying hen assay |
|---|---|---|---|---|---|
| Cornstarch | to 100 | to 100 | to 100 | to 100 | — |
| Corn | 50.89 | 60.85 | 78.42 | 83.85 | 63.65 |
| Soybean meal, dehulled | 39.69 | 31.19 | 18.08 | 12.65 | 25.65 |
| Soybean oil | 5.00 | 3.00 | — | — | — |
| Limestone, ground | 1.67 | 1.06 | 1.06 | 1.07 | 9.80 |
| Salt | 0.40 | — | — | — | 0.40 |
| Dicalcium phosphate | — | — | 0.16 | — | — |
| Trace mineral premix | 0.15[a] | 0.35[b] | 0.35[b] | 0.35[b] | 0.20[a] |
| Vitamin premix | 0.20[c] | 0.20[d] | 0.10[d] | 0.10[d] | 0.15[c] |
| Choline Chloride (60%) | 0.20 | — | — | — | 0.05 |
| Antibiotic premix | 0.05[e] | 1.00[f] | 0.75[g] | 0.75[g] | — |
| Copper sulfate | — | 0.08 | — | — | — |
| L-Lysine HCl, feed grade | — | 0.17 | 0.16 | 0.11 | — |
| L-Threonine, feed grade | — | — | 0.02 | — | — |
| DL-Methionine, feed grade | 0.20 | 0.05 | — | — | 0.10 |
| Chemical composition | | | | | |
| Crude protein, %[h] | 22.6 | 20.8 | 15.1 | 13.0 | 17.0 |
| Total phosphorus, %[h] | 0.42 | 0.35 | 0.38 | 0.32 | 0.34 |
| Available phosphorus, %[i] | 0.10 | 0.075 | 0.09 | 0.05 | 0.07 |
| Calcium, %[i] | 0.75 | 0.60 | 0.50 | 0.45 | 3.8 |
| ME, kcal/kg[i] | 3123 | 3387 | 3293 | 3295 | 2758 |

[a]Supplied the following per kilogram of complete diet: Fe, 75 mg (FeSO$_4$H$_2$O); Zn, 100 mg (ZnO); Mn, 75 mg (MnO); Cu, 8 mg (CuSO$_4$H$_2$O); I, 0.35 mg (CaI$_2$); Se, 0.3 mg (Na$_2$SeO$_3$); NaCL, 3 g.
[b]Supplied the following per kilogram of complete diet: Fe, 90 mg (FeSO$_4$H$_2$O); Zn, 100 mg (ZnO); Mn, 20 mg (MnO); Cu, 8 mg (CuSO$_4$H$_2$O); I, 0.35 mg (CaI$_2$); Se,.0.3 mg (Na$_2$SeO$_3$); NaCl, 3 g.
[c]Supplied the following per kilogram of complete diet: retinyl acetate, 1,514 µg; cholecalciferol, 25 µg; DL-α-tocopheryl acetate, 11 mg; menadione sodium bisulfite complex, 2.3 mg; niacin, 22 mg; D-Ca-pantothenate, 10 mg; riboflavin, 4.4 mg; vitamin B$_{12}$, 11 µg.
[d]Supplied the following per kilogram of complete diet; retinyl acetate, 2,273 µg; cholecalciferol, 16.5 µg; DL-α-tocopheryl acetate, 88 mg; menadione, 4.4 mg (menadione sodium bisulfite complex); niacin, 33 mg; D-Ca-pantothenate, 24.2 mg; riboflavin, 8.8 mg; vitamin B$_{12}$, 35 µg; choline chloride, 319 mg.
[e]Provided 50 mg of bacitracin per kilogram of complete diet.
[f]Provided 55 mg of mecadox per kilogram of complete diet.
[g]Provided 38 mg of roxarsone per kilogram of complete diet.
[h]Analyzed (AOAC, 1999).
[i]Calculated (NRC, 1994; NRC, 1998).

Assessment of relative phosphorus bioavailability in chicks as affected by two different phytase enzymes (Chick assay 1)[a].

| Diet | Weight gain, g | Gain/feed, g/kg | Tibia ash % | Tibia ash mg | Bioavailable P, % |
|---|---|---|---|---|---|
| 5. As 1 + 500 FTU/kg ECP | 346[e] | 656[e] | 37.8[e] | 448[e] | 0.124[e] |
| Pooled SEM | 6 | 10 | 0.5 | 10 | 0.006 |

[a]Values are means of five pens of four male chicks fed the experimental diets during the period 8 to 22 d post-hatching; average initial weight was 91 g.

[b]The linear regression of tibia ash (mg) for Diets 1 to 3 as a function of supplemental P intake (g) was $Y = 257.1 \pm 9.8 + 299.0 \pm 30.7X$ ($r^2 = 0.88$); Bioavailable P concentrations (equivalent P yields) for Diets 4 and 5 were determined by calculating equivalent bioavailable P intake (g) from the standard curve, dividing that by the feed intake (g), and multiplying by 100.

[c,d,e,f]Means within a column with different superscripts are different, $P < 0.05$.

Relative phosphorus bioavailability in chicks fed different phytase enzymes (Chick assay 2)[a].

| Diet | Weight gain, g | Gain/feed, g/kg | Tibia ash % | Tibia ash mg | Bioavailable P, % |
|---|---|---|---|---|---|
| 1. Basal diet | 176[k] | 569[k] | 24.9[k] | 183[k] | — |
| 2. As 1 + 0.05% $P_i$(KH$_2$PO$_4$) | 253[hi] | 680[h] | 30.0[h] | 272[h] | — |
| 3. As 1 + 0.10% $P_i$(KH$_2$PO$_4$) | 293[g] | 703[fgh] | 34.3[g] | 347[g] | — |
| 4. As 1 + 0.15% $P_i$(KH$_2$PO$_4$) | 333[f] | 731[ef] | 37.3[e] | 455[e] | — |
| 5. As 1 + 500 FTU/kg Natuphos ®[c] | 218[j] | 620[j] | 27.2[j] | 224[j] | 0.026[g] |
| 6. As 1 + 500 FTU/kg Natuphos ®[d] | 236[ij] | 632[j] | 27.5[ij] | 236[ij] | 0.032[fg] |
| 7. As 1 + 1,000 FTU/kg Natuphos ®[d] | 265[i] | 675[gh] | 28.9[hi] | 262[hi] | 0.048[f] |
| 8. As 1 + 500 FTU/kg Ronozyme ® | 219[j] | 634[j] | 26.9[j] | 223[j] | 0.028[g] |
| 9. As 1 + 1,000 FTU/kg Ronozyme ® | 245[i] | 682[gh] | 27.5[ij] | 242[hij] | 0.038[fg] |
| 10. As 1 + 500 FTU/kg ECP | 318[ef] | 708[fgh] | 36.5[ef] | 409[f] | 0.125[e] |
| Pooled SEM | 7 | 10 | 0.6 | 12 | 0.006 |

[a]Values are means of five pens of four male chicks fed the experimental diets during the period 8 to 22 d posthatching; average initial weight was 83 g.

[b]The linear regression of tibia ash (mg) for Diets 1 to 4 as a function of supplemental P intake (g) was $Y = 187.9 \pm 8.7 + 393.4 \pm 21.2X$ ($r^2 = 0.95$); Bioavailable P concentrations (equivalent P yields) for Diets 4–11 were determined by calculating equivalent bioavailable P intake (g) from the standard curve, dividing that by the feed intake (g), and multiplying by 100.

[c]Enzyme was from the same batch that was used for chick assay 1.

[d]Enzyme was from a different batch that was used for chick assay 1.

[e,f,g,h,i,j,k]Means within a column with different superscripts are different, $P < 0.05$.

The effect of activity level on the phosphorus-releasing efficacy of E. coli phytase in chicks (Chick assay 3)[a].

| Diet | Weight gain, g | Gain/feed, g/kg | Tibia ash mg | Bioavailable P, %[b] |
|---|---|---|---|---|
| 1. Basal diet | 219[h] | 661[e] | 237[i] | — |
| 2. As 1 + 0.05% $P_i$(KH$_2$PO$_4$) | 283[fg] | 692[d] | 299[h] | — |
| 3. As 1 + 0.10% $P_i$(KH$_2$PO$_4$) | 314[c] | 720[c] | 413[g] | — |
| 4. As 1 + 0.15% $P_i$(KH$_2$PO$_4$) | 327[dc] | 731[c] | 490[e] | — |
| 5. As 1 + 500 FTU/kg ECP | 321[dc] | 731[c] | 447[f] | 0.125[c] |
| 6. As 1 + 1,000 FTU/kg ECP | 335[cd] | 732[c] | 559[d] | 0.183[d] |
| 7. As 1 + 1,500 FTU/kg ECP | 344[c] | 737[c] | 616[c] | 0.211[c] |
| 8. As 1 + 500 FTU/kg Natuphos ® | 276[g] | 691[d] | 290[h] | 0.037[f] |
| Pooled SEM | 6 | 10 | 12 | 0.005 |

[a]Values are means of five pens of four male chicks fed the experimental diets during the period 8 to 22 d post-hatching; average initial weight was 97 g.

[b]The linear regression of tibia ash (mg) for Diets 1 to 4 as a function of supplemental P intake (g) was $Y = 232.0 \pm 6.9 + 389.9 \pm 16.7X$ ($r^2 = 0.97$); Bioavailable P concentrations (equivalent P yields) for Diets 5 to 8 were determined by calculating equivalent bioavailable P intake (g) from the standard curve, dividing that by the feed intake (g) of the pen, and multiplying by 100.

[c,d,e,f,g,h,i]Means within a column with different superscripts are different, $P < 0.05$.

Combining 3- and 6-phytases does not produce synergistic effects on Pi-release in chicks fed a corn-soybean meal diet(Chick assay 4)[a].

| Diet | Weight gain, g | Gain/feed, g/kg | Tibia ash % | Tibia ash mg | Bioavailable P, %[b] |
|---|---|---|---|---|---|
| 1. Basal diet | 137[g] | 610[g] | 25.4[g] | 134[h] | — |
| 2. As 1 + 0.05% $P_i$(KH$_2$PO$_4$) | 191[ef] | 678[dc] | 29.0[f] | 198[fg] | — |
| 3. As 1 + 0.10% $P_i$(KH$_2$PO$_4$) | 225[d] | 712[d] | 32.8[e] | 253[e] | — |
| 4. As 1 + 0.15% $P_i$(KH$_2$PO$_4$) | 276[c] | 762[c] | 36.3[d] | 339[d] | — |
| 5. As 1 + 500 FTU/kg Natuphos ® | 192[ef] | 624[fg] | 28.0[f] | 187[g] | 0.041[g] |
| 6. As 1 + 500 FTU/kg Ronozyme ® | 182[f] | 655[cf] | 27.7[f] | 188[g] | 0.047[fg] |
| 7. As 1 + 500 FTU/kg ECP | 272[c] | 760[c] | 37.0[d] | 343[d] | 0.153[d] |
| 8. As 5 + 6 | 211[de] | 693[de] | 28.3[f] | 212[fg] | 0.064[ef] |
| 9. As 5 + 7 | 282[c] | 763[c] | 37.8[d] | 360d | 0.162[d] |
| 10. As 1 + 1,000 FTU/kg Natuphos ® | 217[d] | 703[d] | 29.0[f] | 217[f] | 0.067[c] |
| 11. As 1 + 1,000 FTU/kg Ronozyme ® | 201[def] | 666[ef] | 27.9[f] | 194[fg] | 0.050[efg] |
| 12. As 1 + 1,000 FTU/kg ECP | 292[c] | 758[c] | 41.1[c] | 433[c] | 0.206[c] |
| Pooled SEM | 9 | 15 | 0.6 | 10 | 0.007 |

[a]Values are means of five pens of four male chicks fed the experimental diets during the period 8 to 22 d post-hatching; average initial weight was 68 g.

[b]The linear regression of tibia ash (mg) for Diets 1 to 4 as a function of supplemental P intake (g) was $Y = 138.6 \pm 4.9 + 371.3 \pm 14.7X$ ($r^2 = 0.97$); Bioavailable P concentrations (equivalent P yields) for Diets 5 to 8 were determined by calculating equivalent bioavailable P intake (g) from the standard curve, dividing that by the feed intake (g) of the pen, and multiplying by 100.

[c,d,e,f,g]Means within a column with different superscripts are different, $P < 0.05$.

Effect of *E. coli* phytase on performance of laying hens from week 1–4.[a]

| Diet | Initial hen weight, g | 4-wk hen weight, g | Feed intake, g/d | Egg production, %[b] | Egg weight, g |
|---|---|---|---|---|---|
| 1. P-deficient basal diet | 1716 | 1593 | 90 | 54.0 | 61.0 |
| 2. As 1 + 0.10% Pi | 1725 | 1748 | 122 | 84.8 | 64.2 |
| 3. As 1 + 150 FTU/kg ECP | 1733 | 1771 | 119 | 83.7 | 63.8 |
| 4. As 1 + 300 FTU/kg ECP | 1798 | 1806 | 119 | 82.3 | 65.4 |
| 5. As 1 + 10,000 FTU/kg ECP | 1746 | 1770 | 123 | 85.9 | 65.1 |
| Pooled SEM | 26 | 21[c] | 2[c] | 1.6[c] | 0.7[c] |

[a]Data are means of four replicates of 12 hens for the first 4 weeks of the study period.
[b]Egg production (%) analyzed using covariance; data presented are least-squares means.
[c]Diet 1 vs diets 2–5, P < 0.01.

Effect of *E. coli* phytase on performance of laying hens from week 5–12.[a]

| Diet | 4-wk hen weight, g | Feed intake, g/d | Egg production, %[b] | Egg weight, g |
|---|---|---|---|---|
| 2. As 1 + 0.10% Pi | 1830 | 120 | 80.5 | 64.0 |
| 3. As 1 + 150 FTU/kg ECP | 1796 | 118 | 80.6 | 64.1 |
| 4. As 1 + 300 FTU/kg ECP | 1833 | 116 | 77.2 | 65.5 |
| 5. As 1 + 10,000 FTU/kg ECP | 1830 | 120 | 81.2 | 64.8 |
| Pooled SEM | 24 | 2 | 2.5 | 0.5[c] |

[a]Data are means of four replicates of 12 hens for weeks 5 through 12 of the study period. Diet 1 was removed from study due to poor egg production.
[b]Egg production (%) analyzed using covariance; data presented are least-squares means.
[c]Diet 3 vs diets 4 and 5, P < 0.01.

Effect of *E. coli* phytase on performance of laying hens from week 1–12.[a]

| Diet | Hen weights Initial | Hen weights 4-wk | Hen weights 12-wk | Feed intake, g/d | Egg production, %[b] | Egg weight, g |
|---|---|---|---|---|---|---|
| 1. P-deficient basal diet | 1716 | 1593 | — | 90 | 53.8 | 61.0 |
| 2. As 1 + 0.10% PI | 1725 | 1748 | 1830 | 121 | 81.2 | 64.1 |
| 3. As 1 + 150 FTU/kg ECP | 1733 | 1771 | 1796 | 118 | 80.7 | 64.1 |
| 4. As 1 + 300 FTU/kg ECP | 1798 | 1806 | 1833 | 117 | 77.8 | 65.5 |
| 5. As 1 + 10,000 FTU/kg ECP | 1746 | 1770 | 1830 | 121 | 82.9 | 64.8 |
| Pooled SEM | 26 | 21[c] | 24 | 2[c] | 2.1[c] | 0.7[c] |

[a]Data are means of four replicates of 12 hens. Data are means for the first 4 weeks for diet 1, but for all 12 weeks for diets 2–5.
[b]Egg production (%) analyzed using covariance; data presented are least-squares means.
[c]Diet 1 vs diets 2–5, P < 0.01.

Relative bioavailability of phosphorus in young pigs fed different phrase enzymes (Pig assay 1).

| Diet | Weight gain, g/d[a] | Gain/feed, g/kg[a] | Fibula ash % | Fibula ash mg | Bioavailable P, %[c] |
|---|---|---|---|---|---|
| 1. Basal diet | 369[f] | 533[f] | 29.3[g] | 666[i] | — |
| 2. As 1 + 0.05% $P_i$ ($KH_2PO_4$) | 435[e] | 576[ef] | 32.8[f] | 766[hi] | — |
| 3. As 1 + 0.10% $P_i$ ($KH_2PO_4$) | 476[de] | 618[de] | 36.6[d] | 972[ef] | — |
| 4. As 1 + 0.15% $P_i$ ($KH_2PO_4$) | 509[d] | 660[d] | 36.6[d] | 1123[d] | — |
| 5. As 1 + 400 FTU/kg Natuphos ® | 460[c] | 605[de] | 34.4[def] | 889[fg] | 0.081[de] |
| 6. As 1 + 400 FTU/kg Ronozyme ® | 445[e] | 565[ef] | 33.5[ef] | 805[gh] | 0.043[f] |
| 7. As 1 + 400 FTU/kg ECP | 443[e] | 583[ef] | 35.0[def] | 968[ef] | 0.108[d] |
| Pooled SEM | 17 | 21 | 0.8 | 38 | 0.016 |

[a]Data are means of 10 individually-fed pigs over a 23-d feeding period; average initial weight was 8.4 kg.
[b]Data are means of five individually-fed pigs, chosen from the median-weight blocks at the end of the 23-d feeding period.
[c]The linear regression of fibula ash (mg) for Diets 1 to 4 as a function of supplemental P intake (g) was Y = 664.5 ± 25.5 + 15.3 ± 1.4X ($r^2$ = 0.87); Bioavailable P concentrations (equivalent P yields) for Diets 5–7 were determined by calculating equivalent bioavailable P intake (g) from the standard curve, dividing that by the feed intake (g) of the pig, and multiplying by 100.
[d,e,f,g,h,i]Means within a column with different superscripts are different, P < 0.05.

Effect of *E. coil* phytase on growth performance of finishing pigs (Pig assay 2)[a].

| Response variable | P-deficient basal diet | As 1 + 0.10% Pi | As 1 + 250 FTU/kg ECP | As 1 + 500 FTU/kg ECP | As 1 + 1,000 FTU/kg ECP | As 1 + 10,000 FTU/kg ECP | Pooled SEM |
|---|---|---|---|---|---|---|---|
| Daily gain, g[b] | | | | | | | |
| Barrows | 935 | 1023 | 1023 | 929 | 993 | 974 | |
| Gilts | 752 | 790 | 872 | 909 | 828 | 902 | |
| Mean | 844 | 907 | 947 | 919 | 910 | 938 | 38 |
| Daily feed, g[c] | | | | | | | |
| Barrows | 2837 | 2861 | 3028 | 2712 | 2873 | 2684 | |
| Gilts | 2347 | 2197 | 2571 | 2507 | 2378 | 2562 | |
| Mean | 2592 | 2529 | 2800 | 2610 | 2625 | 2623 | 81 |
| Gain/feed, g/kg[d] | | | | | | | |
| Barrows | 331 | 358 | 338 | 343 | 346 | 365 | |
| Gilts | 320 | 363 | 341 | 363 | 349 | 352 | |
| Mean | 325 | 361 | 339 | 353 | 347 | 359 | 9 |

[a] Data are means of five individually-fed pigs of each sex fed their experimental diets from 48.9 to 117.6 kg body weight.
[b] Sex x diet interaction. $P < 0.10$; Sex x Pi vs phytase-supplemented dies, $P < 0.05$.
[c] Barrows vs gilts, $P < 0.01$.
[d] P-deficient vs Pi- and phytase-supplemented diets, $P < 0.01$.

Effect of *E. coil* phytase on bone characteristics of finishing pigs (Pig assay 2)[a].

| Response variable | P-deficient basal diet | As 1 + 0.10% Pi | As 1 + 250 FTU/kg ECP | As 1 + 500 FTU/kg ECP | As 1 + 1,000 FTU/kg ECP | As 1 + 10,000 FTU/kg ECP | Pooled SEM |
|---|---|---|---|---|---|---|---|
| Fibula ash, % g[b] | | | | | | | |
| Barrows | 52.9 | 58.8 | 57.8 | 58.9 | 58.5 | 58.5 | |
| Gilts | 52.4 | 59.2 | 58.9 | 55.8 | 58.3 | 58.8 | |
| Mean | 52.6 | 59.0 | 58.3 | 57.3 | 58.4 | 58.7 | 0.7 |
| Fibula ash, g[bcdef] | | | | | | | |
| Barrows | 4.57 | 6.30 | 5.69 | 6.56 | 6.37 | 7.04 | |
| Gilts | 4.19 | 6.06 | 5.90 | 5.99 | 6.24 | 6.86 | |
| Mean | 4.38 | 6.18 | 5.80 | 6.28 | 6.31 | 6.95 | 0.17 |
| Metatarsal ash, %[b] | | | | | | | |
| Barrows | 40.3 | 46.9 | 48.8 | 47.5 | 47.3 | 47.6 | |
| Gilts | 43.1 | 48.5 | 48.3 | 45.4 | 49.0 | 49.0 | |
| Mean | 41.7 | 47.7 | 48.5 | 46.5 | 48.1 | 48.3 | 1.1 |
| Metatarsal ash, g[bd] | | | | | | | |
| Barrows | 5.4 | 6.6 | 6.8 | 7.0 | 7.2 | 7.4 | |
| Gilts | 4.9 | 6.6 | 6.5 | 7.0 | 6.8 | 7.3 | |
| Mean | 5.1 | 6.6 | 6.6 | 7.0 | 7.0 | 7.3 | 0.2 |

[a] Data are means of five individually-fed pigs of each sex fed their experimental diets from 48.9 to 117.6 kg body weight.
[b] P-deficient vs Pi- and phytase-supplemented diets, $P < 0.01$.
[c] Barrows vs gilts, $P < 0.10$.
[d] 250 U/kg vs higher phytase activity levels, $P < 0.01$.
[e] 500 U/kg vs 1,000 and 10,000 U/kg phytase, $P < 0.10$.
[f] 1,000 U/kg vs 10,000 U/kg phytase, $P < 0.01$.

What is claimed is:

1. A method of improving the nutritional value of a foodstuff consumed by a monogastric animal by increasing the bioavailability of phosphate from phytate wherein the foodstuff comprises myo-inositol hexakisphosphate, the method comprising the step of feeding to the animal the foodstuff in combination with less than 1200 units of an *E. coli* 6-phytase expressed in yeast per kilogram of the foodstuff,
wherein the bioavailability of phosphate from phytate is increased by at least 2-fold compared to the bioavailability of phosphate from phytate obtained by feeding the foodstuff in combination with the same units of a phytase expressed in a non-yeast host cell.

2. The method of claim 1 wherein the animal is an avian species.

3. The method of claim 2 wherein the avian species is selected from the group consisting of a chicken, a turkey, a duck, and a pheasant.

4. The method of claim 1 wherein the animal a porcine species.

5. The method of claim 1 wherein the animal is a marine or a fresh water aquatic species.

6. The method of claim 1 wherein the animal is a domestic animal.

7. The method of claim 6 wherein the domestic animal is a canine species.

8. The method of claim 6 wherein the domestic animal is a feline species.

9. The method of claim 1 wherein the animal is a human.

10. The method of claim 4 wherein the foodstuff is pig feed.

11. The method of claim 3 wherein the foodstuff is poultry feed.

12. The method of claim 1 wherein the yeast is selected from the group consisting of *Saccharomyces* species, *Pichia* species, *Kluyveromyces* species, *Hansenula* species, and *Candida species*.

13. The method of claim 12 wherein the yeast is *Saccharomyces cerevisiae*.

14. The method of claim 12 wherein the yeast is *Pichia pastoris*.

15. The method of claim 1 wherein the animal is fed the foodstuff in combination with from about 50 to about 1000 units of the 6-phytase expressed in yeast per kilogram of the foodstuff.

16. The method of claim 1 wherein the animal is fed the foodstuff in combination with from about 50 to about 700 units of the 6-phytase expressed in yeast per kilogram of the foodstuff.

17. The method of claim 1 wherein the animal is fed the foodstuff in combination with from about 50 to about 500 units of the 6-phytase expressed in yeast per kilogram of the foodstuff.

18. The method of claim 1 wherein the animal is fed the foodstuff in combination with from about 50 to about 200 units of the 6-phytase expressed in yeast per kilogram of the foodstuff.

19. The method of claim 1 wherein the 6-phytase has an optimal activity at a pH of less than about 4.

20. The method of claim 1 wherein the 6-phytase expressed in yeast is cleaved with a protease to enhance the capacity of the 6-phytase to increase the bioavailability of phosphate from phytate compared to intact yeast-expressed 6-phytase.

21. A method of improving the nutritional value of a foodstuff consumed by a monogastric animal wherein the foodstuff comprises myo-inositol hexakisphosphate, the method comprising the steps of:
spray drying an *E. coli* 6-phytase;
mixing the phytase with a carrier for the phytase and, optionally, other ingredients to produce a feed additive composition for supplementing the foodstuff with the phytase;
mixing the feed additive composition with the foodstuff; and
feeding the animal the foodstuff supplemented with the feed additive composition.

22. A method of improving the nutritional value of a foodstuff consumed by an avian species by increasing the bioavailability of phosphate from phytate wherein the foodstuff comprises myo-inositol hexaikisphosphate, the method comprising the step of feeding to the avian species the foodstuff in combination with less than 1200 units of an *E. coli* 6-phvtase expressed in yeast per kilogram of the foodstuff, wherein the bioavailability of phosphate from phytate is increased by at least 1.5-fold compared to the bioavailability of phosphate from phytate obtained by feeding to a non-avian species the foodstuff in combination with the phytase expressed in yeast.

23. The method of claim 22 wherein the avian species is selected from the group consisting of a chicken, a turkey, a duck, and a pheasant.

24. The method of claim 22 wherein the foodstuff is poultry feed.

25. The method of claim 22 wherein the yeast is selected from the group consisting of *Saccharomyces* species, *Pichia* species, *Kluyveromyces* species, *Hansenula* species, and *Candida species*.

26. The method of claim 22 wherein the animal is fed the foodstuff in combination with 2000 units or less of the phytase expressed in yeast per kilogram of the foodstuff.

27. The method of claim 22 wherein the animal is fed the foodstuff in combination with 1500 units or less of the phytase expressed in yeast per kilogram of the foodstuff.

28. The method of claim 22 wherein the phytase has an optimal activity at a pH of less than about 4.

29. The method of claim 22 wherein the animal is fed the foodstuff in combination with from about 50 to about 1000 units of the phytase expressed in yeast per kilogram of the foodstuff.

30. The method of claim 22 wherein the animal is fed the foodstuff in combination with from about 50 to about 700 units of the phytase expressed in yeast per kilogram of the foodstuff.

31. The method of claim 22 wherein the animal is fed the foodstuff in combination with from about 50 to about 500 units of the phytase expressed in yeast per kilogram of the foodstuff.

32. The method of claim 22 wherein the animal is fed the foodstuff in combination with from about 50 to about 200 units of the phytase expressed in yeast per kilogram of the foodstuff.

33. The method of claim 22 wherein the phytase expressed in yeast is cleaved with a protease to enhance the capacity of the phytase to increase the bioavailability of phosphate from phytate compared to intact yeast-expressed phytase.

34. The method of claim 22 wherein the bioavailability of phosphate from phytate obtained by feeding the foodstuff in combination with the phytase expressed in yeast is increased by at least 2-fold compared to the bioavailability of phosphate from phytate obtained by feeding the foodstuff in combination with the same units of a phytase expressed in a non-yeast host cell.

35. The method of claim 21 wherein the foodstuff is supplemented with less than 1200 units of the phytase per kilogram of the foodstuff and wherein the bioavailability to the animal of phosphate from phytate is increased by at least 2-fold compared to the bioavailability of phosphate from phytate obtained by feeding the foodstuff in combination with the same units of a phytase expressed in a non-yeast host cell.

* * * * *

UNITED STATES PATENT AND TRADEMARK OFFICE
CERTIFICATE OF CORRECTION

PATENT NO. : 7,320,876 B2  
APPLICATION NO. : 10/284962  
DATED : January 22, 2008  
INVENTOR(S) : Douglas M. Webel et al.

Page 1 of 1

It is certified that error appears in the above-identified patent and that said Letters Patent is hereby corrected as shown below:

Column 73, line 37, please insert -- is -- after the word "animal" and before the word "a."

Column 74, line 50, please delete "hexaikisphosphate" and insert -- hexakisphosphate -- therefor.

Column 74, line 53, please delete "6-phvtase" and insert -- 6-phytase -- therefor.

Signed and Sealed this

Thirteenth Day of May, 2008

JON W. DUDAS  
*Director of the United States Patent and Trademark Office*

SEQUENCE LISTING

<160> NUMBER OF SEQ ID NOS: 14

<210> SEQ ID NO 1
<211> LENGTH: 1489
<212> TYPE: DNA

```
<213> ORGANISM: Escherichia coli
<220> FEATURE:
<221> NAME/KEY: primer_bind
<222> LOCATION: (1)..(22)
<223> OTHER INFORMATION:
<220> FEATURE:
<221> NAME/KEY: primer_bind
<222> LOCATION: (1468)..(1489)
<223> OTHER INFORMATION:
<220> FEATURE:
<221> NAME/KEY: CDS
<222> LOCATION: (16)..(108)
<223> OTHER INFORMATION:
<220> FEATURE:
<221> NAME/KEY: CDS
<222> LOCATION: (182)..(1480)
<223> OTHER INFORMATION:

<400> SEQUENCE: 1
```

| | | | | | | | | | | | |
|---|---|---|---|---|---|---|---|---|---|---|---|
| taaggagcag | aaaca | atg | tgg | tat | ttc | ctt | tgg | ttc | gtc | ggc | att ttg ttg | 51 |
| | | Met | Trp | Tyr | Phe | Leu | Trp | Phe | Val | Gly | Ile Leu Leu |
| | | 1 | | 5 | | | | | | 10 | |

```
atg tgt tcg ctc tcc acc ctt gtg ttg gta tgg ctg gac ccg cga ttg        99
Met Cys Ser Leu Ser Thr Leu Val Leu Val Trp Leu Asp Pro Arg Leu
    15                  20                  25 aaa agt taa cgaacgtaag cctgatccgg cgcattagcg tcgatcaggc                148
Lys Ser
    30 aataatatcg atatcaaag cggaaacata tcg atg aaa gcg atc tta atc cca        202
                                   Met Lys Ala Ile Leu Ile Pro
                                     1               35 ttt tta tct ctt ttg att ccg tta acc ccg caa tct gca ttc gct cag        250
Phe Leu Ser Leu Leu Ile Pro Leu Thr Pro Gln Ser Ala Phe Ala Gln
        40                  45                  50 agt gag ccg gag ctg aag ctg gaa agt gtg gtg att gtc agc cgt cat        298
Ser Glu Pro Glu Leu Lys Leu Glu Ser Val Val Ile Val Ser Arg His
    55                  60                  65 ggt gtg cgt gcc cca acc aag gcc acg caa ctg atg cag gat gtc acc        346
Gly Val Arg Ala Pro Thr Lys Ala Thr Gln Leu Met Gln Asp Val Thr
70                  75                  80                  85 cca gac gca tgg cca acc tgg ccg gta aaa ctg ggt tgg ctg aca cca        394
Pro Asp Ala Trp Pro Thr Trp Pro Val Lys Leu Gly Trp Leu Thr Pro
                90                  95                 100 cgc ggt ggt gag cta atc gcc tat ctc gga cat tac caa cgc cag cgt        442
Arg Gly Gly Glu Leu Ile Ala Tyr Leu Gly His Tyr Gln Arg Gln Arg
            105                 110                 115 ctg gtg gcc gac gga ttg ctg gcg aaa aag ggc tgc ccg cag cct ggt        490
Leu Val Ala Asp Gly Leu Leu Ala Lys Lys Gly Cys Pro Gln Pro Gly
        120                 125                 130 cag gtc gcg att att gct gat gtc gac gag cgt acc cgt aaa aca ggc        538
Gln Val Ala Ile Ile Ala Asp Val Asp Glu Arg Thr Arg Lys Thr Gly
    135                 140                 145 gaa gcc ttc gcc gcc ggg ctg gca cct gac tgt gca ata acc gta cat        586
Glu Ala Phe Ala Ala Gly Leu Ala Pro Asp Cys Ala Ile Thr Val His
150                 155                 160                 165 acc cag gca gat acg tcc agt ccc gat ccg tta ttt aat cct cta aaa        634
Thr Gln Ala Asp Thr Ser Ser Pro Asp Pro Leu Phe Asn Pro Leu Lys
                170                 175                 180 act ggc gtt tgc caa ctg gat aac gcg aac gtg act gac gcg atc ctc        682
Thr Gly Val Cys Gln Leu Asp Asn Ala Asn Val Thr Asp Ala Ile Leu
            185                 190                 195 agc agg gca gga ggg tca att gct gac ttt acc ggg cat cgg caa acg        730
Ser Arg Ala Gly Gly Ser Ile Ala Asp Phe Thr Gly His Arg Gln Thr
        200                 205                 210
```

```
gcg ttt cgc gaa ctg gaa cgg gtg ctt aat ttt tcc caa tta aac ttg      778
Ala Phe Arg Glu Leu Glu Arg Val Leu Asn Phe Ser Gln Leu Asn Leu
    215                 220                 225 tgc ctt aac cgt gag aaa cag gac gaa agc tgt tca tta acg cag gca      826
Cys Leu Asn Arg Glu Lys Gln Asp Glu Ser Cys Ser Leu Thr Gln Ala
230                 235                 240                 245 tta cca tcg gaa ctc aag gtg agc gcc gac aat gtt tca tta acc ggt      874
Leu Pro Ser Glu Leu Lys Val Ser Ala Asp Asn Val Ser Leu Thr Gly
                250                 255                 260 gcg gta agc ctc gca tca atg ctg acg gaa ata ttt ctc ctg caa caa      922
Ala Val Ser Leu Ala Ser Met Leu Thr Glu Ile Phe Leu Leu Gln Gln
    265                 270                 275 gca cag gga atg ccg gag ccg ggg tgg gga agg atc act gat tca cac      970
Ala Gln Gly Met Pro Glu Pro Gly Trp Gly Arg Ile Thr Asp Ser His
280                 285                 290 cag tgg aac acc ttg cta agt ttg cat aac gcg caa ttt tat tta cta     1018
Gln Trp Asn Thr Leu Leu Ser Leu His Asn Ala Gln Phe Tyr Leu Leu
                295                 300                 305 caa cgc acg cca gag gtt gcc cgc agt cgc gcc acc ccg tta ttg gat     1066
Gln Arg Thr Pro Glu Val Ala Arg Ser Arg Ala Thr Pro Leu Leu Asp
310                 315                 320                 325 ttg atc atg gca gcg ttg acg ccc cat cca ccg caa aaa cag gcg tat     1114
Leu Ile Met Ala Ala Leu Thr Pro His Pro Pro Gln Lys Gln Ala Tyr
                330                 335                 340 ggt gtg aca tta ccc act tca gtg ctg ttt att gcc gga cac gat act     1162
Gly Val Thr Leu Pro Thr Ser Val Leu Phe Ile Ala Gly His Asp Thr
    345                 350                 355 aat ctg gca aat ctc ggc ggc gca ctg gag ctc aac tgg acg ctt cca     1210
Asn Leu Ala Asn Leu Gly Gly Ala Leu Glu Leu Asn Trp Thr Leu Pro
360                 365                 370 ggt cag ccg gat aac acg ccg cca ggt ggt gaa ctg gtg ttt gaa cgc     1258
Gly Gln Pro Asp Asn Thr Pro Pro Gly Gly Glu Leu Val Phe Glu Arg
                375                 380                 385 tgg cgt cgg cta agc gat aac agc cag tgg att cag gtt tcg ctg gtc     1306
Trp Arg Arg Leu Ser Asp Asn Ser Gln Trp Ile Gln Val Ser Leu Val
390                 395                 400                 405 ttc cag act tta cag cag atg cgt gat aaa acg ccg cta tca tta aat     1354
Phe Gln Thr Leu Gln Gln Met Arg Asp Lys Thr Pro Leu Ser Leu Asn
                410                 415                 420 acg ccg ccc gga gag gtg aaa ctg acc ctg gca gga tgt gaa gag cga     1402
Thr Pro Pro Gly Glu Val Lys Leu Thr Leu Ala Gly Cys Glu Glu Arg
    425                 430                 435 aat gcg cag ggc atg tgt tcg ttg gcc ggt ttt acg caa atc gtg aat     1450
Asn Ala Gln Gly Met Cys Ser Leu Ala Gly Phe Thr Gln Ile Val Asn
440                 445                 450 gaa gcg cgc ata ccg gcg tgc agt ttg taa tggtacccc                   1489
Glu Ala Arg Ile Pro Ala Cys Ser Leu
    455                 460

<210> SEQ ID NO 2
<211> LENGTH: 30
<212> TYPE: PRT
<213> ORGANISM: Escherichia coli

<400> SEQUENCE: 2

Met Trp Tyr Phe Leu Trp Phe Val Gly Ile Leu Leu Met Cys Ser Leu
1               5                   10                  15

Ser Thr Leu Val Leu Val Trp Leu Asp Pro Arg Leu Lys Ser
            20                  25                  30

<210> SEQ ID NO 3
```

<211> LENGTH: 432
<212> TYPE: PRT
<213> ORGANISM: Escherichia coli

<400> SEQUENCE: 3

```
Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
        35                  40                  45

Gln Leu Met Gln Asp Val Thr Pro Asp Ala Trp Pro Thr Trp Pro Val
    50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Pro Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
    130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
            180                 185                 190

Asn Phe Ser Gln Leu Asn Leu Cys Leu Asn Arg Glu Lys Gln Asp Glu
        195                 200                 205

Ser Cys Ser Leu Thr Gln Ala Leu Pro Ser Glu Leu Lys Val Ser Ala
    210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
        275                 280                 285

Arg Ala Thr Pro Leu Leu Asp Leu Ile Met Ala Ala Leu Thr Pro His
    290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Arg Leu Ser Asp Asn Ser Gln
        355                 360                 365

Trp Ile Gln Val Ser Leu Val Phe Gln Thr Leu Gln Gln Met Arg Asp
    370                 375                 380

Lys Thr Pro Leu Ser Leu Asn Pro Pro Gly Glu Val Lys Leu Thr
385                 390                 395                 400
```

```
Leu Ala Gly Cys Glu Glu Arg Asn Ala Gln Gly Met Cys Ser Leu Ala
                405                 410                 415
Gly Phe Thr Gln Ile Val Asn Glu Ala Arg Ile Pro Ala Cys Ser Leu
            420                 425                 430

<210> SEQ ID NO 4
<211> LENGTH: 1486
<212> TYPE: DNA
<213> ORGANISM: Escherichia coli
<220> FEATURE:
<221> NAME/KEY: CDS
<222> LOCATION: (188)..(1483)
<223> OTHER INFORMATION:

<400> SEQUENCE: 4
taaggagcag aaacaatgtg gtatttactt tggttcgtcg gcattttgtt gatgtgttcg     60
ctctccaccc ttgtgttggt atggctggac ccgcgattga aaagttaacg aacgtaggcc    120
tgatgcggcg cattagcatc gcatcaggca atcaataatg tcagatatga aaagcggaaa    180 catatcg atg aaa gcg atc tta atc cca ttt tta tct ctt ctg att ccg     229
        Met Lys Ala Ile Leu Ile Pro Phe Leu Ser Leu Leu Ile Pro
          1               5                  10 tta acc ccg caa tct gca ttc gct cag agt gag ccg gag ctg aag ctg     277
Leu Thr Pro Gln Ser Ala Phe Ala Gln Ser Glu Pro Glu Leu Lys Leu
 15              20                  25                  30 gaa agt gtg gtg att gtc agc cgt cat ggt gtg cgt gcc cca acc aag     325
Glu Ser Val Val Ile Val Ser Arg His Gly Val Arg Ala Pro Thr Lys
                 35                  40                  45 gcc acg caa ctg atg cag gat gtc acc cca gac gca tgg cca acc tgg     373
Ala Thr Gln Leu Met Gln Asp Val Thr Pro Asp Ala Trp Pro Thr Trp
             50                  55                  60 ccg gta aaa ctg ggt tgg ctg aca cca cgc ggt ggt gag cta atc gcc     421
Pro Val Lys Leu Gly Trp Leu Thr Pro Arg Gly Gly Glu Leu Ile Ala
         65                  70                  75 tat ctc gga cat tac caa cgc cag cgt ctg gtg gcc gac gga ttg ctg     469
Tyr Leu Gly His Tyr Gln Arg Gln Arg Leu Val Ala Asp Gly Leu Leu
     80                  85                  90 gcg aaa aag ggc tgc ccg cag cct ggt cag gtc gcg att att gtc gat     517
Ala Lys Lys Gly Cys Pro Gln Pro Gly Gln Val Ala Ile Ile Val Asp
 95                 100                 105                 110 gtc gac gag cgt acc cgt aaa aca ggc gaa gcc ttc gcc gcc ggg ctg     565
Val Asp Glu Arg Thr Arg Lys Thr Gly Glu Ala Phe Ala Ala Gly Leu
                115                 120                 125 gca cct gac tgt gca ata acc gta cat acc cag gca gat acg tcc agt     613
Ala Pro Asp Cys Ala Ile Thr Val His Thr Gln Ala Asp Thr Ser Ser
            130                 135                 140 ccc gat ccg tta ttt att cct cta aaa act ggc gtt tgc caa ctg gat     661
Pro Asp Pro Leu Phe Ile Pro Leu Lys Thr Gly Val Cys Gln Leu Asp
        145                 150                 155 aac gcg aac gtg act gac gcg atc ctc agc agg gca gga ggg tca att     709
Asn Ala Asn Val Thr Asp Ala Ile Leu Ser Arg Ala Gly Gly Ser Ile
160                 165                 170 gct gac ttt acc ggg cat cgg caa acg gcg ttt cgc gaa ctg gaa cgg     757
Ala Asp Phe Thr Gly His Arg Gln Thr Ala Phe Arg Glu Leu Glu Arg
175                 180                 185                 190 gtg ctt aat ttt ccg caa tca aac ttg aac ctt aaa cgt gag aaa cag     805
Val Leu Asn Phe Pro Gln Ser Asn Leu Asn Leu Lys Arg Glu Lys Gln
                195                 200                 205 aat gaa agc tgt aac tta acg cag gca tta cca tcg gaa ctc aag gtg     853
Asn Glu Ser Cys Asn Leu Thr Gln Ala Leu Pro Ser Glu Leu Lys Val
            210                 215                 220
```

```
agc gcc gac aat gtt tca tta acc ggt gcg gta agc ctc gca tca atg      901
Ser Ala Asp Asn Val Ser Leu Thr Gly Ala Val Ser Leu Ala Ser Met
        225                 230                 235 ctg acg gaa ata ttt ctc ctg caa caa gca cag gga atg ccg gag ccg      949
Leu Thr Glu Ile Phe Leu Leu Gln Gln Ala Gln Gly Met Pro Glu Pro
    240                 245                 250 ggg tgg gga agg atc act gat tca cac cag tgg aac acc ttg cta agt      997
Gly Trp Gly Arg Ile Thr Asp Ser His Gln Trp Asn Thr Leu Leu Ser
255                 260                 265                 270 ttg cat aac gcg caa ttt tat tta caa cgc acg cca gag gtt gcc         1045
Leu His Asn Ala Gln Phe Tyr Leu Leu Gln Arg Thr Pro Glu Val Ala
                275                 280                 285 cgc agt cgc gcc acc ccg tta ttg gat ttg atc aag aca gcg ttg acg     1093
Arg Ser Arg Ala Thr Pro Leu Leu Asp Leu Ile Lys Thr Ala Leu Thr
            290                 295                 300 ccc cat cca ccg caa aaa cag gcg tat ggt gtg aca tta ccc act tca     1141
Pro His Pro Pro Gln Lys Gln Ala Tyr Gly Val Thr Leu Pro Thr Ser
        305                 310                 315 gtg ctg ttt att gcc gga cac gat act aat ctg gca aat ctc ggc ggc     1189
Val Leu Phe Ile Ala Gly His Asp Thr Asn Leu Ala Asn Leu Gly Gly
    320                 325                 330 gca ctg gag ctc aac tgg acg ctt cca ggt cag ccg gat aac acg ccg     1237
Ala Leu Glu Leu Asn Trp Thr Leu Pro Gly Gln Pro Asp Asn Thr Pro
335                 340                 345                 350 cca ggt ggt gaa ctg gtg ttt gaa cgc tgg cgt cgg cta agc gat aac     1285
Pro Gly Gly Glu Leu Val Phe Glu Arg Trp Arg Arg Leu Ser Asp Asn
                355                 360                 365 agc cag tgg att cag gtt tcg ctg gtc ttc cag act tta cag cag atg     1333
Ser Gln Trp Ile Gln Val Ser Leu Val Phe Gln Thr Leu Gln Gln Met
            370                 375                 380 cgt gat aaa acg ccg cta tca tta aat acg ccg ccc gga gag gtg aaa     1381
Arg Asp Lys Thr Pro Leu Ser Leu Asn Thr Pro Pro Gly Glu Val Lys
        385                 390                 395 ctg acc ctg gca gga tgt gaa gag cga aat gcg cag ggc atg tgt tcg     1429
Leu Thr Leu Ala Gly Cys Glu Glu Arg Asn Ala Gln Gly Met Cys Ser
    400                 405                 410 ttg gcc ggt ttt acg caa atc gtg aat gaa gcg cgc ata ccg gcg tgc     1477
Leu Ala Gly Phe Thr Gln Ile Val Asn Glu Ala Arg Ile Pro Ala Cys
415                 420                 425                 430 agt ttg taa                                                        1486
Ser Leu

<210> SEQ ID NO 5
<211> LENGTH: 432
<212> TYPE: PRT
<213> ORGANISM: Escherichia coli

<400> SEQUENCE: 5

Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
        35                  40                  45

Gln Leu Met Gln Asp Val Thr Pro Asp Ala Trp Pro Thr Trp Pro Val
    50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
```

```
                        85                  90                  95
Lys Gly Cys Pro Gln Pro Gly Gln Val Ala Ile Ile Val Asp Val Asp
                100                 105                 110

Glu Arg Thr Arg Lys Thr Gly Glu Ala Phe Ala Ala Gly Leu Ala Pro
            115                 120                 125

Asp Cys Ala Ile Thr Val His Thr Gln Ala Asp Thr Ser Ser Pro Asp
        130                 135                 140

Pro Leu Phe Ile Pro Leu Lys Thr Gly Val Cys Gln Leu Asp Asn Ala
145                 150                 155                 160

Asn Val Thr Asp Ala Ile Leu Ser Arg Ala Gly Ser Ile Ala Asp
                165                 170                 175

Phe Thr Gly His Arg Gln Thr Ala Phe Arg Glu Leu Glu Arg Val Leu
                180                 185                 190

Asn Phe Pro Gln Ser Asn Leu Asn Leu Lys Arg Glu Lys Gln Asn Glu
            195                 200                 205

Ser Cys Asn Leu Thr Gln Ala Leu Pro Ser Glu Leu Lys Val Ser Ala
        210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
                260                 265                 270

Asn Ala Gln Phe Tyr Leu Leu Gln Arg Thr Pro Glu Val Ala Arg Ser
            275                 280                 285

Arg Ala Thr Pro Leu Leu Asp Leu Ile Lys Thr Ala Leu Thr Pro His
        290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
                340                 345                 350

Gly Glu Leu Val Phe Glu Arg Trp Arg Arg Leu Ser Asp Asn Ser Gln
            355                 360                 365

Trp Ile Gln Val Ser Leu Val Phe Gln Thr Leu Gln Gln Met Arg Asp
        370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
                420                 425                 430
```

<210> SEQ ID NO 6
<211> LENGTH: 80
<212> TYPE: DNA
<213> ORGANISM: Artificial Sequence
<220> FEATURE:
<223> OTHER INFORMATION: Primer for amplifying appA gene.

<400> SEQUENCE: 6
ggggtaccat gggcgtctct gctgttctac ttcctttgta tctcctgtct ggagtcacct    60
ccggacagag tgagccggag                                                80

```
<210> SEQ ID NO 7
<211> LENGTH: 24
<212> TYPE: DNA
<213> ORGANISM: Artificial Sequence
<220> FEATURE:
<223> OTHER INFORMATION: Primer for amplifying appA gene.

<400> SEQUENCE: 7
gggaattcat tacaaactgc aggc                                          24

<210> SEQ ID NO 8
<211> LENGTH: 21
<212> TYPE: DNA
<213> ORGANISM: Artificial Sequence
<220> FEATURE:
<223> OTHER INFORMATION: Primer for amplifying appA gene.

<400> SEQUENCE: 8
ggaattccag agtgagccgg a                                             21

<210> SEQ ID NO 9
<211> LENGTH: 22
<212> TYPE: DNA
<213> ORGANISM: Artificial Sequence
<220> FEATURE:
<223> OTHER INFORMATION: Primer for amplifying appA gene.

<400> SEQUENCE: 9
ggggtacctt acaaactgca cg                                            22

<210> SEQ ID NO 10
<211> LENGTH: 31
<212> TYPE: DNA
<213> ORGANISM: Artificial Sequence
<220> FEATURE:
<223> OTHER INFORMATION: Primer for amplifying appA mutagenesis PCR
      amplification.

<400> SEQUENCE: 10
ctgggtatgg ttggttatat tacagtcagg t                                  31

<210> SEQ ID NO 11
<211> LENGTH: 23
<212> TYPE: DNA
<213> ORGANISM: Artificial Sequence
<220> FEATURE:
<223> OTHER INFORMATION: Primer for amplifying appA mutagenesis PCR
      amplification.

<400> SEQUENCE: 11
caaacttgaa ccttaaacgt gag                                           23

<210> SEQ ID NO 12
<211> LENGTH: 31
<212> TYPE: DNA
<213> ORGANISM: Artificial Sequence
<220> FEATURE:
<223> OTHER INFORMATION: Primer for amplifying appA mutagenesis PCR
      amplification.

<400> SEQUENCE: 12
cctgcgttaa gttacagctt tcattctgtt t                                  31

<210> SEQ ID NO 13
<211> LENGTH: 30
<212> TYPE: PRT
<213> ORGANISM: Escherichia coli
```

```
<400> SEQUENCE: 13

Met Trp Tyr Phe Leu Trp Phe Val Gly Ile Leu Leu Met Cys Ser Leu
1               5                   10                  15

Ser Thr Leu Val Leu Val Trp Leu Asp Pro Arg Leu Lys Ser
            20                  25                  30

<210> SEQ ID NO 14
<211> LENGTH: 432
<212> TYPE: PRT
<213> ORGANISM: Escherichia coli

<400> SEQUENCE: 14

Met Lys Ala Ile Leu Ile Pro Phe Leu Ser Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
                35                  40                  45

Gln Leu Met Gln Asp Val Thr Pro Asp Ala Trp Pro Thr Trp Pro Val
        50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Pro Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
            180                 185                 190

Asn Phe Ser Gln Leu Asn Leu Cys Leu Asn Arg Glu Lys Gln Asp Glu
        195                 200                 205

Ser Cys Ser Leu Thr Gln Ala Leu Pro Ser Glu Leu Lys Val Ser Ala
210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
        275                 280                 285

Arg Ala Thr Pro Leu Leu Asp Leu Ile Met Ala Ala Leu Thr Pro His
290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
```

-continued

```
                340                 345                 350
Gly Glu Leu Val Phe Glu Arg Trp Arg Arg Leu Ser Asp Asn Ser Gln
            355                 360                 365

Trp Ile Gln Val Ser Leu Val Phe Gln Thr Leu Gln Gln Met Arg Asp
        370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
            405                 410                 415

Gly Phe Thr Gln Ile Val Asn Glu Ala Arg Ile Pro Ala Cys Ser Leu
            420                 425                 430
```